(12) United States Patent
Shelton, IV

(10) Patent No.: US 11,937,799 B2
(45) Date of Patent: Mar. 26, 2024

(54) SURGICAL SEALING SYSTEMS FOR INSTRUMENT STABILIZATION

(71) Applicant: Cilag GmbH International, Zug (CH)

(72) Inventor: Frederick E. Shelton, IV, Hillsboro, OH (US)

(73) Assignee: Cilag GmbH International, Zug (CH)

(*) Notice: Subject to any disclaimer, the term of this patent is extended or adjusted under 35 U.S.C. 154(b) by 0 days.

(21) Appl. No.: 17/491,437

(22) Filed: Sep. 30, 2021

(65) Prior Publication Data
US 2023/0100415 A1    Mar. 30, 2023

Related U.S. Application Data

(60) Provisional application No. 63/249,980, filed on Sep. 29, 2021.

(51) Int. Cl.
*A61B 17/02* (2006.01)
*A61B 1/00* (2006.01)
(Continued)

(52) U.S. Cl.
CPC ...... *A61B 17/0218* (2013.01); *A61B 1/00004* (2013.01); *A61B 1/00006* (2013.01);
(Continued)

(58) Field of Classification Search
CPC .................................................. A61B 17/0218
(Continued)

(56) References Cited

U.S. PATENT DOCUMENTS 4,445,892 A    5/1984  Hussein et al.
4,470,407 A    9/1984  Hussein
(Continued)

FOREIGN PATENT DOCUMENTS

CA    2978771 A1    10/2016
EP    2226026 A1    9/2010
(Continued)

OTHER PUBLICATIONS

Kurata et al. (2013) "Time-of-flight Near-infrared Spectroscopy for Nondestructive Measurement of Internal Quality in Grapefruit", Journal of the American Society for Horticultural Science, 138(3):225-228.
(Continued)

*Primary Examiner* — Eduardo C Robert
*Assistant Examiner* — Tara Rose E Carter
(74) *Attorney, Agent, or Firm* — Mintz Levin Cohn Ferris Glovsky and Popeo, P.C.

(57) ABSTRACT

Surgical sealing systems are provided. In one exemplary embodiment, a surgical sealing system includes a seal housing having a plurality of ports, in which each of port has a nominal size and shape, is configured to assume a selected and/or shape that is different from the nominal size and shape, and is constrained by the size and shape of each of the other plurality of ports. The position of an instrument and a force applied thereto is effective to change the size and/or shape of the ports based on the movement, direction, and force of the instrument, and the ability to alter the nominal shape of any one port is constrained or limited by the size and shape of the other ports, thereby enabling a force applied to one instrument positioned within one of the plurality of ports to stabilize at least one other instrument positioned within others of the plurality of ports.

15 Claims, 28 Drawing Sheets

(51) Int. Cl.
| | | |
|---|---|---|
| A61B 1/313 | (2006.01) | |
| A61B 5/00 | (2006.01) | |
| A61B 17/00 | (2006.01) | |
| A61B 17/12 | (2006.01) | |
| A61B 17/34 | (2006.01) | |
| A61B 34/20 | (2016.01) | |
| A61B 34/30 | (2016.01) | |
| A61B 90/00 | (2016.01) | |
| A61B 90/50 | (2016.01) | |
| G06T 7/73 | (2017.01) | |
| H04N 13/111 | (2018.01) | |
| H04N 13/156 | (2018.01) | |

(52) U.S. Cl.
CPC .... *A61B 1/00009* (2013.01); *A61B 1/000095* (2022.02); *A61B 1/00045* (2013.01); *A61B 1/00048* (2013.01); *A61B 1/0005* (2013.01); *A61B 1/3132* (2013.01); *A61B 17/00234* (2013.01); *A61B 17/12099* (2013.01); *A61B 17/12104* (2013.01); *A61B 17/12136* (2013.01); *A61B 17/3421* (2013.01); *A61B 17/3474* (2013.01); *A61B 34/20* (2016.02); *A61B 34/30* (2016.02); *A61B 90/06* (2016.02); *A61B 90/361* (2016.02); *A61B 90/37* (2016.02); *A61B 90/39* (2016.02); *A61B 90/50* (2016.02); *G06T 7/74* (2017.01); *H04N 13/111* (2018.05); *H04N 13/156* (2018.05); *A61B 5/0075* (2013.01); *A61B 2017/00022* (2013.01); *A61B 2017/00057* (2013.01); *A61B 2017/00061* (2013.01); *A61B 2017/00075* (2013.01); *A61B 2017/00199* (2013.01); *A61B 2017/00292* (2013.01); *A61B 2017/00809* (2013.01); *A61B 2017/00818* (2013.01); *A61B 2017/3419* (2013.01); *A61B 2017/3484* (2013.01); *A61B 2034/2055* (2016.02); *A61B 2034/2057* (2016.02); *A61B 2034/301* (2016.02); *A61B 2090/064* (2016.02); *A61B 2090/3937* (2016.02); *A61B 2090/3945* (2016.02); *G06T 2207/10068* (2013.01)

(58) Field of Classification Search
USPC .................................................. 600/184–245
See application file for complete search history.

(56) References Cited

U.S. PATENT DOCUMENTS

| | | | |
|---|---|---|---|
| 5,505,700 | A | 4/1996 | Leone et al. |
| 6,004,271 | A | 12/1999 | Moore |
| 6,503,195 | B1 | 1/2003 | Keller et al. |
| 6,530,913 | B1 | 3/2003 | Giba et al. |
| 6,544,230 | B1 | 4/2003 | Flaherty et al. |
| 6,610,007 | B2 | 8/2003 | Belson et al. |
| 6,669,709 | B1 | 12/2003 | Cohn et al. |
| 6,905,460 | B2 | 6/2005 | Wang et al. |
| 7,371,210 | B2 | 5/2008 | Brock et al. |
| 8,052,636 | B2 | 11/2011 | Moll et al. |
| 8,068,649 | B2 | 11/2011 | Green |
| 8,257,303 | B2 | 9/2012 | Moll et al. |
| 8,517,933 | B2 | 8/2013 | Mohr |
| 8,545,515 | B2 | 10/2013 | Prisco et al. |
| 8,551,115 | B2 | 10/2013 | Steger et al. |
| 8,623,028 | B2 | 1/2014 | Rogers et al. |
| 8,771,180 | B2 | 7/2014 | Mohr |
| 8,831,782 | B2 | 9/2014 | Itkowitz |
| 8,888,789 | B2 | 11/2014 | Prisco et al. |
| 9,254,178 | B2 | 2/2016 | Prisco et al. |
| 9,269,682 | B2 | 2/2016 | Yu et al. |
| 9,274,047 | B2 | 3/2016 | Velten et al. |
| 9,283,050 | B2 | 3/2016 | Prisco et al. |
| 9,320,416 | B2 | 4/2016 | Cooper et al. |
| 9,339,341 | B2 | 5/2016 | Cooper |
| 9,358,074 | B2 | 6/2016 | Schena et al. |
| 9,572,481 | B2 | 2/2017 | Duindam et al. |
| 9,636,186 | B2 | 5/2017 | Kumar et al. |
| 9,861,271 | B2 | 1/2018 | Liu et al. |
| 10,245,069 | B2 | 4/2019 | Rogers et al. |
| 10,368,838 | B2 | 8/2019 | Williams et al. |
| 10,456,202 | B2 | 10/2019 | Sholev et al. |
| 10,492,665 | B2 | 12/2019 | Dejima |
| 10,792,034 | B2 | 10/2020 | Scheib et al. |
| 10,925,598 | B2 | 2/2021 | Scheib et al. |
| 11,051,876 | B2 | 7/2021 | Shelton, IV et al. |
| 2001/0009976 | A1 | 7/2001 | Panescu et al. |
| 2001/0029366 | A1 | 10/2001 | Swanson et al. |
| 2002/0087169 | A1 | 7/2002 | Brock et al. |
| 2002/0177789 | A1 | 11/2002 | Ferry et al. |
| 2003/0074011 | A1 | 4/2003 | Gilboa et al. |
| 2003/0135204 | A1 | 7/2003 | Lee et al. |
| 2004/0176751 | A1 | 9/2004 | Weitzner et al. |
| 2004/0193146 | A1 | 9/2004 | Lee et al. |
| 2005/0182295 | A1 | 8/2005 | Soper et al. |
| 2007/0060879 | A1 | 3/2007 | Weitzner et al. |
| 2007/0162106 | A1 | 7/2007 | Evans et al. |
| 2008/0300592 | A1 | 12/2008 | Weitzner et al. |
| 2009/0012618 | A1* | 1/2009 | Ahrens .............. A61B 17/7094 606/191 |
| 2009/0054884 | A1 | 2/2009 | Farley et al. |
| 2009/0171196 | A1 | 7/2009 | Hauck et al. |
| 2010/0081881 | A1 | 4/2010 | Murray et al. |
| 2010/0228096 | A1 | 9/2010 | Weisenburgh, II et al. |
| 2010/0240960 | A1 | 9/2010 | Richard |
| 2010/0312063 | A1* | 12/2010 | Hess .................. A61B 17/3423 600/204 |
| 2010/0312065 | A1 | 12/2010 | Shelton et al. |
| 2011/0071543 | A1* | 3/2011 | Prisco .................... A61B 34/76 600/118 |
| 2011/0152788 | A1 | 6/2011 | Hotter |
| 2011/0295074 | A1 | 12/2011 | Stefanchik et al. |
| 2012/0130188 | A1* | 5/2012 | Okoniewski ....... A61B 17/3423 600/208 |
| 2013/0266029 | A1* | 10/2013 | Yi ............................ H04L 49/10 370/535 |
| 2014/0066717 | A1 | 3/2014 | Rogers et al. |
| 2014/0194732 | A1 | 7/2014 | Nakaguchi |
| 2015/0145953 | A1 | 5/2015 | Fujie et al. |
| 2016/0007979 | A1 | 1/2016 | Bhagat et al. |
| 2016/0331473 | A1 | 11/2016 | Yamamura |
| 2017/0024903 | A1 | 1/2017 | Razzaque |
| 2017/0055819 | A1 | 3/2017 | Hansen et al. |
| 2017/0086653 | A1 | 3/2017 | Yeung et al. |
| 2017/0128041 | A1 | 5/2017 | Hasser et al. |
| 2017/0128144 | A1 | 5/2017 | Hasser et al. |
| 2017/0128145 | A1 | 5/2017 | Hasser et al. |
| 2017/0172662 | A1 | 6/2017 | Panescu et al. |
| 2017/0181808 | A1 | 6/2017 | Panescu et al. |
| 2017/0251900 | A1 | 9/2017 | Hansen et al. |
| 2018/0042680 | A1 | 2/2018 | Dimaio et al. |
| 2018/0049821 | A1 | 2/2018 | Shelton, IV et al. |
| 2018/0070800 | A1 | 3/2018 | Yeung et al. |
| 2018/0177556 | A1 | 6/2018 | Noonan |
| 2018/0256008 | A1 | 9/2018 | Nishizawa |
| 2018/0276877 | A1 | 9/2018 | Mountney et al. |
| 2018/0296280 | A1 | 10/2018 | Kurihara et al. |
| 2018/0325604 | A1 | 11/2018 | Atarot et al. |
| 2019/0117209 | A1* | 4/2019 | Augelli .............. A61M 13/003 |
| 2019/0200844 | A1 | 7/2019 | Shelton, IV et al. |
| 2019/0200981 | A1 | 7/2019 | Harris et al. |
| 2019/0201046 | A1 | 7/2019 | Shelton, IV et al. |
| 2019/0201088 | A1 | 7/2019 | Shelton, IV et al. |
| 2019/0201114 | A1 | 7/2019 | Shelton, IV et al. |
| 2019/0201136 | A1 | 7/2019 | Shelton, IV et al. |
| 2019/0201140 | A1 | 7/2019 | Yates et al. |
| 2019/0204201 | A1 | 7/2019 | Shelton, IV et al. |
| 2019/0206004 | A1 | 7/2019 | Shelton, IV et al. |
| 2019/0206555 | A1 | 7/2019 | Morgan et al. |
| 2019/0207857 | A1 | 7/2019 | Shelton, IV et al. |
| 2019/0290247 | A1 | 9/2019 | Popovic et al. |
| 2020/0000530 | A1 | 1/2020 | Defonzo et al. |

(56) References Cited

U.S. PATENT DOCUMENTS

| | | |
|---|---|---|
| 2020/0015668 A1 | 1/2020 | Scheib |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0037863 A1 | 2/2020 | Harris et al. |
| 2020/0060524 A1 | 2/2020 | Weitzner |
| 2020/0085516 A1 | 3/2020 | Defonzo et al. |
| 2020/0170720 A1 | 6/2020 | Ummalaneni |
| 2020/0178948 A1 | 6/2020 | Piskun et al. |
| 2020/0188043 A1 | 6/2020 | Yu et al. |
| 2020/0222078 A1 | 7/2020 | Dharan et al. |
| 2020/0306004 A1 | 10/2020 | Batchelor et al. |
| 2020/0315723 A1 | 10/2020 | Hassan et al. |
| 2021/0085410 A1 | 3/2021 | Hassan |
| 2021/0196108 A1 | 7/2021 | Shelton, IV et al. |
| 2021/0196109 A1 | 7/2021 | Shelton, IV et al. |
| 2021/0196381 A1 | 7/2021 | Eckert et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0196424 A1 | 7/2021 | Shelton, IV et al. |
| 2021/0196425 A1 | 7/2021 | Shelton, IV et al. |
| 2021/0199557 A1 | 7/2021 | Shelton, IV et al. |
| 2021/0343088 A1 | 11/2021 | Payyavula et al. |
| 2021/0345952 A1 | 11/2021 | Harris et al. |
| 2021/0345953 A1 | 11/2021 | Shelton, IV et al. |
| 2021/0346015 A1 | 11/2021 | Krulevitch et al. |
| 2021/0350895 A1 | 11/2021 | Bakos et al. |
| 2021/0350896 A1 | 11/2021 | Shelton, IV et al. |
| 2021/0350897 A1 | 11/2021 | Shelton, IV et al. |
| 2021/0393338 A1 | 12/2021 | Graetzel et al. |
| 2022/0175269 A1 | 6/2022 | Lu et al. |
| 2023/0110791 A1 | 4/2023 | Shelton, IV et al. |

FOREIGN PATENT DOCUMENTS

| | | | |
|---|---|---|---|
| EP | 3275386 A1 | 1/2018 | |
| WO | WO-2007081800 A2 * | 7/2007 | ......... A61B 17/0218 |
| WO | 2014151621 A1 | 9/2014 | |
| WO | 2020018566 A1 | 1/2020 | |

OTHER PUBLICATIONS

Lee et al. (Nov. 11-15, 2007) "Design of a Magnetic Field-Based Multi Degree-of-Freedom Orientation Sensor Using the Distributed-Multiple-Pole Model", IMECE2007-42106-Proceedings of IMECE2007, 2007 ASME International Mechanical Engineering Congress and Exposition, Seattle, Washington, USA, 6 pages.

U.S. Appl. No. 17/449,765, filed Oct. 1, 2021, Cooperative Access Hybrid Procedures.

U.S. Appl. No. 17/449,767, filed Oct. 1, 2021, Surgical Anchoring Systems for Endoluminal Access.

U.S. Appl. No. 17/449,769, filed Oct. 1, 2021, Instrument Control Surgical Imaging Systems.

U.S. Appl. No. 17/449,770, filed Oct. 1, 2021, Instrument Control Imaging Systems for Visualization of Upcoming Surgical Procedure Steps.

U.S. Appl. No. 17/449,771, filed Oct. 1, 2021, Coordinated Instrument Control Systems.

U.S. Appl. No. 17/491,375, filed Sep. 30, 2021, Surgical Sealing Devices for a Natural Body Orifice.

U.S. Appl. No. 17/491,383, filed Sep. 30, 2021, Surgical Systems With Port Devices for Instrument Control.

U.S. Appl. No. 17/493,526, filed Oct. 4, 2021, Surgical Systems With Devices for Both Intraluminal and Extraluminal Access.

U.S. Appl. No. 17/493,535, filed Oct. 4, 2021, Surgical Systems With Intraluminal and Extraluminal Cooperative Instruments.

U.S. Appl. No. 17/493,545, filed Oct. 4, 2021, Surgical Systems for Independently Insufflating Two Separate Anatomic Spaces.

U.S. Appl. No. 17/449,772, filed Oct. 1, 2021, Surgical Systems and Methods for Selectively Pressurizing a Natural Body Lumen.

International Search Report and Written Opinion for Patent Application No. PCT/IB2022/059079 dated Mar. 13, 2023, 17 pages.

International Search Report and Written Opinion for Patent Application No. PCT/IB2022/059082 dated Mar. 14, 2023, 24 pages.

International Search Report and Written Opinion for International Application No. PCT/IB2022/059103, dated Jan. 2, 2023, 16 pages.

Invitation to Pay Additional Fees for International Application No. PCT/IB2022/059079 dated Jan. 12, 2023, 12 pages.

Invitation to Pay Additional Fees for International Application No. PCT/IB2022/059080 dated Dec. 9, 2022, 16 pages.

* cited by examiner

SURGICAL SEALING SYSTEMS FOR INSTRUMENT STABILIZATION

CROSS-REFERENCE TO RELATED APPLICATIONS

This application claims priority to U.S. Provisional Patent Application No. 63/249,980 filed on Sep. 29, 2021, and entitled "Cooperative Access," the disclosure of which is incorporated herein by reference in its entirety.

FIELD

The present invention relates generally to surgical devices, systems, and methods of using the same for sealing, instrument control, instrument stabilization, etc.

BACKGROUND

Surgical systems often incorporate an imaging system, which can allow medical practitioners to view a surgical site and/or one or more portions thereof on one or more displays, (e.g., a monitor, a computer tablet screen, etc.). The display(s) can be local and/or remote to a surgical theater. The imaging system can include a scope with a camera that views the surgical site and transmits the view to the one or more displays viewable by medical practitioner(s).

Imaging systems can be limited by the information that they are able to recognize and/or convey to the medical practitioner(s). For example, certain concealed structures, physical contours, and/or dimensions within a three-dimensional space may be unrecognizable intraoperatively by certain imaging systems. For another example, certain imaging systems may be incapable of communicating and/or conveying certain information to the medical practitioner(s) intraoperatively.

Accordingly, there remains a need for improved surgical imaging.

SUMMARY

Surgical sealing systems are provided. In one exemplary embodiment, the sealing system includes a sealing device having a seal housing with a predetermined size and shape. The seal housing is configured to be at least partially disposed within a body cavity and has a plurality of ports. Each of the plurality of ports has a nominal size and shape and each is configured to assume a selected size and/or shape that is different from the nominal size and/or shape. The selected size and/or shape of each port being constrained by the size and shape of each of the other plurality of ports, Each of the plurality of ports is configured to form a seal around an instrument inserted therethrough. The position of an instrument that is positioned within one port of the plurality of ports and a force applied thereto is effective to change the size and/or shape of the ports based on the movement, direction, and force of the instrument, and the ability to alter the nominal shape of any one port is constrained or limited by the size and/or shape of the other ports, thereby enabling a force applied to one instrument positioned within one of the plurality of ports to stabilize at least one other instrument positioned within others of the plurality of ports.

In some embodiments, the surgical sealing system can include at least one electromechanical arm, in which at least one instrument that is inserted into a respective port of the plurality of ports can be connected to the at least one electromechanical arm.

The surgical sealing device can have a variety of configurations. In some embodiments, the sealing device can include a retractor that can be coupled to the seal housing and can be configured to be positioned in a natural body orifice or an opening formed in tissue. In other embodiments, the sealing device can include at least one retention element that can be configured to affix the seal housing to tissue.

The plurality of ports can have a variety of configurations. In some embodiments, a first port of the plurality of ports can be configured to apply a first force to a first instrument that is inserted therethrough to thereby limit movement thereof within a first plane, and a second port of the plurality of ports can be configured to apply a second force to a second instrument that is inserted therethrough to thereby limit movement thereof within a second plane, the second plane being non-parallel to the first plane. In certain embodiments, one or more ports of the plurality of ports can be rigid relative to one or more other ports of the plurality of ports.

In some embodiments, at least one port of the plurality of ports can include a threaded restraint configured to fixate an instrument inserted therethrough. In other embodiments, at least one port of the plurality of ports can be configured to change shape and size in response to external energy being applied thereto.

In some embodiments, at least one port of the plurality of ports can be formed of a ferromagnetic material that can be configured to be structurally altered in response to exposure to an electromagnet. In other embodiments, at least one port of the plurality of ports can include a locking arm arranged within a slot of the seal housing, the locking arm can be configured to lock a position of the at least one port relative to the seal housing.

In some embodiments, at least one port of the plurality of ports can include a locking structure that can be configured to interact and collapse around an instrument passing therethrough to fixate the inserted instrument within the at least one port. In one embodiment, the locking structure can have a honeycomb configuration.

In some embodiments, a first instrument and a second instrument that can be inserted into respective ports of the plurality of ports can be stabilized simultaneously by a central anchoring tool that can be configured to be inserted through a port of the plurality of ports.

The surgical housing can have a variety of configurations. In some embodiments, the sealing housing can include a flexible inner body member and a rigid outer body member, wherein each port of the plurality of ports can be arranged within the inner body member. In one embodiment, at least one port of the plurality of ports can include a rigid ring encapsulated by the flexible inner body member.

BRIEF DESCRIPTION OF DRAWINGS

The present invention is described by way of reference to the accompanying figures which are as follows.

DETAILED DESCRIPTION

Figure 1:
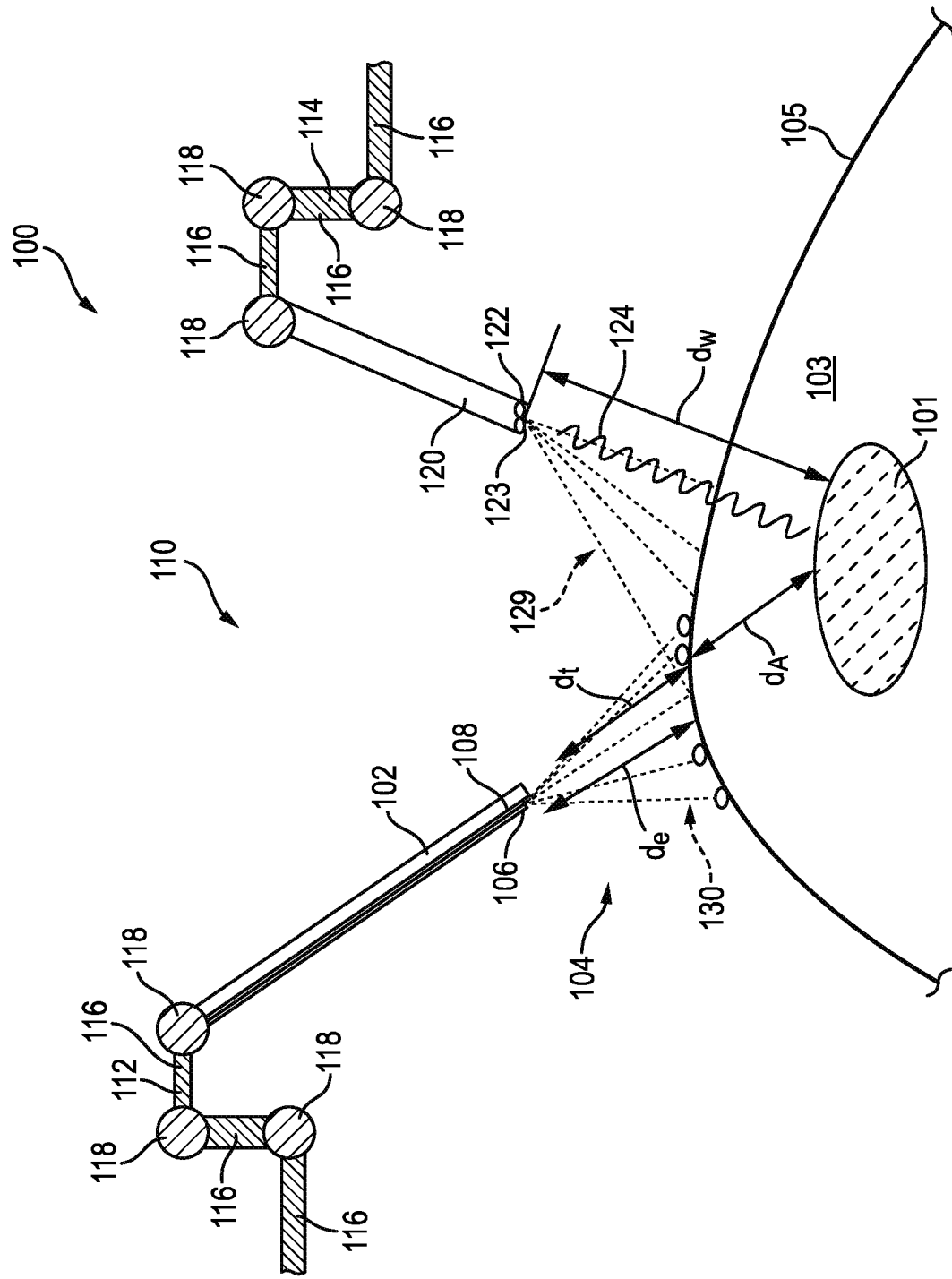
FIG. 1 is a schematic view of one embodiment of a surgical visualization system.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Surgical Visualization

In general, a surgical visualization system is configured to leverage "digital surgery" to obtain additional information about a patient's anatomy and/or a surgical procedure. The surgical visualization system is further configured to convey data to one or more medical practitioners in a helpful manner. Various aspects of the present disclosure provide improved visualization of the patient's anatomy and/or the surgical procedure, and/or use visualization to provide improved control of a surgical tool (also referred to herein as a "surgical device" or a "surgical instrument").

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization systems described herein can be used in combination with a robotic surgical system, surgical visualization systems are not limited to use with a robotic surgical system. In certain instances, surgical visualization using a surgical visualization system can occur without robotics and/or with limited and/or optional robotic assistance. Similarly, digital surgery can occur without robotics and/or with limited and/or optional robotic assistance.

In certain instances, a surgical system that incorporates a surgical visualization system may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, a surgical fastener, a clip, a tack, a bougie, a band, a plate, and other foreign structures. Critical structures can be determined on a patient-by-patient and/or a procedure-by-procedure basis. Smart dissection technology may provide, for example, improved intraoperative guidance for dissection and/or may enable smarter decisions with critical anatomy detection and avoidance technology.

A surgical system incorporating a surgical visualization system may enable smart anastomosis technologies that provide more consistent anastomoses at optimal location(s) with improved workflow. Cancer localization technologies may be improved with a surgical visualization platform. For example, cancer localization technologies can identify and track a cancer location, orientation, and its margins. In certain instances, the cancer localization technologies may compensate for movement of a surgical instrument, a patient, and/or the patient's anatomy during a surgical procedure in order to provide guidance back to the point of interest for medical practitioner(s).

A surgical visualization system may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies may be utilized without ionizing radiation and/or contrast agents. With respect to lymph node diagnostics and mapping, a surgical visualization platform may, for example, preoperatively locate, map, and ideally diagnose the lymph system and/or lymph nodes involved in cancerous diagnosis and staging.

During a surgical procedure, information available to a medical practitioner via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move pre-operatively (e.g., before a surgical procedure but after a preoperative scan) and/or intraoperatively. In such instances, the medical practitioner can be unable to accurately determine the location of a critical structure intraoperatively.

When the position of a critical structure is uncertain and/or when the proximity between the critical structure and a surgical tool is unknown, a medical practitioner's decision-making process can be inhibited. For example, a medical practitioner may avoid certain areas in order to avoid inadvertent dissection of a critical structure; however, the avoided area may be unnecessarily large and/or at least partially misplaced. Due to uncertainty and/or overly/excessive exercises in caution, the medical practitioner may not access certain desired regions. For example, excess caution may cause a medical practitioner to leave a portion of a tumor and/or other undesirable tissue in an effort to avoid a critical structure even if the critical structure is not in the particular area and/or would not be negatively impacted by the medical practitioner working in that particular area. In certain instances, surgical results can be improved with increased knowledge and/or certainty, which can allow a surgeon to be more accurate and, in certain instances, less conservative/more aggressive with respect to particular anatomical areas.

A surgical visualization system can allow for intraoperative identification and avoidance of critical structures. The surgical visualization system may thus enable enhanced intraoperative decision making and improved surgical outcomes. The surgical visualization system can provide advanced visualization capabilities beyond what a medical practitioner sees with the "naked eye" and/or beyond what an imaging system can recognize and/or convey to the medical practitioner. The surgical visualization system can augment and enhance what a medical practitioner is able to know prior to tissue treatment (e.g., dissection, etc.) and, thus, may improve outcomes in various instances. As a result, the medical practitioner can confidently maintain momentum throughout the surgical procedure knowing that the surgical visualization system is tracking a critical structure, which may be approached during dissection, for example. The surgical visualization system can provide an indication to the medical practitioner in sufficient time for the medical practitioner to pause and/or slow down the surgical procedure and evaluate the proximity to the critical structure to prevent inadvertent damage thereto. The surgical visualization system can provide an ideal, optimized, and/or customizable amount of information to the medical practitioner to allow the medical practitioner to move confidently and/or quickly through tissue while avoiding inadvertent damage to healthy tissue and/or critical structure(s) and, thus, to minimize the risk of harm resulting from the surgical procedure.

Surgical visualization systems are described in detail below. In general, a surgical visualization system can include a first light emitter configured to emit a plurality of spectral waves, a second light emitter configured to emit a light pattern, and a receiver, or sensor, configured to detect visible light, molecular responses to the spectral waves (spectral imaging), and/or the light pattern. The surgical visualization system can also include an imaging system and a control circuit in signal communication with the receiver and the imaging system. Based on output from the receiver, the control circuit can determine a geometric surface map, e.g., three-dimensional surface topography, of the visible surfaces at the surgical site and a distance with respect to the surgical site, such as a distance to an at least partially concealed structure. The imaging system can convey the geometric surface map and the distance to a medical practitioner. In such instances, an augmented view of the surgical site provided to the medical practitioner can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of a surgical tool to the visible and obstructing tissue and/or to the at least partially concealed structure and/or a depth of the concealed structure below the visible surface of the obstructing tissue. For example, the visualization system can determine a distance with respect to the augmented line on the surface of the visible tissue and convey the distance to the imaging system.

Throughout the present disclosure, any reference to "light," unless specifically in reference to visible light, can include electromagnetic radiation (EMR) or photons in the visible and/or non-visible portions of the EMR wavelength spectrum. The visible spectrum, sometimes referred to as the optical spectrum or luminous spectrum, is that portion of the electromagnetic spectrum that is visible to (e.g., can be detected by) the human eye and may be referred to as "visible light" or simply "light." A typical human eye will respond to wavelengths in air that are from about 380 nm to about 750 nm. The invisible spectrum (e.g., the non-luminous spectrum) is that portion of the electromagnetic spectrum that lies below and above the visible spectrum. The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

FIG. 1 illustrates one embodiment of a surgical visualization system 100. The surgical visualization system 100 is configured to create a visual representation of a critical structure 101 within an anatomical field. The critical structure 101 can include a single critical structure or a plurality of critical structures. As discussed herein, the critical structure 101 can be any of a variety of structures, such as an anatomical structure, e.g., a ureter, an artery such as a superior mesenteric artery, a vein such as a portal vein, a nerve such as a phrenic nerve, a vessel, a tumor, or other anatomical structure, or a foreign structure, e.g., a surgical device, a surgical fastener, a surgical clip, a surgical tack, a bougie, a surgical band, a surgical plate, or other foreign structure. As discussed herein, the critical structure 101 can be identified on a patient-by-patient and/or a procedure-by-procedure basis. Embodiments of critical structures and of identifying critical structures using a visualization system are further described in U.S. Pat. No. 10,792,034 entitled "Visualization Of Surgical Devices" issued Oct. 6, 2020, which is hereby incorporated by reference in its entirety.

In some instances, the critical structure 101 can be embedded in tissue 103. The tissue 103 can be any of a variety of tissues, such as fat, connective tissue, adhesions, and/or organs. Stated differently, the critical structure 101 may be positioned below a surface 105 of the tissue 103. In such instances, the tissue 103 conceals the critical structure 101 from the medical practitioner's "naked eye" view. The tissue 103 also obscures the critical structure 101 from the view of an imaging device 120 of the surgical visualization system 100. Instead of being fully obscured, the critical structure 101 can be partially obscured from the view of the medical practitioner and/or the imaging device 120.

The surgical visualization system 100 can be used for clinical analysis and/or medical intervention. In certain instances, the surgical visualization system 100 can be used intraoperatively to provide real-time information to the medical practitioner during a surgical procedure, such as real-time information regarding proximity data, dimensions, and/or distances. A person skilled in the art will appreciate that information may not be precisely real time but nevertheless be considered to be real time for any of a variety of reasons, such as time delay induced by data transmission, time delay induced by data processing, and/or sensitivity of measurement equipment. The surgical visualization system 100 is configured for intraoperative identification of critical structure(s) and/or to facilitate the avoidance of the critical structure(s) 101 by a surgical device. For example, by identifying the critical structure 101, a medical practitioner can avoid maneuvering a surgical device around the critical structure 101 and/or a region in a predefined proximity of the critical structure 101 during a surgical procedure. For another example, by identifying the critical structure 101, a medical practitioner can avoid dissection of and/or near the critical structure 101, thereby helping to prevent damage to the critical structure 101 and/or helping to prevent a surgical device being used by the medical practitioner from being damaged by the critical structure 101.

The surgical visualization system 100 is configured to incorporate tissue identification and geometric surface mapping in combination with the surgical visualization system's distance sensor system 104. In combination, these features of the surgical visualization system 100 can determine a position of a critical structure 101 within the anatomical field and/or the proximity of a surgical device 102 to the surface 105 of visible tissue 103 and/or to the critical structure 101. Moreover, the surgical visualization system 100 includes an imaging system that includes the imaging device 120 configured to provide real-time views of the surgical site. The imaging device 120 can include, for example, a spectral camera (e.g., a hyperspectral camera, multispectral camera, or selective spectral camera), which is configured to detect reflected spectral waveforms and generate a spectral cube of images based on the molecular response to the different wavelengths. Views from the imaging device 120 can be provided in real time to a medical practitioner, such as on a display (e.g., a monitor, a computer tablet screen, etc.). The displayed views can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the medical practitioner.

The imaging device 120 can be configured to detect visible light, spectral light waves (visible or invisible), and a structured light pattern (visible or invisible). Examples of the imaging device 120 includes scopes, e.g., an endoscope, an arthroscope, an angioscope, a bronchoscope, a choledochoscope, a colonoscope, a cytoscope, a duodenoscope, an enteroscope, an esophagogastro-duodenoscope (gastroscope), a laryngoscope, a nasopharyngo-neproscope, a sigmoidoscope, a thoracoscope, an ureteroscope, or an exoscope. Scopes can be particularly useful in minimally invasive surgical procedures. In open surgery applications, the imaging device 120 may not include a scope.

The tissue identification subsystem can be achieved with a spectral imaging system. The spectral imaging system can rely on imaging such as hyperspectral imaging, multispectral imaging, or selective spectral imaging. Embodiments of hyperspectral imaging of tissue are further described in U.S. Pat. No. 9,274,047 entitled "System And Method For Gross Anatomic Pathology Using Hyperspectral Imaging" issued Mar. 1, 2016, which is hereby incorporated by reference in its entirety.

The surface mapping subsystem can be achieved with a light pattern system. Various surface mapping techniques using a light pattern (or structured light) for surface mapping can be utilized in the surgical visualization systems described herein. Structured light is the process of projecting a known pattern (often a grid or horizontal bars) on to a surface. In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Embodiments of surface mapping and a surgical system including a light source and a projector for projecting a light pattern are further described in U.S. Pat. Pub. No. 2017/0055819 entitled "Set Comprising A Surgical Instrument" published Mar. 2, 2017, U.S. Pat. Pub. No. 2017/0251900 entitled "Depiction System" published Sep. 7, 2017, and U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, which are hereby incorporated by reference in their entireties.

The distance determining system can be incorporated into the surface mapping system. For example, structured light can be utilized to generate a three-dimensional (3D) virtual model of the visible surface 105 and determine various distances with respect to the visible surface 105. Additionally or alternatively, the distance determining system can rely on time-of-flight measurements to determine one or more distances to the identified tissue (or other structures) at the surgical site.

The surgical visualization system 100 also includes a surgical device 102. The surgical device 102 can be any suitable surgical device. Examples of the surgical device 102 includes a surgical dissector, a surgical stapler, a surgical grasper, a clip applier, a smoke evacuator, a surgical energy device (e.g., mono-polar probes, bi-polar probes, ablation probes, an ultrasound device, an ultrasonic end effector, etc.), etc. In some embodiments, the surgical device 102 includes an end effector having opposing jaws that extend from a distal end of a shaft of the surgical device 102 and that are configured to engage tissue therebetween.

The surgical visualization system 100 can be configured to identify the critical structure 101 and a proximity of the surgical device 102 to the critical structure 101. The imaging device 120 of the surgical visualization system 100 is configured to detect light at various wavelengths, such as visible light, spectral light waves (visible or invisible), and a structured light pattern (visible or invisible). The imaging device 120 can include a plurality of lenses, sensors, and/or receivers for detecting the different signals. For example, the imaging device 120 can be a hyperspectral, multispectral, or selective spectral camera, as described herein. The imaging device 120 can include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional (3D) image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, a field of view of the imaging device 120 can overlap with a pattern of light (structured light) on the surface 105 of the tissue 103, as shown in FIG. 1.

As in this illustrated embodiment, the surgical visualization system 100 can be incorporated into a robotic surgical system 110. The robotic surgical system 110 can have a variety of configurations, as discussed herein. In this illustrated embodiment, the robotic surgical system 110 includes a first robotic arm 112 and a second robotic arm 114. The robotic arms 112, 114 each include rigid structural members 116 and joints 118, which can include servomotor controls. The first robotic arm 112 is configured to maneuver the surgical device 102, and the second robotic arm 114 is configured to maneuver the imaging device 120. A robotic control unit of the robotic surgical system 110 is configured to issue control motions to the first and second robotic arms 112, 114, which can affect the surgical device 102 and the imaging device 120, respectively.

In some embodiments, one or more of the robotic arms 112, 114 can be separate from the main robotic system 110 used in the surgical procedure. For example, at least one of the robotic arms 112, 114 can be positioned and registered to a particular coordinate system without a servomotor control. For example, a closed-loop control system and/or a plurality of sensors for the robotic arms 112, 114 can control and/or register the position of the robotic arm(s) 112, 114 relative to the particular coordinate system. Similarly, the position of the surgical device 102 and the imaging device 120 can be registered relative to a particular coordinate system.

Examples of robotic surgical systems include the Ottava™ robotic-assisted surgery system (Johnson & Johnson of New Brunswick, NJ), da Vinci® surgical systems (Intuitive Surgical, Inc. of Sunnyvale, CA), the Hugo™ robotic-assisted surgery system (Medtronic PLC of Minneapolis, MN), the Versius® surgical robotic system (CMR Surgical Ltd of Cambridge, UK), and the Monarch® platform (Auris Health, Inc. of Redwood City, CA). Embodiments of various robotic surgical systems and using robotic surgical systems are further described in U.S. Pat. Pub. No. 2018/0177556 entitled "Flexible Instrument Insertion Using An Adaptive Force Threshold" filed Dec. 28, 2016, U.S. Pat. Pub. No. 2020/0000530 entitled "Systems And Techniques For Providing Multiple Perspectives During Medical Procedures" filed Apr. 16, 2019, U.S. Pat. Pub. No. 2020/0170720 entitled "Image-Based Branch Detection And Mapping For Navigation" filed Feb. 7, 2020, U.S. Pat. Pub. No. 2020/0188043 entitled "Surgical Robotics System" filed Dec. 9, 2019, U.S. Pat. Pub. No. 2020/0085516 entitled "Systems And Methods For Concomitant Medical Procedures" filed Sep. 3, 2019, U.S. Pat. No. 8,831,782 entitled "Patient-Side Surgeon Interface For A Teleoperated Surgical Instrument" filed Jul. 15, 2013, and Intl. Pat. Pub. No. WO 2014151621 entitled "Hyperdexterous Surgical System" filed Mar. 13, 2014, which are hereby incorporated by reference in their entireties.

The surgical visualization system 100 also includes an emitter 106. The emitter 106 is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120. In one aspect, the projected light array 130 is employed by the surgical visualization system 100 to determine the shape defined by the surface 105 of the tissue 103 and/or motion of the surface 105 intraoperatively. The imaging device 120 is configured to detect the projected light arrays 130 reflected from the surface 105 to determine the topography of the surface 105 and various distances with respect to the surface 105.

As in this illustrated embodiment, the imaging device 120 can include an optical waveform emitter 123, such as by being mounted on or otherwise attached on the imaging device 120. The optical waveform emitter 123 is configured to emit electromagnetic radiation 124 (near-infrared (NIR) photons) that can penetrate the surface 105 of the tissue 103 and reach the critical structure 101. The imaging device 120 and the optical waveform emitter 123 can be positionable by the robotic arm 114. The optical waveform emitter 123 is mounted on or otherwise on the imaging device 122 but in other embodiments can be positioned on a separate surgical device from the imaging device 120. A corresponding waveform sensor 122 (e.g., an image sensor, spectrometer, or vibrational sensor) of the imaging device 120 is configured to detect the effect of the electromagnetic radiation received by the waveform sensor 122. The wavelengths of the electromagnetic radiation 124 emitted by the optical waveform emitter 123 are configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 can be variable. The waveform sensor 122 and optical waveform emitter 123 can be inclusive of a multispectral imaging system and/or a selective spectral imaging system, for example. In other instances, the waveform sensor 122 and optical waveform emitter 123 can be inclusive of a photoacoustic imaging system, for example.

The distance sensor system 104 of the surgical visualization system 100 is configured to determine one or more distances at the surgical site. The distance sensor system 104 can be a time-of-flight distance sensor system that includes an emitter, such as the emitter 106 as in this illustrated embodiment, and that includes a receiver 108. In other instances, the time-of-flight emitter can be separate from the structured light emitter. The emitter 106 can include a very tiny laser source, and the receiver 108 can include a matching sensor. The distance sensor system 104 is configured to detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104.

The receiver 108 of the distance sensor system 104 is positioned on the surgical device 102 in this illustrated embodiment, but in other embodiments the receiver 108 can be mounted on a separate surgical device instead of the surgical device 102. For example, the receiver 108 can be mounted on a cannula or trocar through which the surgical device 102 extends to reach the surgical site. In still other embodiments, the receiver 108 for the distance sensor system 104 can be mounted on a separate robotically-controlled arm of the robotic system 110 (e.g., on the second robotic arm 114) than the first robotic arm 112 to which the surgical device 102 is coupled, can be mounted on a movable arm that is operated by another robot, or be mounted to an operating room (OR) table or fixture. In some embodiments, the imaging device 120 includes the receiver 108 to allow for determining the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the distance sensor system 104. The three-dimensional position of the receiver 108 can be known and/or registered to the robot coordinate plane intraoperatively.

As in this illustrated embodiment, the position of the emitter 106 of the distance sensor system 104 can be controlled by the first robotic arm 112, and the position of the receiver 108 of the distance sensor system 104 can be controlled by the second robotic arm 114. In other embodiments, the surgical visualization system 100 can be utilized apart from a robotic system. In such instances, the distance sensor system 104 can be independent of the robotic system.

In FIG. 1, $d_e$ is emitter-to-tissue distance from the emitter 106 to the surface 105 of the tissue 103, and $d_t$ is device-to-tissue distance from a distal end of the surgical device 102 to the surface 105 of the tissue 103. The distance sensor system 104 is configured to determine the emitter-to-tissue distance $d_e$. The device-to-tissue distance $d_t$ is obtainable from the known position of the emitter 106 on the surgical device 102, e.g., on a shaft thereof proximal to the surgical device's distal end, relative to the distal end of the surgical device 102. In other words, when the distance between the emitter 106 and the distal end of the surgical device 102 is known, the device-to-tissue distance $d_t$ can be determined from the emitter-to-tissue distance $d_e$. In some embodiments, the shaft of the surgical device 102 can include one or more articulation joints and can be articulatable with respect to the emitter 106 and jaws at the distal end of the surgical device 102. The articulation configuration can include a multi-joint vertebrae-like structure, for example. In some embodiments, a three-dimensional camera can be utilized to triangulate one or more distances to the surface 105.

In FIG. 1, $d_w$ is camera-to-critical structure distance from the optical waveform emitter 123 located on the imaging device 120 to the surface of the critical structure 101, and $d_A$ is a depth of the critical structure 101 below the surface 105 of the tissue 103 (e.g., the distance between the portion of the surface 105 closest to the surgical device 102 and the critical structure 101). The time-of-flight of the optical waveforms emitted from the optical waveform emitter 123 located on the imaging device 120 are configured to determine the camera-to-critical structure distance $d_w$.

Figure 2:
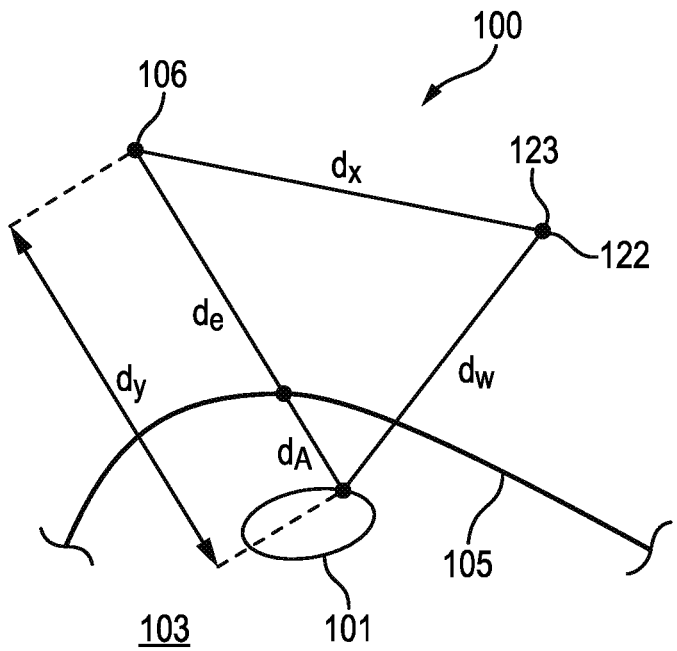
FIG. 2 is a schematic view of triangularization between a surgical device, an imaging device, and a critical structure of FIG. 1.

As shown in FIG. 2, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$. Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, the distance $d_A$ can be determined from an ultrasound, a registered magnetic resonance imaging (MRI), or computerized tomography (CT) scan. In still other instances, the distance $d_A$ can be determined with spectral imaging because the detection signal received by the imaging device 120 can vary based on the type of material, e.g., type of the tissue 103. For example, fat can decrease the detection signal in a first way, or a first amount, and collagen can decrease the detection signal in a different, second way, or a second amount.

Figure 3:
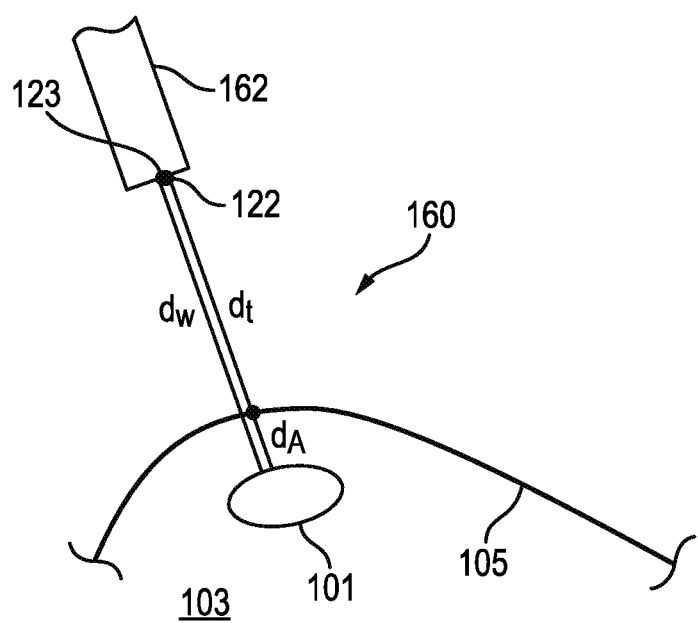
FIG. 3 is a schematic view of another embodiment of a surgical visualization system.

In another embodiment of a surgical visualization system 160 illustrated in FIG. 3, a surgical device 162, and not the imaging device 120, includes the optical waveform emitter 123 and the waveform sensor 122 that is configured to detect the reflected waveforms. The optical waveform emitter 123 is configured to emit waveforms for determining the distances $d_t$ and $d_w$ from a common device, such as the surgical device 162, as described herein. In such instances, the distance $d_A$ from the surface 105 of the tissue 103 to the surface of the critical structure 101 can be determined as follows:

$$d_A = d_w - d_t$$

Figure 4:
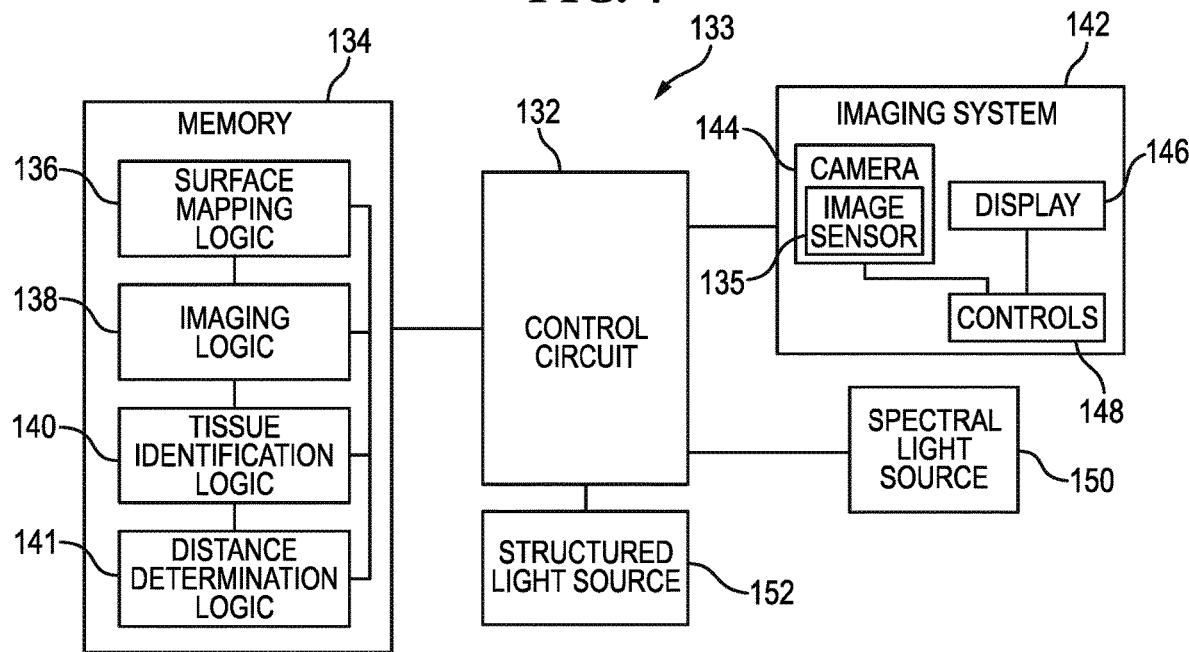
FIG. 4 is a schematic view of one embodiment of a control system for a surgical visualization system.

The surgical visualization system 100 includes a control system configured to control various aspects of the surgical visualization system 100. FIG. 4 illustrates one embodiment of a control system 133 that can be utilized as the control system of the surgical visualization system 100 (or other surgical visualization system described herein). The control system 133 includes a control circuit 132 configured to be in signal communication with a memory 134. The memory 134 is configured to store instructions executable by the control circuit 132, such as instructions to determine and/or recognize critical structures (e.g., the critical structure 101 of FIG. 1), instructions to determine and/or compute one or more distances and/or three-dimensional digital representations, and instructions to communicate information to a medical practitioner. As in this illustrated embodiment, the memory 134 can store surface mapping logic 136, imaging logic 138, tissue identification logic 140, and distance determining logic 141, although the memory 134 can store any combinations of the logics 136, 138, 140, 141 and/or can combine various logics together. The control system 133 also includes an imaging system 142 including a camera 144 (e.g., the imaging system including the imaging device 120 of FIG. 1), a display 146 (e.g., a monitor, a computer tablet screen, etc.), and controls 148 of the camera 144 and the display 146. The camera 144 includes an image sensor 135 (e.g., the waveform sensor 122) configured to receive signals from various light sources emitting light at various visible and invisible spectra (e.g., visible light, spectral imagers, three-dimensional lens, etc.). The display 146 is configured to depict real, virtual, and/or virtually-augmented images and/or information to a medical practitioner.

In an exemplary embodiment, the image sensor 135 is a solid-state electronic device containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of the image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths in a range of about 350 nm to about 1050 nm, such as in a range of about 400 nm to about 1000 nm. A person skilled in the art will appreciate that a value may not be precisely at a value but nevertheless considered to be about that value for any of a variety of reasons, such as sensitivity of measurement equipment and manufacturing tolerances. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g., Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes an emitter (e.g., the emitter 106) including a spectral light source 150 and a structured light source 152 each operably coupled to the control circuit 133. A single source can be pulsed to emit wavelengths of light in the spectral light source 150 range and wavelengths of light in the structured light source 152 range. Alternatively, a single light source can be pulsed to provide light in the invisible spectrum (e.g., infrared spectral light) and wavelengths of light on the visible spectrum. The spectral light source 150 can be, for example, a hyperspectral light source, a multispectral light source, and/or a selective spectral light source. The tissue identification logic 140 is configured to identify critical structure(s) (e.g., the critical structure 101 of FIG. 1) via data from the spectral light source 150 received by the image sensor 135 of the camera 144. The surface mapping logic 136 is configured to determine the surface contours of the visible tissue (e.g., the tissue 103) based on reflected structured light. With time-of-flight measurements, the distance determining logic 141 is configured to determine one or more distance(s) to the visible tissue and/or the critical structure. Output from each of the surface mapping logic 136, the tissue identification logic 140, and the distance determining logic 141 is configured to be provided to the imaging logic 138, and combined, blended, and/or overlaid by the imaging logic 138 to be conveyed to a medical practitioner via the display 146 of the imaging system 142.

Figure 5:
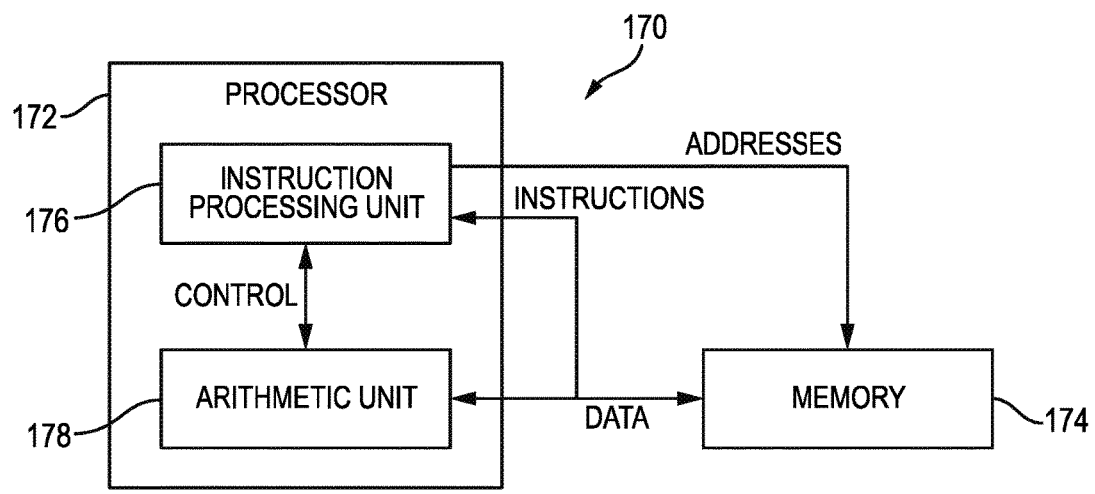
FIG. 5 is a schematic view of one embodiment of a control circuit of a control system for a surgical visualization system.

The control circuit 132 can have a variety of configurations. FIG. 5 illustrates one embodiment of a control circuit 170 that can be used as the control circuit 132 configured to control aspects of the surgical visualization system 100. The control circuit 170 is configured to implement various processes described herein. The control circuit 170 includes a microcontroller that includes a processor 172 (e.g., a microprocessor or microcontroller) operably coupled to a memory 174. The memory 174 is configured to store machine-executable instructions that, when executed by the processor 172, cause the processor 172 to execute machine instructions to implement various processes described herein. The processor 172 can be any one of a number of single-core or multicore processors known in the art. The memory 174 can include volatile and non-volatile storage media. The processor 172 includes an instruction processing unit 176 and an arithmetic unit 178. The instruction processing unit 176 is configured to receive instructions from the memory 174.

Figure 6:
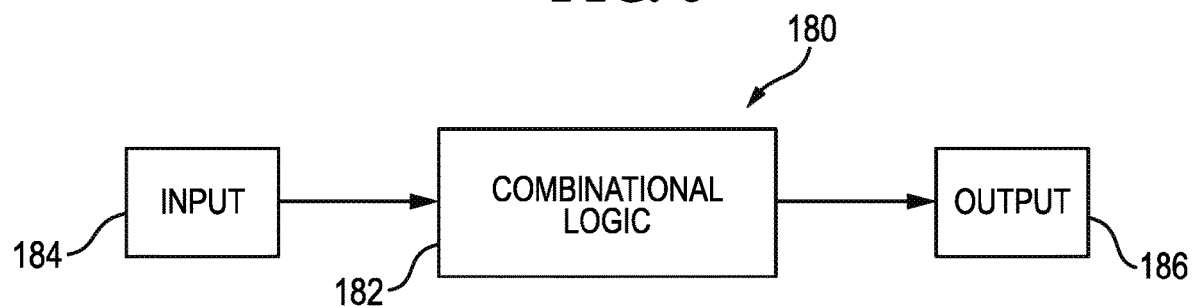
FIG. 6 is a schematic view of one embodiment of a combinational logic circuit of a surgical visualization system.

The surface mapping logic 136, the imaging logic 138, the tissue identification logic 140, and the distance determining logic 141 can have a variety of configurations. FIG. 6 illustrates one embodiment of a combinational logic circuit 180 configured to control aspects of the surgical visualization system 100 using logic such as one or more of the surface mapping logic 136, the imaging logic 138, the tissue identification logic 140, and the distance determining logic 141. The combinational logic circuit 180 includes a finite state machine that includes a combinational logic 182 configured to receive data associated with a surgical device (e.g. the surgical device 102 and/or the imaging device 120) at an input 184, process the data by the combinational logic 182, and provide an output 184 to a control circuit (e.g., the control circuit 132).

Figure 7:
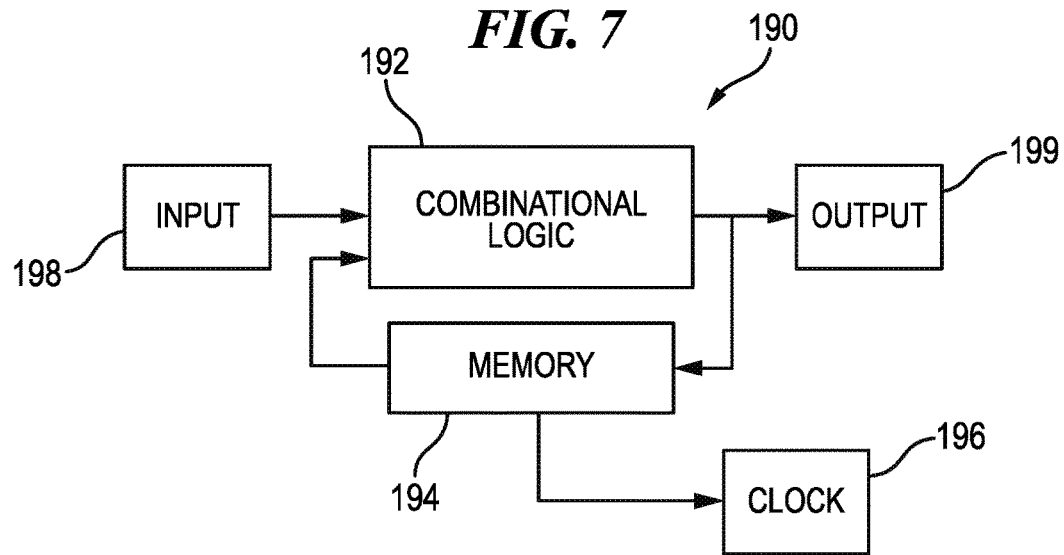
FIG. 7 is a schematic view of one embodiment of a sequential logic circuit of a surgical visualization system.

FIG. 7 illustrates one embodiment of a sequential logic circuit 190 configured to control aspects of the surgical visualization system 100 using logic such as one or more of the surface mapping logic 136, the imaging logic 138, the tissue identification logic 140, and the distance determining logic 141. The sequential logic circuit 190 includes a finite state machine that includes a combinational logic 192, a memory 194, and a clock 196. The memory 194 is configured to store a current state of the finite state machine. The sequential logic circuit 190 can be synchronous or asynchronous. The combinational logic 192 is configured to receive data associated with a surgical device (e.g. the surgical device 102 and/or the imaging device 120) at an input 426, process the data by the combinational logic 192, and provide an output 499 to a control circuit (e.g., the control circuit 132). In some embodiments, the sequential logic circuit 190 can include a combination of a processor (e.g., processor 172 of FIG. 5) and a finite state machine to implement various processes herein. In some embodiments, the finite state machine can include a combination of a combinational logic circuit (e.g., the combinational logic circuit 192 of FIG. 7) and the sequential logic circuit 190.

Figure 8:
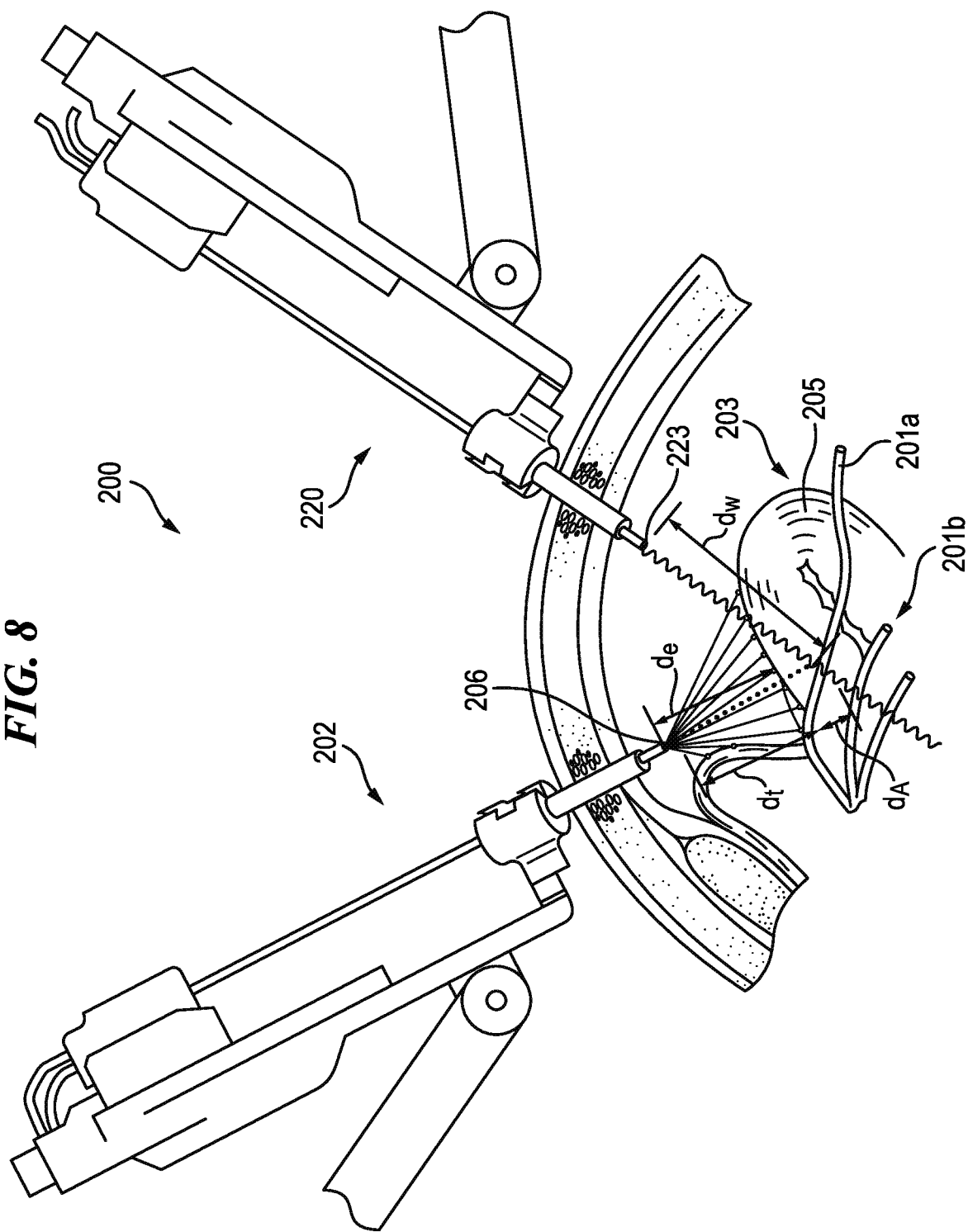
FIG. 8 is a schematic view of yet another embodiment of a surgical visualization system.

FIG. 8 illustrates another embodiment of a surgical visualization system 200. The surgical visualization system 200 is generally configured and used similar to the surgical visualization system 100 of FIG. 1, e.g., includes a surgical device 202 and an imaging device 220. The imaging device 220 includes a spectral light emitter 223 configured to emit spectral light in a plurality of wavelengths to obtain a spectral image of hidden structures, for example. The imaging device 220 can also include a three-dimensional camera and associated electronic processing circuits. The surgical visualization system 200 is shown being utilized intraoperatively to identify and facilitate avoidance of certain critical structures, such as a ureter 201a and vessels 201b, in an organ 203 (a uterus in this embodiment) that are not visible on a surface 205 of the organ 203.

The surgical visualization system 200 is configured to determine an emitter-to-tissue distance $d_e$ from an emitter 206 on the surgical device 202 to the surface 205 of the uterus 203 via structured light. The surgical visualization system 200 is configured to extrapolate a device-to-tissue distance $d_t$ from the surgical device 202 to the surface 205 of the uterus 203 based on the emitter-to-tissue distance $d_e$. The surgical visualization system 200 is also configured to determine a tissue-to-ureter distance $d_A$ from the ureter 201a to the surface 205 and a camera-to-ureter distance $d_w$ from the imaging device 220 to the ureter 201a. As described herein, e.g., with respect to the surgical visualization system 100 of FIG. 1, the surgical visualization system 200 is configured to determine the distance $d_w$ with spectral imaging and time-of-flight sensors, for example. In various embodiments, the surgical visualization system 200 can determine (e.g. triangulate) the tissue-to-ureter distance $d_A$ (or depth) based on other distances and/or the surface mapping logic described herein.

Figure 9:
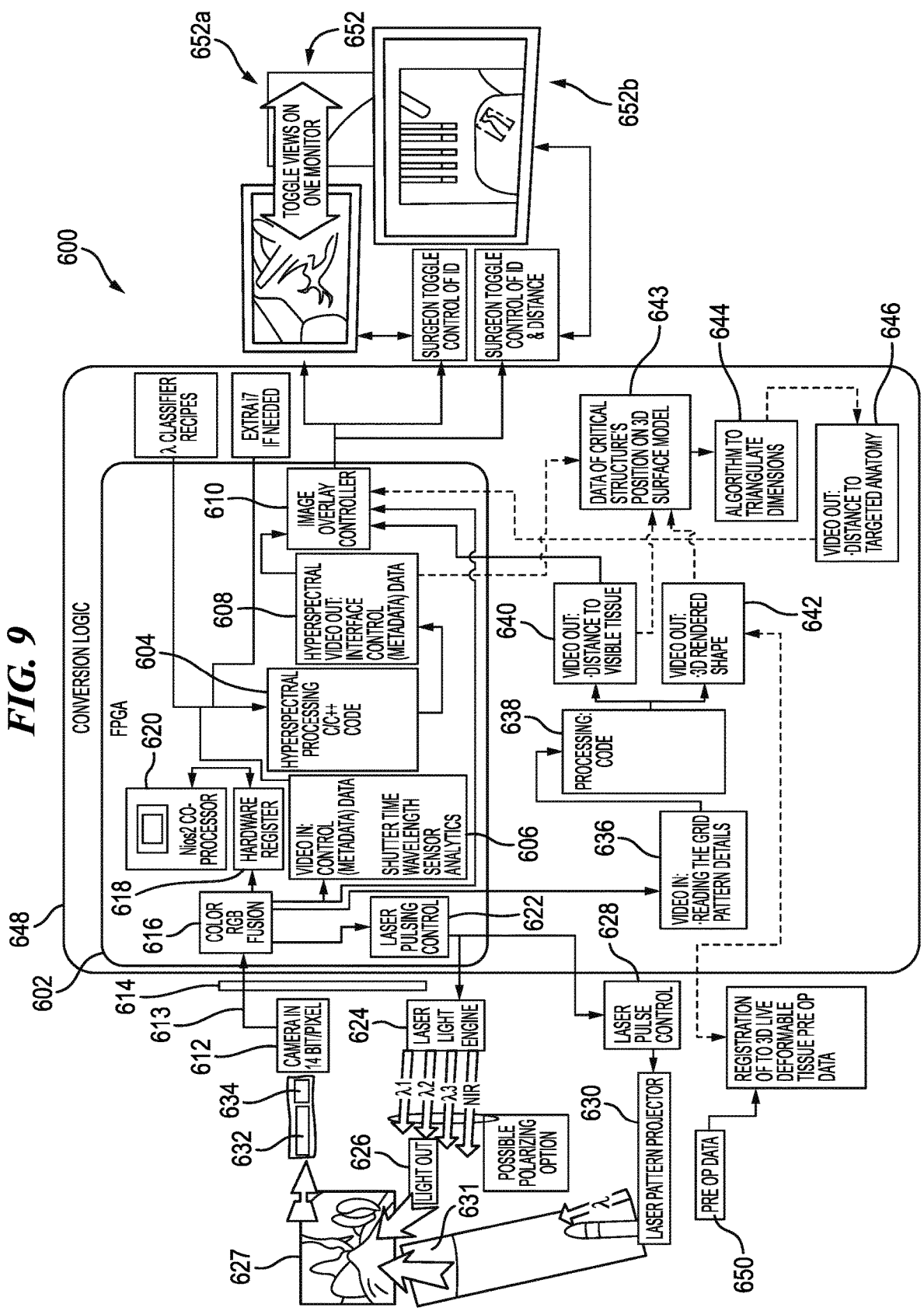
FIG. 9 is a schematic view of another embodiment of a control system for a surgical visualization system.

As mentioned above, a surgical visualization system includes a control system configured to control various aspects of the surgical visualization system. The control system can have a variety of configurations. FIG. 9 illustrates one embodiment of a control system 600 for a surgical visualization system, such as the surgical visualization system 100 of FIG. 1, the surgical visualization system 200 of FIG. 8, or other surgical visualization system described herein. The control system 600 is a conversion system that integrates spectral signature tissue identification and structured light tissue positioning to identify a critical structure, especially when those structure(s) are obscured by tissue, e.g., by fat, connective tissue, blood tissue, and/or organ(s), and/or by blood, and/or to detect tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 configured to convert tissue data to usable information for surgeons and/or other medical practitioners. For example, variable reflectance based on wavelengths with respect to obscuring material can be utilized to identify the critical structure in the anatomy. Moreover, the control system 600 is configured to combine the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various embodiments, the control system 600 is configured to provide warnings to a medical practitioner when in the proximity of one or more critical structures. Various algorithms can be employed to guide robotic automation and semi-automated approaches based on the surgical procedure and proximity to the critical structure(s).

A projected array of lights is employed by the control system 600 to determine tissue shape and motion intraoperatively. Alternatively, flash Lidar may be utilized for surface mapping of the tissue.

The control system 600 is configured to detect the critical structure, which as mentioned above can include one or more critical structures, and provide an image overlay of the critical structure and measure the distance to the surface of the visible tissue and the distance to the embedded/buried critical structure(s). The control system 600 can measure the distance to the surface of the visible tissue or detect the critical structure and provide an image overlay of the critical structure.

The control system 600 includes a spectral control circuit 602. The spectral control circuit 602 can be a field programmable gate array (FPGA) or another suitable circuit configuration, such as the configurations described with respect to FIG. 6, FIG. 7, and FIG. 8. The spectral control circuit 602 includes a processor 604 configured to receive video input signals from a video input processor 606. The processor 604 can be configured for hyperspectral processing and can utilize C/C++ code, for example. The video input processor 606 is configured to receive video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 is configured to provides the video output signal to an image overlay controller 610.

The video input processor 606 is operatively coupled to a camera 612 at the patient side via a patient isolation circuit 614. The camera 612 includes a solid state image sensor 634. The patient isolation circuit 614 can include a plurality of transformers so that the patient is isolated from other circuits in the system. The camera 612 is configured to receive intraoperative images through optics 632 and the image sensor 634. The image sensor 634 can include a CMOS image sensor, for example, or can include another image sensor technology, such as those discussed herein in connection with FIG. 4. The camera 612 is configured to output 613 images in 14 bit/pixel signals. A person skilled in the art will appreciate that higher or lower pixel resolutions can be employed. The isolated camera output signal 613 is provided to a color RGB fusion circuit 616, which in this illustrated embodiment employs a hardware register 618 and a Nios2 co-processor 620 configured to process the camera output signal 613. A color RGB fusion output signal is provided to the video input processor 606 and a laser pulsing control circuit 622.

The laser pulsing control circuit 622 is configured to control a laser light engine 624. The laser light engine 624 is configured to output light in a plurality of wavelengths ($\lambda 1$, $\lambda 2$, $\lambda 3$ ... $\lambda n$) including near infrared (NIR). The laser light engine 624 can operate in a plurality of modes. For example, the laser light engine 624 can operate in two modes. In a first mode, e.g., a normal operating mode, the laser light engine 624 is configured to output an illuminating signal. In a second mode, e.g., an identification mode, the laser light engine 624 is configured to output RGBG and NIR light. In various embodiments, the laser light engine 624 can operate in a polarizing mode.

Light output 626 from the laser light engine 624 is configured to illuminate targeted anatomy in an intraoperative surgical site 627. The laser pulsing control circuit 622 is also configured to control a laser pulse controller 628 for a laser pattern projector 630 configured to project a laser light pattern 631, such as a grid or pattern of lines and/or dots, at a predetermined wavelength ($\lambda 2$) on an operative tissue or organ at the surgical site 627. The camera 612 is configured to receive the patterned light as well as the reflected light output through the camera optics 632. The image sensor 634 is configured to convert the received light into a digital signal.

The color RGB fusion circuit 616 is also configured to output signals to the image overlay controller 610 and a video input module 636 for reading the laser light pattern 631 projected onto the targeted anatomy at the surgical site 627 by the laser pattern projector 630. A processing module 638 is configured to process the laser light pattern 631 and output a first video output signal 640 representative of the distance to the visible tissue at the surgical site 627. The data is provided to the image overlay controller 610. The processing module 638 is also configured to output a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 is configured to determine the distance (e.g., distance $d_A$ of FIG. 1) to a buried critical structure (e.g., via triangularization algorithms 644), and the distance to the buried critical structure can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650, such as from a CT or MRI scan, can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Embodiments of registration of preoperative data are further described in U.S. Pat. Pub. No. 2020/0015907 entitled "Integration Of Imaging Data" filed Sep. 11, 2018, which is hereby incorporated by reference herein in its entirety.

The video monitors 652 are configured to output the integrated/augmented views from the image overlay controller 610. A medical practitioner can select and/or toggle between different views on one or more displays. On a first display 652a, which is a monitor in this illustrated embodiment, the medical practitioner can toggle between (A) a view in which a three-dimensional rendering of the visible tissue is depicted and (B) an augmented view in which one or more hidden critical structures are depicted over the three-dimensional rendering of the visible tissue. On a second display 652b, which is a monitor in this illustrated embodiment, the medical practitioner can toggle on distance measurements to one or more hidden critical structures and/or the surface of visible tissue, for example.

The various surgical visualization systems described herein can be utilized to visualize various different types of tissues and/or anatomical structures, including tissues and/or anatomical structures that may be obscured from being visualized by EMR in the visible portion of the spectrum. The surgical visualization system can utilize a spectral imaging system, as mentioned above, which can be configured to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be configured to characterize the tissue type of the tissue being visualized based upon the particular combination of constituent materials.

Figure 10:
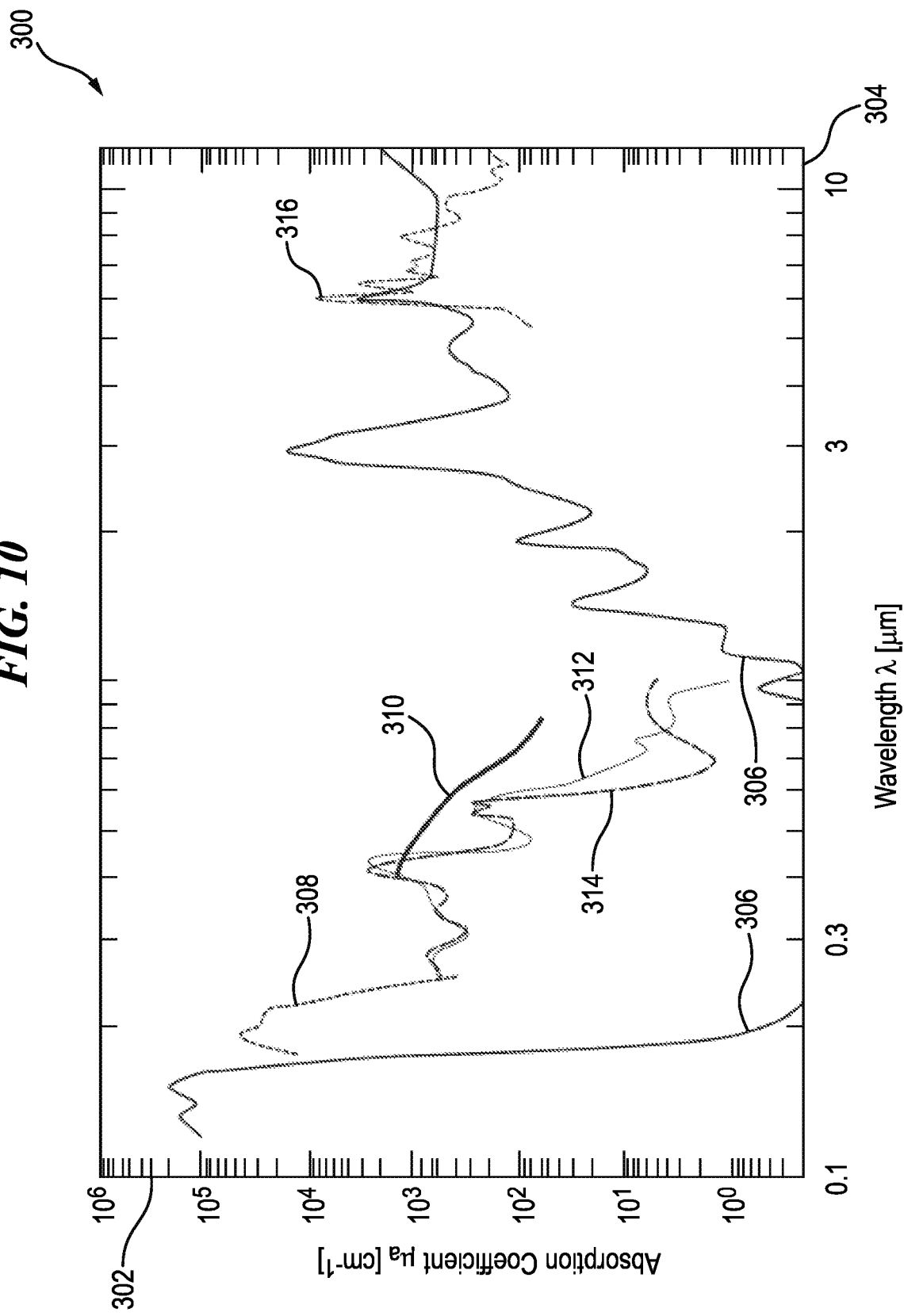
FIG. 10 is a graph showing wavelength versus absorption coefficient for various biological materials.

FIG. 10 shows a graph 300 depicting how the absorption coefficient of various biological materials varies across the EMR wavelength spectrum. In the graph 300, the vertical axis 302 represents absorption coefficient of the biological material in $cm^{-1}$, and the horizontal axis 304 represents EMR wavelength in $\mu m$. A first line 306 in the graph 300 represents the absorption coefficient of water at various EMR wavelengths, a second line 308 represents the absorption coefficient of protein at various EMR wavelengths, a third line 310 represents the absorption coefficient of melanin at various EMR wavelengths, a fourth line 312 represents the absorption coefficient of deoxygenated hemoglobin at various EMR wavelengths, a fifth line 314 represents the absorption coefficient of oxygenated hemoglobin at various EMR wavelengths, and a sixth line 316 represents the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system of a surgical visualization system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 11:
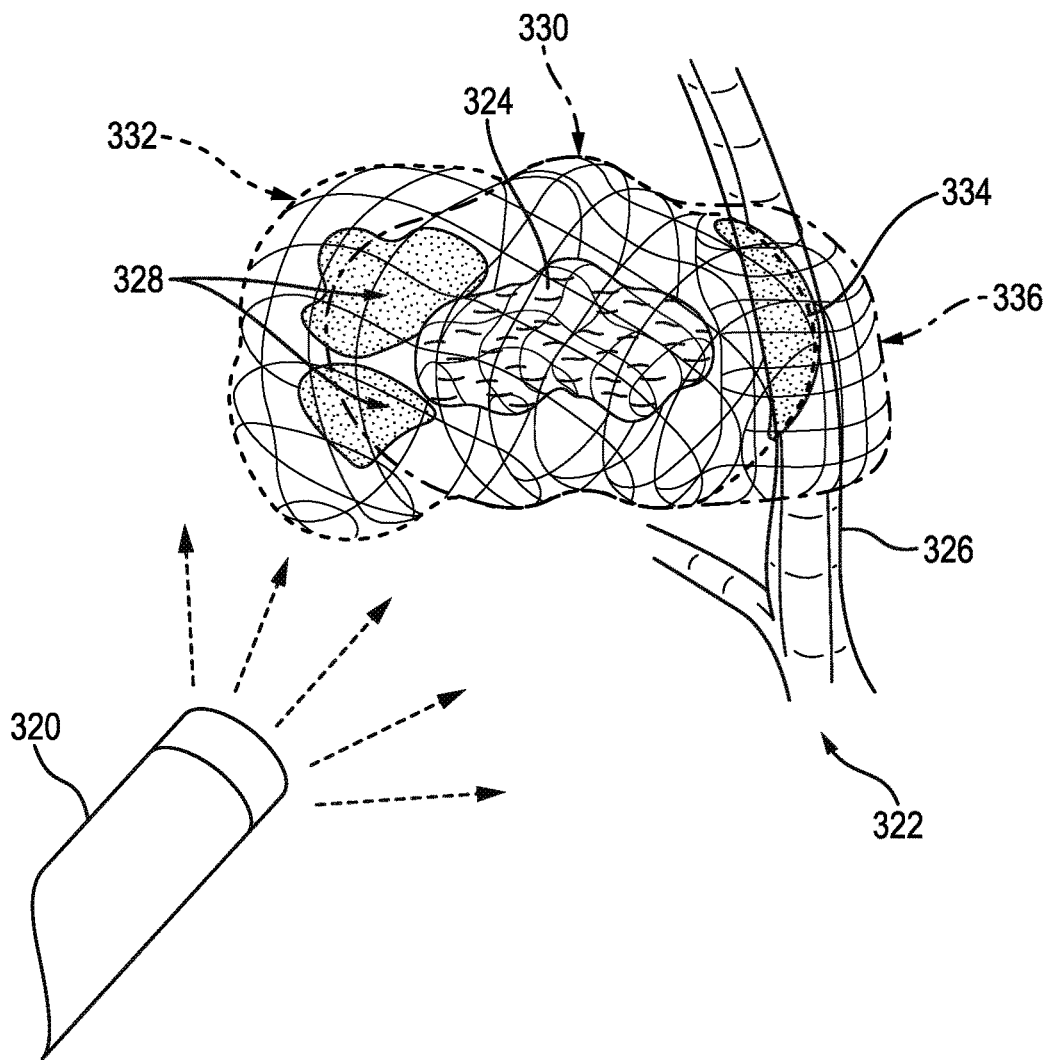
FIG. 11 is a schematic view of one embodiment of a spectral emitter visualizing a surgical site.

FIG. 11 shows an embodiment of the utilization of spectral imaging techniques to visualize different tissue types and/or anatomical structures. In FIG. 11, a spectral emitter 320 (e.g., the spectral light source 150 of FIG. 4) is being utilized by an imaging system to visualize a surgical site 322. The EMR emitted by the spectral emitter 320 and reflected from the tissues and/or structures at the surgical site 322 is received by an image sensor (e.g., the image sensor 135 of FIG. 4) to visualize the tissues and/or structures, which can be either visible (e.g., be located at a surface of the surgical site 322) or obscured (e.g., underlay other tissue and/or structures at the surgical site 322). In this embodiment, an imaging system (e.g., the imaging system 142 of FIG. 4) visualizes a tumor 324, an artery 326, and various abnormalities 328 (e.g., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system (e.g., the display 146 of the imaging system 142 of FIG. 4), on a primary display (e.g., the primary display 819 of FIG. 19), on a non-sterile display (e.g., the non-sterile displays 807, 809 of FIG. 19), on a display of a surgical hub (e.g., the display of the surgical hub 806 of FIG. 19), on a device/instrument display, and/or on another display.

The imaging system can be configured to tailor or update the displayed surgical site visualization according to the identified tissue and/or structure types. For example, as shown in FIG. 11, the imaging system can display a margin 330 associated with the tumor 324 being visualized on a display screen associated with or coupled to the imaging system, on a primary display, on a non-sterile display, on a display of a surgical hub, on a device/instrument display, and/or on another display. The margin 330 can indicate the area or amount of tissue that should be excised to ensure complete removal of the tumor 324. The surgical visualization system's control system (e.g., the control system 133 of FIG. 4) can be configured to control or update the dimensions of the margin 330 based on the tissues and/or structures identified by the imaging system. In this illustrated embodiment, the imaging system has identified multiple abnormalities 328 within the field of view (FOV). Accordingly, the control system can adjust the displayed margin 330 to a first updated margin 332 having sufficient dimensions to encompass the abnormalities 328. Further, the imaging system has also identified the artery 326 partially overlapping with the initially displayed margin 330 (as indicated by a highlighted region 334 of the artery 326). Accordingly, the control system can adjust the displayed margin to a second updated margin 336 having sufficient dimensions to encompass the relevant portion of the artery 326.

Figure 12:
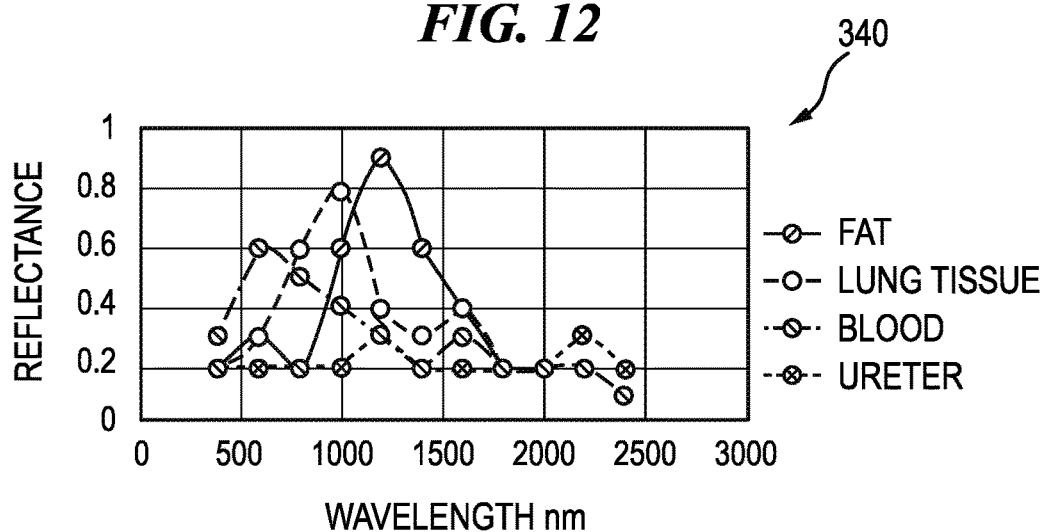
FIG. 12 is a graph depicting illustrative hyperspectral identifying signatures to differentiate a ureter from obscurants.
Figure 13:
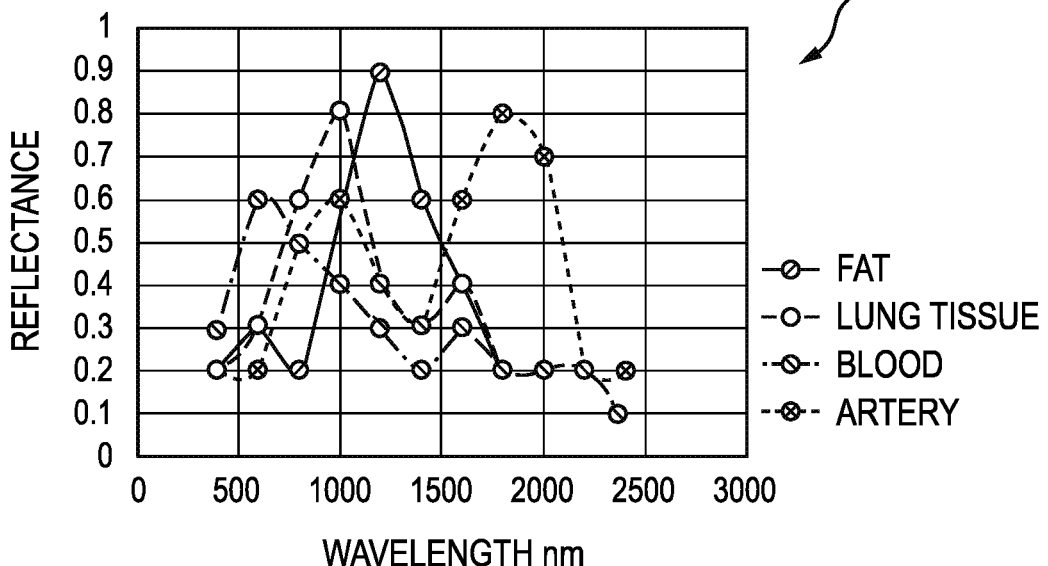
FIG. 13 is a graph depicting illustrative hyperspectral identifying signatures to differentiate an artery from obscurants.
Figure 14:
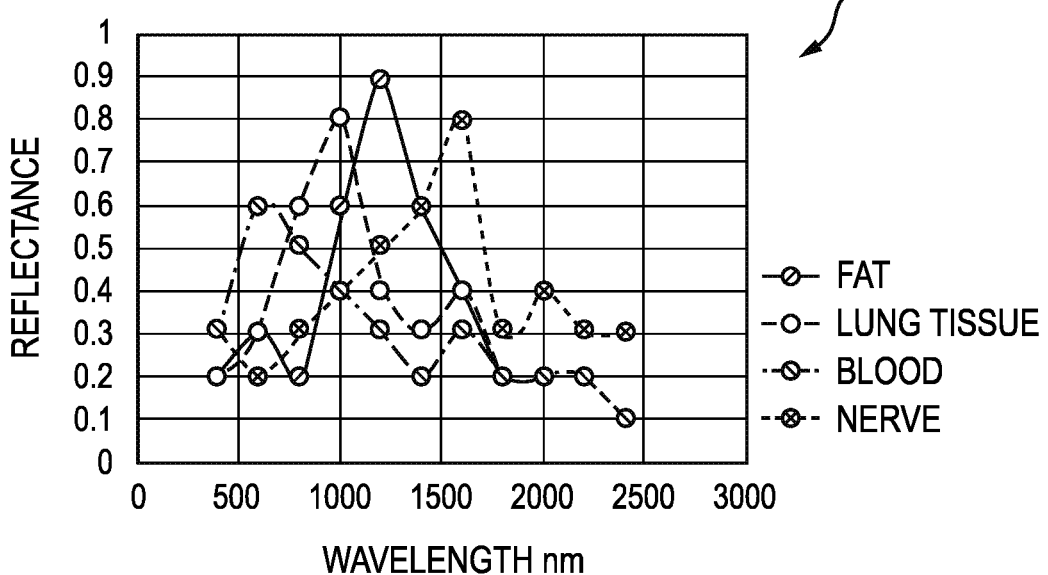
FIG. 14 is a graph depicting illustrative hyperspectral identifying signatures to differentiate a nerve from obscurants.

Tissues and/or structures can also be imaged or characterized according to their reflective characteristics, in addition to or in lieu of their absorptive characteristics described above with respect to FIG. 10 and FIG. 11, across the EMR wavelength spectrum. For example, FIG. 12, FIG. 13, and FIG. 14 illustrate various graphs of reflectance of different types of tissues or structures across different EMR wavelengths. FIG. 12 is a graphical representation 340 of an illustrative ureter signature versus obscurants. FIG. 13 is a graphical representation 342 of an illustrative artery signature versus obscurants. FIG. 14 is a graphical representation 344 of an illustrative nerve signature versus obscurants. The plots in FIG. 12, FIG. 13, and FIG. 14 represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

Select wavelengths for spectral imaging can be identified and utilized based on the anticipated critical structures and/or obscurants at a surgical site (e.g., "selective spectral" imaging). By utilizing selective spectral imaging, the amount of time required to obtain the spectral image can be minimized such that the information can be obtained in real-time and utilized intraoperatively. The wavelengths can be selected by a medical practitioner or by a control circuit based on input by a user, e.g., a medical practitioner. In certain instances, the wavelengths can be selected based on machine learning and/or big data accessible to the control circuit via, e.g., a cloud or surgical hub.

Figure 15:
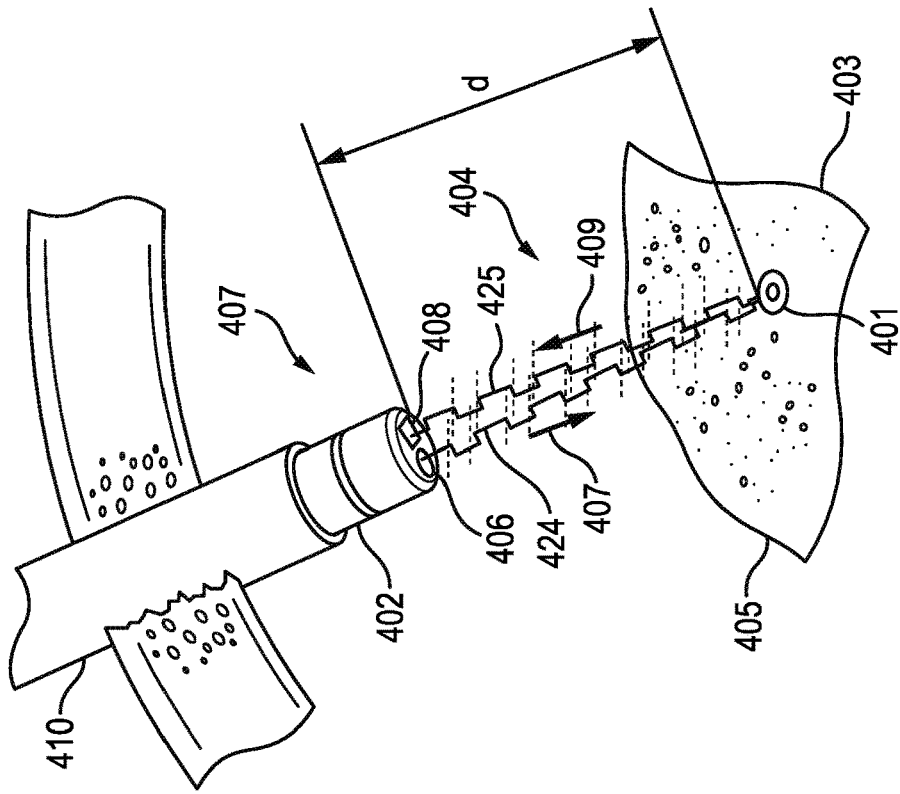
FIG. 15 is a schematic view of one embodiment of a near infrared (NIR) time-of-flight measurement system being utilized intraoperatively.

FIG. 15 illustrates one embodiment of spectral imaging to tissue being utilized intraoperatively to measure a distance between a waveform emitter and a critical structure that is obscured by tissue. FIG. 15 shows an embodiment of a time-of-flight sensor system 404 utilizing waveforms 424, 425. The time-of-flight sensor system 404 can be incorporated into a surgical visualization system, e.g., as the sensor system 104 of the surgical visualization system 100 of FIG. 1. The time-of-flight sensor system 404 includes a waveform emitter 406 and a waveform receiver 408 on the same surgical device 402 (e.g., the emitter 106 and the receiver 108 on the same surgical device 102 of FIG. 1). The emitted wave 400 extends to a critical structure 401 (e.g., the critical structure 101 of FIG. 1) from the emitter 406, and the received wave 425 is reflected back to by the receiver 408 from the critical structure 401. The surgical device 402 in this illustrated embodiment is positioned through a trocar 410 that extends into a cavity 407 in a patient. Although the trocar 410 is used in this in this illustrated embodiment, other trocars or other access devices can be used, or no access device may be used.

Figure 16:
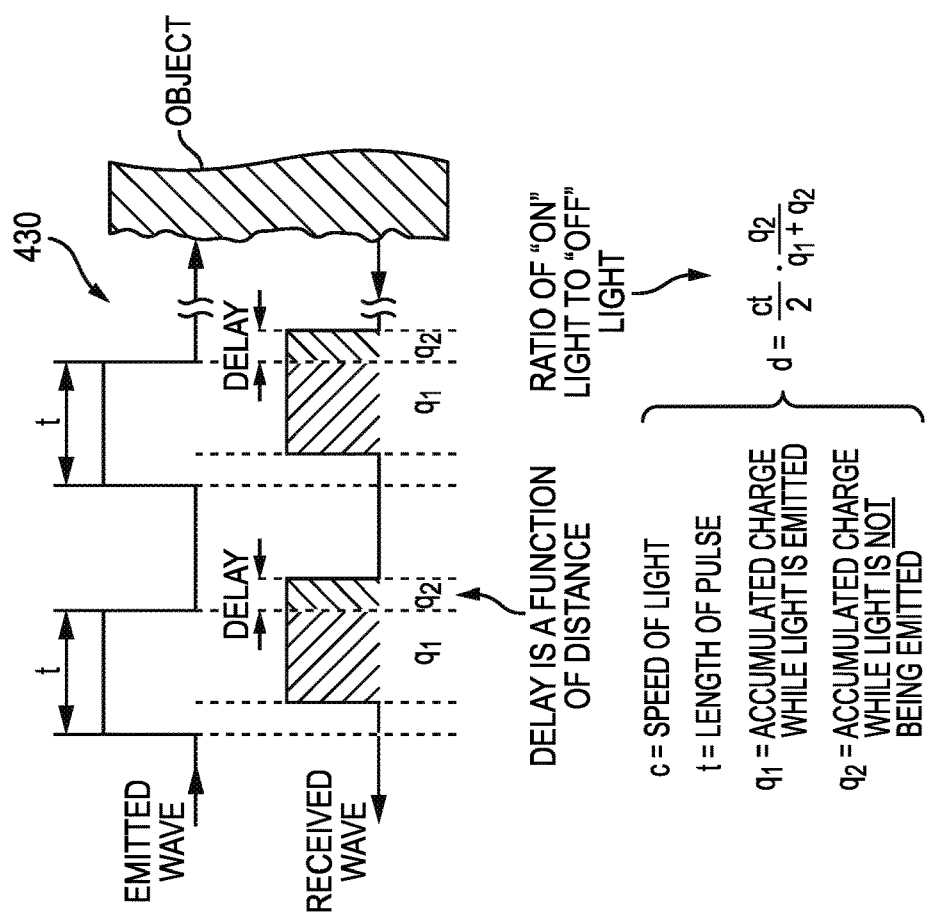
FIG. 16 shows a time-of-flight timing diagram for the system of FIG. 15.

The waveforms 424, 425 are configured to penetrate obscuring tissue 403, such as by having wavelengths in the NIR or SWIR spectrum of wavelengths. A spectral signal (e.g., hyperspectral, multispectral, or selective spectral) or a photoacoustic signal is emitted from the emitter 406, as shown by a first arrow 407 pointing distally, and can penetrate the tissue 403 in which the critical structure 401 is concealed. The emitted waveform 424 is reflected by the critical structure 401, as shown by a second arrow 409 pointing proximally. The received waveform 425 can be delayed due to a distance d between a distal end of the surgical device 402 and the critical structure 401. The waveforms 424, 425 can be selected to target the critical structure 401 within the tissue 403 based on the spectral signature of the critical structure 401, as described herein. The emitter 406 is configured to provide a binary signal on and off, as shown in FIG. 16, for example, which can be measured by the receiver 408.

Based on the delay between the emitted wave 424 and the received wave 425, the time-of-flight sensor system 404 is configured to determine the distance d. A time-of-flight timing diagram 430 for the emitter 406 and the receiver 408 of FIG. 15 is shown in FIG. 16. The delay is a function of the distance d and the distance d is given by:

$$d = \frac{ct}{2} \cdot \frac{q_2}{q_1 + q_2}$$

$$\left[\left[d = \frac{Ct}{2} \cdot \frac{\overline{q_2}}{q_1 + q_2}\right]\right]$$

where c=the speed of light; t=length of pulse; q1=accumulated charge while light is emitted; and q2=accumulated charge while light is not being emitted.

The time-of-flight of the waveforms 424, 425 corresponds to the distance d in FIG. 15. In various instances, additional emitters/receivers and/or pulsing signals from the emitter 406 can be configured to emit a non-penetrating signal. The non-penetrating signal can be configured to determine the distance from the emitter 406 to the surface 405 of the obscuring tissue 403. In various instances, a depth of the critical structure 401 can be determined by:

$$d_A = d_w - d_t$$

where $d_A$=the depth of the critical structure 401; $d_w$=the distance from the emitter 406 to the critical structure 401 (d in FIG. 15); and $d_t$=the distance from the emitter 406 (on the distal end of the surgical device 402) to the surface 405 of the obscuring tissue 403.

Figure 17:
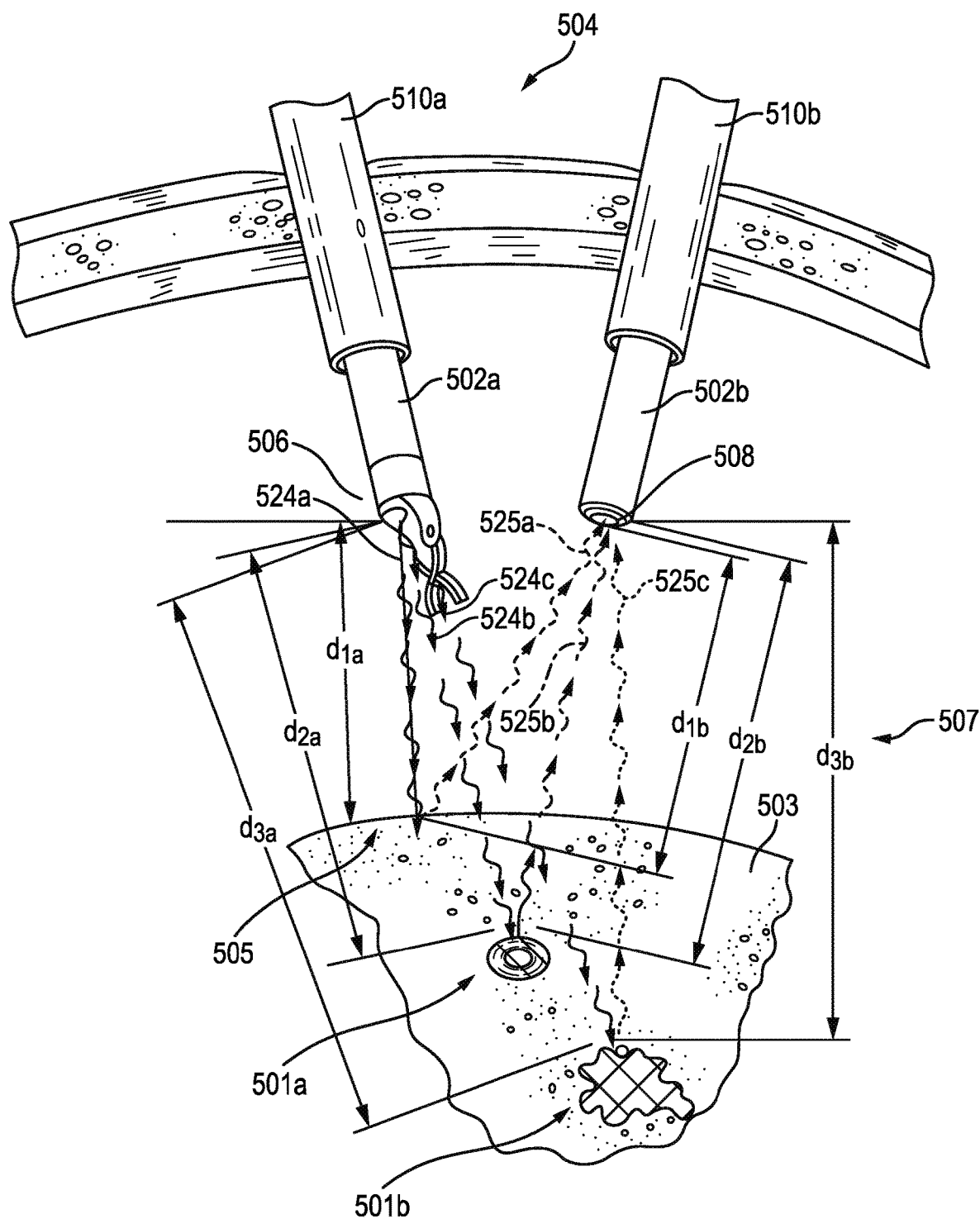
FIG. 17 is a schematic view of another embodiment of a near infrared (NIR) time-of-flight measurement system being utilized intraoperatively.

FIG. 17 illustrates another embodiment of a time-of-flight sensor system 504 utilizing waves 524a, 524b, 524c, 525a, 525b, 525c is shown. The time-of-flight sensor system 504 can be incorporated into a surgical visualization system, e.g., as the sensor system 104 of the surgical visualization system 100 of FIG. 1. The time-of-flight sensor system 504 includes a waveform emitter 506 and a waveform receiver 508 (e.g., the emitter 106 and the receiver 108 of FIG. 1). The waveform emitter 506 is positioned on a first surgical device 502a (e.g., the surgical device 102 of FIG. 1), and the waveform receiver 508 is positioned on a second surgical device 502b. The surgical devices 502a, 502b are positioned through first and second trocars 510a, 510b, respectively, which extend into a cavity 507 in a patient. Although the trocars 510a, 510b are used in this in this illustrated embodiment, other trocars or other access devices can be used, or no access device may be used. The emitted waves 524a, 524b, 524c extend toward a surgical site from the emitter 506, and the received waves 525a, 525b, 525c are reflected back to the receiver 508 from various structures and/or surfaces at the surgical site.

The different emitted waves 524a, 524b, 524c are configured to target different types of material at the surgical site. For example, the wave 524a targets obscuring tissue 503, the wave 524b targets a first critical structure 501a (e.g., the critical structure 101 of FIG. 1), which is a vessel in this illustrated embodiment, and the wave 524c targets a second critical structure 501b (e.g., the critical structure 101 of FIG. 1), which is a cancerous tumor in this illustrated embodiment. The wavelengths of the waves 524a, 524b, 524c can be in the visible light, NIR, or SWIR spectrum of wavelengths. For example, visible light can be reflected off a surface 505 of the tissue 503, and NIR and/or SWIR waveforms can penetrate the surface 505 of the tissue 503. In various aspects, as described herein, a spectral signal (e.g., hyperspectral, multispectral, or selective spectral) or a photoacoustic signal can be emitted from the emitter 506. The waves 524b, 524c can be selected to target the critical structures 501a, 501b within the tissue 503 based on the spectral signature of the critical structure 501a, 501b, as described herein. Photoacoustic imaging is further described in various U.S. patent applications, which are incorporated by reference herein in the present disclosure.

The emitted waves 524a, 524b, 524c are reflected off the targeted material, namely the surface 505, the first critical structure 501a, and the second structure 501b, respectively. The received waveforms 525a, 525b, 525c can be delayed due to distances $d_{1a}$, $d_{2a}$, $d_{3a}$, $d_{1b}$, $d_{2b}$, $d_{2c}$.

In the time-of-flight sensor system 504, in which the emitter 506 and the receiver 508 are independently positionable (e.g., on separate surgical devices 502a, 502b and/or controlled by separate robotic arms), the various distances $d_{1a}$, $d_{2a}$, $d_{3a}$, $d_{1b}$, $d_{2b}$, $d_{2c}$ can be calculated from the known position of the emitter 506 and the receiver 508. For example, the positions can be known when the surgical devices 502a, 502b are robotically-controlled. Knowledge of the positions of the emitter 506 and the receiver 508, as well as the time of the photon stream to target a certain tissue and the information received by the receiver 508 of that particular response can allow a determination of the distances $d_{1a}$, $d_{2a}$, $d_{3a}$, $d_{1b}$, $d_{2b}$, $d_{2c}$. In one aspect, the distance to the obscured critical structures 501a, 501b can be triangulated using penetrating wavelengths. Because the speed of light is constant for any wavelength of visible or invisible light, the time-of-flight sensor system 504 can determine the various distances.

In a view provided to the medical practitioner, such as on a display, the receiver 508 can be rotated such that a center of mass of the target structure in the resulting images remains constant, e.g., in a plane perpendicular to an axis of a select target structure 503, 501a, or 501b. Such an orientation can quickly communicate one or more relevant distances and/or perspectives with respect to the target structure. For example, as shown in FIG. 17, the surgical site is displayed from a viewpoint in which the critical structure 501a is perpendicular to the viewing plane (e.g., the vessel is oriented in/out of the page). Such an orientation can be default setting; however, the view can be rotated or otherwise adjusted by a medical practitioner. In certain instances, the medical practitioner can toggle between different surfaces and/or target structures that define the viewpoint of the surgical site provided by the imaging system.

As in this illustrated embodiment, the receiver 508 can be mounted on the trocar 510b (or other access device) through which the surgical device 502b is positioned. In other embodiments, the receiver 508 can be mounted on a separate robotic arm for which the three-dimensional position is known. In various instances, the receiver 508 can be mounted on a movable arm that is separate from a robotic surgical system that controls the surgical device 502a or can be mounted to an operating room (OR) table or fixture that is intraoperatively registerable to the robot coordinate plane. In such instances, the position of the emitter 506 and the receiver 508 can be registerable to the same coordinate plane such that the distances can be triangulated from outputs from the time-of-flight sensor system 504.

Combining time-of-flight sensor systems and near-infrared spectroscopy (NIRS), termed TOF-NIRS, which is capable of measuring the time-resolved profiles of NIR light with nanosecond resolution can be found in "Time-Of-Flight Near-Infrared Spectroscopy For Nondestructive Measurement Of Internal Quality In Grapefruit," Journal of the American Society for Horticultural Science, May 2013 vol. 138 no. 3 225-228, which is hereby incorporated by reference in its entirety.

Embodiments of visualization systems and aspects and uses thereof are described further in U.S. Pat. Pub. No. 2020/0015923 entitled "Surgical Visualization Platform" filed Sep. 11, 2018, U.S. Pat. Pub. No. 2020/0015900 entitled "Controlling An Emitter Assembly Pulse Sequence" filed Sep. 11, 2018, U.S. Pat. Pub. No. 2020/0015668 entitled "Singular EMR Source Emitter Assembly" filed Sep. 11, 2018, U.S. Pat. Pub. No. 2020/0015925 entitled "Combination Emitter And Camera Assembly" filed Sep. 11, 2018, U.S. Pat. Pub. No. 2020/00015899 entitled "Surgical Visualization With Proximity Tracking Features" filed Sep. 11, 2018, U.S. Pat. Pub. No. 2020/00015903 entitled "Surgical Visualization Of Multiple Targets" filed Sep. 11, 2018, U.S. Pat. No. 10,792,034 entitled "Visualization Of Surgical Devices" filed Sep. 11, 2018, U.S. Pat. Pub. No. 2020/0015897 entitled "Operative Communication Of Light" filed Sep. 11, 2018, U.S. Pat. Pub. No. 2020/0015924 entitled "Robotic Light Projection Tools" filed Sep. 11, 2018, U.S. Pat. Pub. No. 2020/0015898 entitled "Surgical Visualization Feedback System" filed Sep. 11, 2018, U.S. Pat. Pub. No. 2020/0015906 entitled "Surgical Visualization And Monitoring" filed Sep. 11, 2018, U.S. Pat. Pub. No. 2020/0015907 entitled "Integration Of Imaging Data" filed Sep. 11, 2018, U.S. Pat. No. 10,925,598 entitled "Robotically-Assisted Surgical Suturing Systems" filed Sep. 11, 2018, U.S. Pat. Pub. No. 2020/0015901 entitled "Safety Logic For Surgical Suturing Systems" filed Sep. 11, 2018, U.S. Pat. Pub. No. 2020/0015914 entitled "Robotic Systems With Separate Photoacoustic Receivers" filed Sep. 11, 2018, U.S. Pat. Pub. No. 2020/0015902 entitled "Force Sensor Through Structured Light Deflection" filed Sep. 11, 2018, U.S. Pat. Pub. No. 2019/0201136 entitled "Method Of Hub Communication" filed Dec. 4, 2018, U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, U.S. patent application Ser. No. 16/729,807 entitled "Method Of Using Imaging Devices In Surgery" filed Dec. 30, 2019, U.S. Prov. Pat. App. No. 63/249,652 entitled "Surgical Devices, Systems, and Methods Using Fiducial Identification and Tracking" filed on Sep. 29, 2021, U.S. Prov. Pat. App. No. 63/249,658 entitled "Surgical Devices, Systems, and Methods for Control of One Visualization with Another" filed on Sep. 29, 2021, U.S. Prov. Pat. App. No. 63/249,870 entitled "Methods and Systems for Controlling Cooperative Surgical Instruments" filed on Sep. 29, 2021, U.S. Prov. Pat. App. No. 63/249,881 entitled "Methods and Systems for Controlling Cooperative Surgical Instruments with Variable Surgical Site Access Trajectories" filed on Sep. 29, 2021, U.S. Prov. Pat. App. No. 63/249,877 entitled "Methods and Systems for Controlling Cooperative Surgical Instruments" filed on Sep. 29, 2021, and U.S. Prov. Pat. App. No. 63/249,980 entitled "Cooperative Access" filed on Sep. 29, 2021, which are hereby incorporated by reference in their entireties.

Surgical Hubs

The various visualization or imaging systems described herein can be incorporated into a system that includes a surgical hub. In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more visualization systems that are used during performance of medical procedures. The surgical hubs provide a wide array of functionality to improve the outcomes of medical procedures. The data generated by the various surgical devices, visualization systems, and surgical hubs about the patient and the medical procedure may be transmitted to the cloud-based medical analytics system. This data may then be aggregated with similar data gathered from many other surgical hubs, visualization systems, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, visualization systems, and surgical instruments. Due to the interconnectedness of all of the aforementioned components, improvements in medical procedures and practices may be found that otherwise may not be found if the many components were not so interconnected.

Examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018, U.S. Pat. Pub. No. 2019/0200981 entitled "Method Of Compressing Tissue Within A Stapling Device And Simultaneously Displaying The Location Of The Tissue Within The Jaws" filed Dec. 4, 2018, U.S. Pat. Pub. No. 2019/0201046 entitled "Method For Controlling Smart Energy Devices" filed Dec. 4, 2018, U.S. Pat. Pub. No. 2019/0201114 entitled "Adaptive Control Program Updates For Surgical Hubs" filed Mar. 29, 2018, U.S. Pat. Pub. No. 2019/0201140 entitled "Surgical Hub Situational Awareness" filed Mar. 29, 2018, U.S. Pat. Pub. No. 2019/0206004 entitled "Interactive Surgical Systems With Condition Handling Of Devices And Data Capabilities" filed Mar. 29, 2018, U.S. Pat. Pub. No. 2019/0206555 entitled "Cloud-based Medical Analytics For Customization And Recommendations To A User" filed Mar. 29, 2018, and U.S. Pat. Pub. No. 2019/0207857 entitled "Surgical Network Determination Of Prioritization Of Communication, Interaction, Or Processing Based On System Or Device Needs" filed Nov. 6, 2018, which are hereby incorporated by reference in their entireties.

Figure 18:
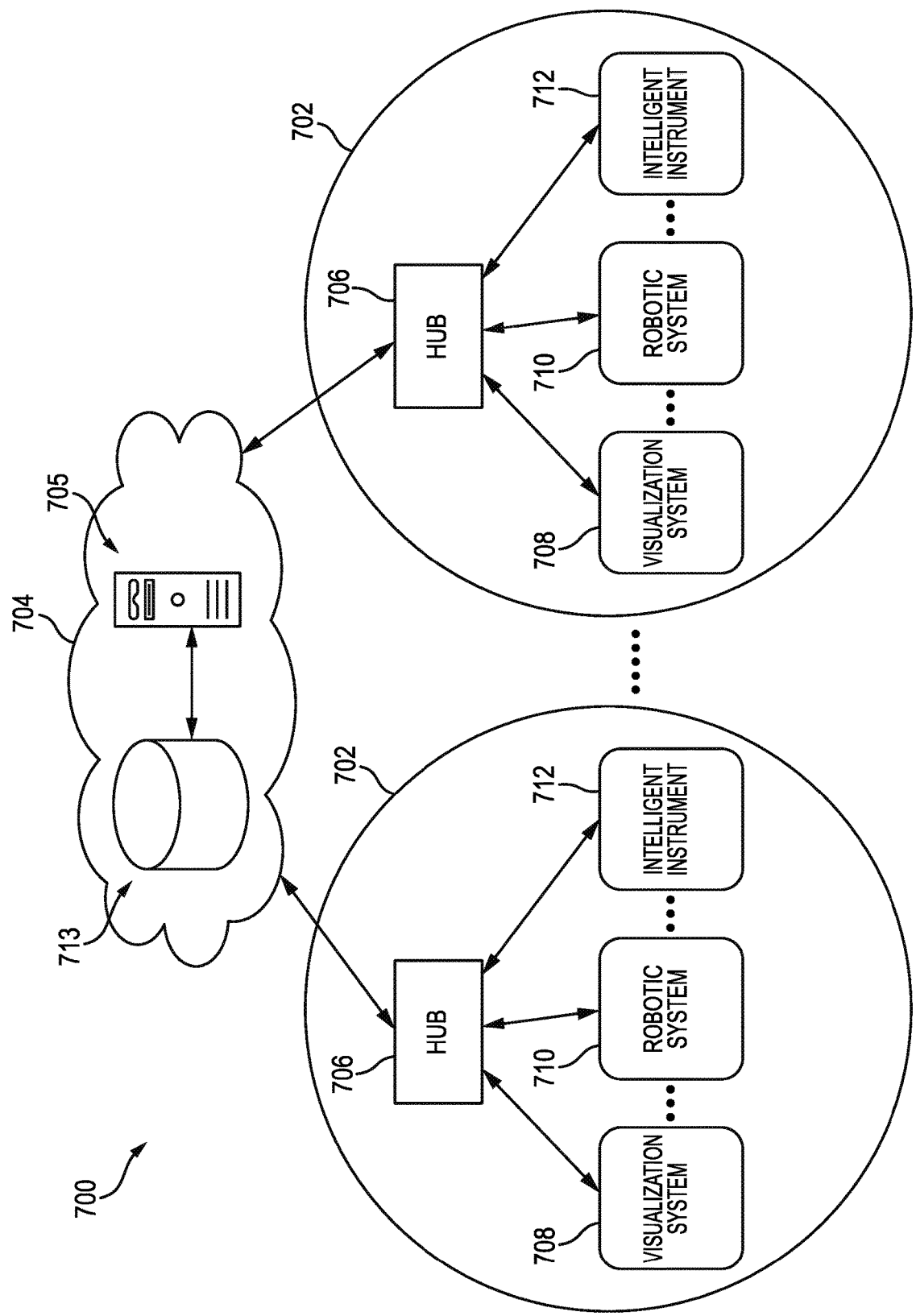
FIG. 18 is a schematic view of one embodiment of a computer-implemented interactive surgical system.

FIG. 18 illustrates one embodiment of a computer-implemented interactive surgical system 700 that includes one or more surgical systems 702 and a cloud-based system (e.g., a cloud 704 that can include a remote server 713 coupled to a storage device 705). Each surgical system 702 includes at least one surgical hub 706 in communication with the cloud 704. In one example, as illustrated in FIG. 18, the surgical system 702 includes a visualization system 708, a robotic system 710, and an intelligent (or "smart") surgical instrument 712, which are configured to communicate with one another and/or the hub 706. The intelligent surgical instrument 712 can include imaging device(s). The surgical system 702 can include an M number of hubs 706, an N number of visualization systems 708, an O number of robotic systems 710, and a P number of intelligent surgical instruments 712, where M, N, O, and P are integers greater than or equal to one that may or may not be equal to any one or more of each other. Various exemplary intelligent surgical instruments and robotic systems are described herein.

Data received by a surgical hub from a surgical visualization system can be used in any of a variety of ways. In an exemplary embodiment, the surgical hub can receive data from a surgical visualization system in use with a patient in a surgical setting, e.g., in use in an operating room during performance of a surgical procedure. The surgical hub can use the received data in any of one or more ways, as discussed herein.

The surgical hub can be configured to analyze received data in real time with use of the surgical visualization system and adjust control one or more of the surgical visualization system and/or one or more intelligent surgical instruments in use with the patient based on the analysis of the received data. Such adjustment can include, for example, adjusting one or operational control parameters of intelligent surgical instrument(s), causing one or more sensors of one or more intelligent surgical instruments to take a measurement to help gain an understanding of the patient's current physiological condition, and/or current operational status of an intelligent surgical instrument, and other adjustments. Controlling and adjusting operation of intelligent surgical instruments is discussed further below. Examples of operational control parameters of an intelligent surgical instrument include motor speed, cutting element speed, time, duration, level of energy application, and light emission. Examples of surgical hubs and of controlling and adjusting intelligent surgical instrument operation are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec. 30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019, and in U.S. patent application Ser. No. 17/068,857 entitled "Adaptive Responses From Smart Packaging Of Drug Delivery Absorbable Adjuncts" filed Oct. 13, 2020, U.S. patent application Ser. No. 17/068,858 entitled "Drug Administration Devices That Communicate With Surgical Hubs" filed Oct. 13, 2020, U.S. patent application Ser. No. 17/068,859 entitled "Controlling Operation Of Drug Administration Devices Using Surgical Hubs" filed Oct. 13, 2020, U.S. patent application Ser. No. 17/068,863 entitled "Patient Monitoring Using Drug Administration Devices" filed Oct. 13, 2020, U.S. patent application Ser. No. 17/068,865 entitled "Monitoring And Communicating Information Using Drug Administration Devices" filed Oct. 13, 2020, and U.S. patent application Ser. No. 17/068,867 entitled "Aggregating And Analyzing Drug Administration Data" filed Oct. 13, 2020, which are hereby incorporated by reference in their entireties.

The surgical hub can be configured to cause visualization of the received data to be provided in the surgical setting on a display so that a medical practitioner in the surgical setting can view the data and thereby receive an understanding of the operation of the imaging device(s) in use in the surgical setting. Such information provided via visualization can include text and/or images.

Figure 19:
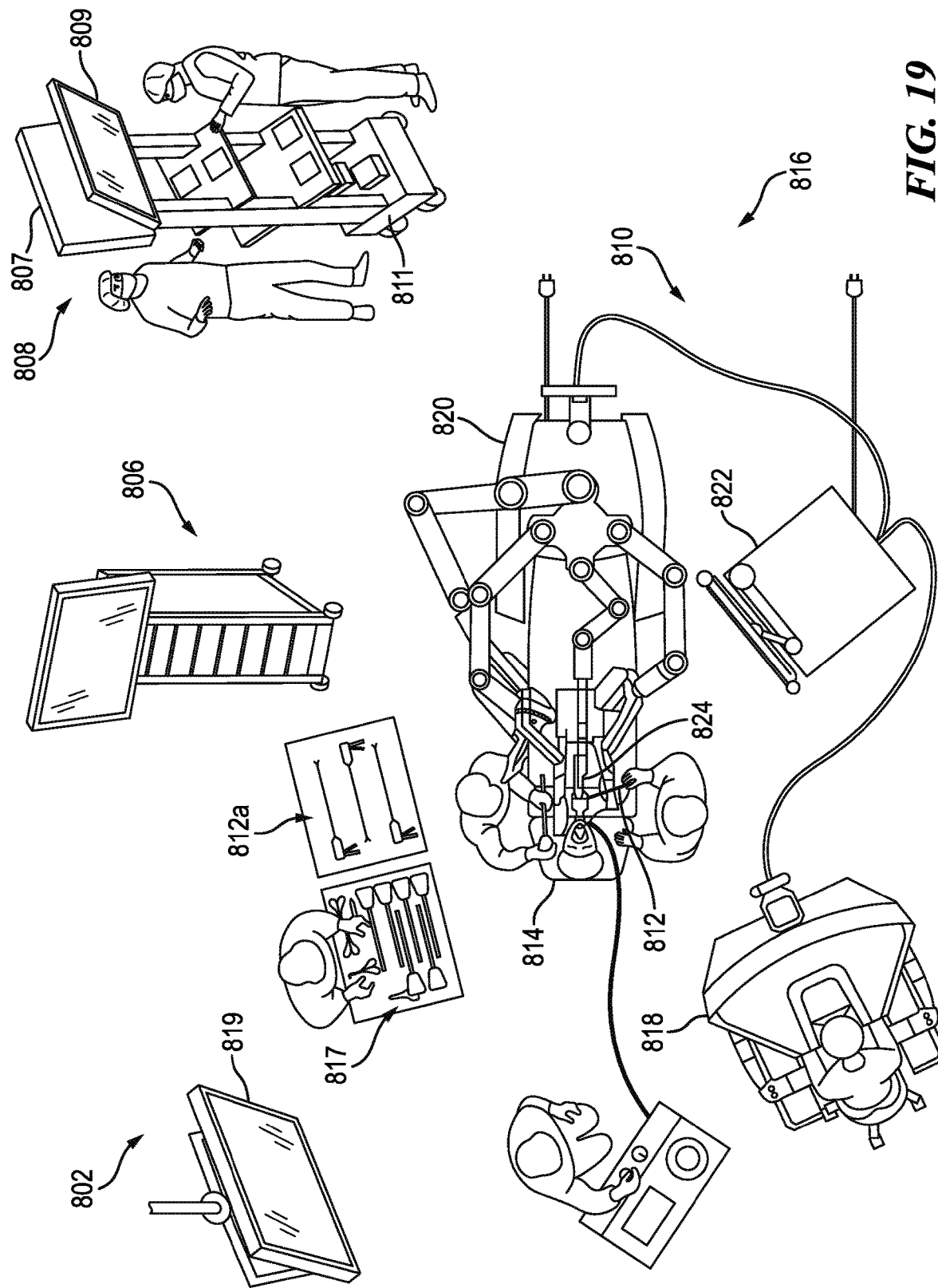
FIG. 19 is a schematic view of one embodiment a surgical system being used to perform a surgical procedure in an operating room.

FIG. 19 illustrates one embodiment of a surgical system 802 including a surgical hub 806 (e.g., the surgical hub 706 of FIG. 18 or other surgical hub described herein), a robotic surgical system 810 (e.g., the robotic surgical system 110 of FIG. 1 or other robotic surgical system herein), and a visualization system 808 (e.g., the visualization system 100 of FIG. 1 or other visualization system described herein). The surgical hub 806 can be in communication with a cloud, as discussed herein. FIG. 19 shows the surgical system 802 being used to perform a surgical procedure on a patient who is lying down on an operating table 814 in a surgical operating room 816. The robotic system 810 includes a surgeon's console 818, a patient side cart 820 (surgical robot), and a robotic system surgical hub 822. The robotic system surgical hub 822 is generally configured similar to the surgical hub 822 and can be in communication with a cloud. In some embodiments, the robotic system surgical hub 822 and the surgical hub 806 can be combined. The patient side cart 820 can manipulate an intelligent surgical tool 812 through a minimally invasive incision in the body of the patient while a medical practitioner, e.g., a surgeon, nurse, and/or other medical practitioner, views the surgical site through the surgeon's console 818. An image of the surgical site can be obtained by an imaging device 824 (e.g., the imaging device 120 of FIG. 1 or other imaging device described herein), which can be manipulated by the patient side cart 820 to orient the imaging device 824. The robotic system surgical hub 822 can be used to process the images of the surgical site for subsequent display to the surgeon through the surgeon's console 818.

A primary display 819 is positioned in the sterile field of the operating room 816 and is configured to be visible to an operator at the operating table 814. In addition, as in this illustrated embodiment, a visualization tower 818 can positioned outside the sterile field. The visualization tower 818 includes a first non-sterile display 807 and a second non-sterile display 809, which face away from each other. The visualization system 808, guided by the surgical hub 806, is configured to utilize the displays 807, 809, 819 to coordinate information flow to medical practitioners inside and outside the sterile field. For example, the surgical hub 806 can cause the visualization system 808 to display a snapshot and/or a video of a surgical site, as obtained by the imaging device 824, on one or both of the non-sterile displays 807, 809, while maintaining a live feed of the surgical site on the primary display 819. The snapshot and/or video on the non-sterile display 807 and/or 809 can permit a non-sterile medical practitioner to perform a diagnostic step relevant to the surgical procedure, for example.

The surgical hub 806 is configured to route a diagnostic input or feedback entered by a non-sterile medical practitioner at the visualization tower 818 to the primary display 819 within the sterile field, where it can be viewed by a sterile medical practitioner at the operating table 814. For example, the input can be in the form of a modification to the snapshot and/or video displayed on the non-sterile display 807 and/or 809, which can be routed to the primary display 819 by the surgical hub 806.

The surgical hub 806 is configured to coordinate information flow to a display of the intelligent surgical instrument 812, as is described in various U.S. Patent Applications that are incorporated by reference herein in the present disclosure. A diagnostic input or feedback entered by a non-sterile operator at the visualization tower 818 can be routed by the surgical hub 806 to the display 819 within the sterile field, where it can be viewed by the operator of the surgical instrument 812 and/or by other medical practitioner(s) in the sterile field.

The intelligent surgical instrument 812 and the imaging device 824, which is also an intelligent surgical tool, is being used with the patient in the surgical procedure as part of the surgical system 802. Other intelligent surgical instruments 812a that can be used in the surgical procedure, e.g., that can be removably coupled to the patient side cart 820 and be in communication with the robotic surgical system 810 and the surgical hub 806, are also shown in FIG. 19 as being available. Non-intelligent (or "dumb") surgical instruments 817, e.g., scissors, trocars, cannulas, scalpels, etc., that cannot be in communication with the robotic surgical system 810 and the surgical hub 806 are also shown in FIG. 19 as being available for use.

Operating Intelligent Surgical Instruments

An intelligent surgical device can have an algorithm stored thereon, e.g., in a memory thereof, configured to be executable on board the intelligent surgical device, e.g., by a processor thereof, to control operation of the intelligent surgical device. In some embodiments, instead of or in addition to being stored on the intelligent surgical device, the algorithm can be stored on a surgical hub, e.g., in a memory thereof, that is configured to communicate with the intelligent surgical device.

The algorithm is stored in the form of one or more sets of pluralities of data points defining and/or representing instructions, notifications, signals, etc. to control functions of the intelligent surgical device. In some embodiments, data gathered by the intelligent surgical device can be used by the intelligent surgical device, e.g., by a processor of the intelligent surgical device, to change at least one variable parameter of the algorithm. As discussed above, a surgical hub can be in communication with an intelligent surgical device, so data gathered by the intelligent surgical device can be communicated to the surgical hub and/or data gathered by another device in communication with the surgical hub can be communicated to the surgical hub, and data can be communicated from the surgical hub to the intelligent surgical device. Thus, instead of or in addition to the intelligent surgical device being configured to change a stored variable parameter, the surgical hub can be configured to communicate the changed at least one variable, alone or as part of the algorithm, to the intelligent surgical device and/or the surgical hub can communicate an instruction to the intelligent surgical device to change the at least one variable as determined by the surgical hub.

The at least one variable parameter is among the algorithm's data points, e.g., are included in instructions for operating the intelligent surgical device, and are thus each able to be changed by changing one or more of the stored pluralities of data points of the algorithm. After the at least one variable parameter has been changed, subsequent execution of the algorithm is according to the changed algorithm. As such, operation of the intelligent surgical device over time can be managed for a patient to increase the beneficial results use of the intelligent surgical device by taking into consideration actual situations of the patient and actual conditions and/or results of the surgical procedure in which the intelligent surgical device is being used. Changing the at least one variable parameter is automated to improve patient outcomes. Thus, the intelligent surgical device can be configured to provide personalized medicine based on the patient and the patient's surrounding conditions to provide a smart system. In a surgical setting in which the intelligent surgical device is being used during performance of a surgical procedure, automated changing of the at least one variable parameter may allow for the intelligent surgical device to be controlled based on data gathered during the performance of the surgical procedure, which may help ensure that the intelligent surgical device is used efficiently and correctly and/or may help reduce chances of patient harm by harming a critical anatomical structure.

The at least one variable parameter can be any of a variety of different operational parameters. Examples of variable parameters include motor speed, motor torque, energy level, energy application duration, tissue compression rate, jaw closure rate, cutting element speed, load threshold, etc.

Figure 20:
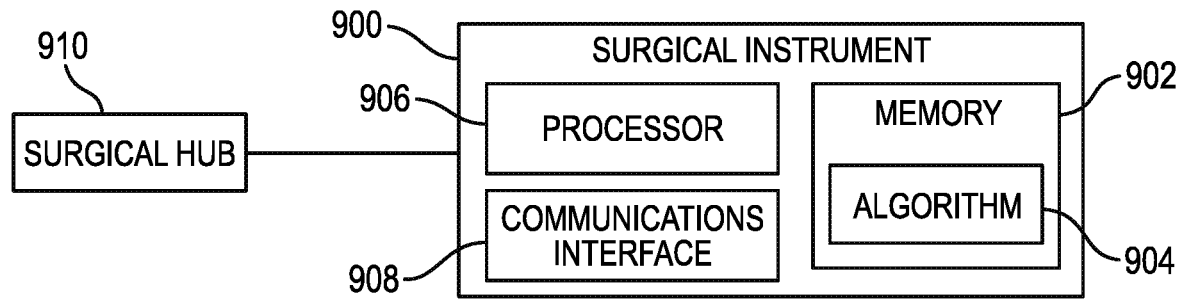
FIG. 20 is a schematic view of one embodiment of a surgical system including a smart surgical instrument and a surgical hub.

FIG. 20 illustrates one embodiment of an intelligent surgical instrument 900 including a memory 902 having an algorithm 904 stored therein that includes at least one variable parameter. The algorithm 904 can be a single algorithm or can include a plurality of algorithms, e.g., separate algorithms for different aspects of the surgical instrument's operation, where each algorithm includes at least one variable parameter. The intelligent surgical instrument 900 can be the surgical device 102 of FIG. 1, the imaging device 120 of FIG. 1, the surgical device 202 of FIG. 8, the imaging device 220 of FIG. 8, the surgical device 402 of FIG. 15, the surgical device 502a of FIG. 17, the surgical device 502b of FIG. 17, the surgical device 712 of FIG. 18, the surgical device 812 of FIG. 19, the imaging device 824 of FIG. 19, or other intelligent surgical instrument. The surgical instrument 900 also includes a processor 906 configured to execute the algorithm 904 to control operation of at least one aspect of the surgical instrument 900. To execute the algorithm 904, the processor 906 is configured to run a program stored in the memory 902 to access a plurality of data points of the algorithm 904 in the memory 902.

The surgical instrument 900 also includes a communications interface 908, e.g., a wireless transceiver or other wired or wireless communications interface, configured to communicate with another device, such as a surgical hub 910. The communications interface 908 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the surgical instrument 900 and/or data stored thereon and receiving instructions, such as from a doctor; a remote server regarding updates to software; a local, surgical hub server regarding updates to software; etc.

The surgical instrument 900 is simplified in FIG. 20 and can include additional components, e.g., a bus system, a handle, a elongate shaft having an end effector at a distal end thereof, a power source, etc. The processor 906 can also be configured to execute instructions stored in the memory 902 to control the device 900 generally, including other electrical components thereof such as the communications interface 908, an audio speaker, a user interface, etc.

The processor 906 is configured to change at least one variable parameter of the algorithm 904 such that a subsequent execution of the algorithm 904 will be in accordance with the changed at least one variable parameter. To change the at least one variable parameter of the algorithm 904, the processor 906 is configured to modify or update the data point(s) of the at least one variable parameter in the memory 902. The processor 906 can be configured to change the at least one variable parameter of the algorithm 904 in real time with use of the surgical device 900 during performance of a surgical procedure, which may accommodate real time conditions.

Additionally or alternatively to the processor 906 changing the at least one variable parameter, the processor 906 can be configured to change the algorithm 904 and/or at least one variable parameter of the algorithm 904 in response to an instruction received from the surgical hub 910. In some embodiments, the processor 906 is configured to change the at least one variable parameter only after communicating with the surgical hub 910 and receiving an instruction therefrom, which may help ensure coordinated action of the surgical instrument 900 with other aspects of the surgical procedure in which the surgical instrument 900 is being used.

In an exemplary embodiment, the processor 906 executes the algorithm 904 to control operation of the surgical instrument 900, changes the at least one variable parameter of the algorithm 904 based on real time data, and executes the algorithm 904 after changing the at least one variable parameter to control operation of the surgical instrument 900.

Figure 21:
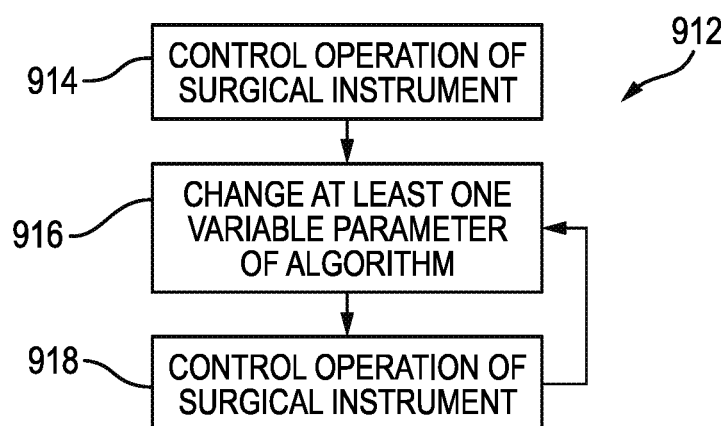
FIG. 21 is a flowchart showing a method of controlling the smart surgical instrument of FIG. 20.

FIG. 21 illustrates one embodiment of a method 912 of using of the surgical instrument 900 including a change of at least one variable parameter of the algorithm 904. The processor 906 controls 914 operation of the surgical instrument 900 by executing the algorithm 904 stored in the memory 902. Based on any of this subsequently known data and/or subsequently gathered data, the processor 904 changes 916 the at least one variable parameter of the algorithm 904 as discussed above. After changing the at least one variable parameter, the processor 906 controls 918 operation of the surgical instrument 900 by executing the algorithm 904, now with the changed at least one variable parameter. The processor 904 can change 916 the at least one variable parameter any number of times during performance of a surgical procedure, e.g., zero, one, two, three, etc. During any part of the method 912, the surgical instrument 900 can communicate with one or more computer systems, e.g., the surgical hub 910, a remote server such as a cloud server, etc., using the communications interface 908 to provide data thereto and/or receive instructions therefrom.

Situational Awareness

Operation of an intelligent surgical instrument can be altered based on situational awareness of the patient. The operation of the intelligent surgical instrument can be altered manually, such as by a user of the intelligent surgical instrument handling the instrument differently, providing a different input to the instrument, ceasing use of the instrument, etc. Additionally or alternatively, the operation of an intelligent surgical instrument can be changed automatically by an algorithm of the instrument being changed, e.g., by changing at least one variable parameter of the algorithm. As mentioned above, the algorithm can be adjusted automatically without user input requesting the change. Automating the adjustment during performance of a surgical procedure may help save time, may allow medical practitioners to focus on other aspects of the surgical procedure, and/or may ease the process of using the surgical instrument for a medical practitioner, which each may improve patient outcomes, such as by avoiding a critical structure, controlling the surgical instrument with consideration of a tissue type the instrument is being used on and/or near, etc.

The visualization systems described herein can be utilized as part of a situational awareness system that can be embodied or executed by a surgical hub, e.g., the surgical hub 706, the surgical hub 806, or other surgical hub described herein. In particular, characterizing, identifying, and/or visualizing surgical instruments (including their positions, orientations, and actions), tissues, structures, users, and/or other things located within the surgical field or the operating theater can provide contextual data that can be utilized by a situational awareness system to infer various information, such as a type of surgical procedure or a step thereof being performed, a type of tissue(s) and/or structure(s) being manipulated by a surgeon or other medical practitioner, and other information. The contextual data can then be utilized by the situational awareness system to provide alerts to a user, suggest subsequent steps or actions for the user to undertake, prepare surgical devices in anticipation for their use (e.g., activate an electrosurgical generator in anticipation of an electrosurgical instrument being utilized in a subsequent step of the surgical procedure, etc.), control operation of intelligent surgical instruments (e.g., customize surgical instrument operational parameters of an algorithm as discussed further below), and so on.

Although an intelligent surgical device including an algorithm that responds to sensed data, e.g., by having at least one variable parameter of the algorithm changed, can be an improvement over a "dumb" device that operates without accounting for sensed data, some sensed data can be incomplete or inconclusive when considered in isolation, e.g., without the context of the type of surgical procedure being performed or the type of tissue that is being operated on. Without knowing the procedural context (e.g., knowing the type of tissue being operated on or the type of procedure being performed), the algorithm may control the surgical device incorrectly or sub-optimally given the particular context-free sensed data. For example, the optimal manner for an algorithm to control a surgical instrument in response to a particular sensed parameter can vary according to the particular tissue type being operated on. This is due to the fact that different tissue types have different properties (e.g., resistance to tearing, ease of being cut, etc.) and thus respond differently to actions taken by surgical instruments. Therefore, it may be desirable for a surgical instrument to take different actions even when the same measurement for a particular parameter is sensed. As one example, the optimal manner in which to control a surgical stapler in response to the surgical stapler sensing an unexpectedly high force to close its end effector will vary depending upon whether the tissue type is susceptible or resistant to tearing. For tissues that are susceptible to tearing, such as lung tissue, the surgical instrument's control algorithm would optimally ramp down the motor in response to an unexpectedly high force to close to avoid tearing the tissue, e.g., change a variable parameter controlling motor speed or torque so the motor is slower. For tissues that are resistant to tearing, such as stomach tissue, the instrument's algorithm would optimally ramp up the motor in response to an unexpectedly high force to close to ensure that the end effector is clamped properly on the tissue, e.g., change a variable parameter controlling motor speed or torque so the motor is faster. Without knowing whether lung or stomach tissue has been clamped, the algorithm may be sub-optimally changed or not changed at all.

A surgical hub can be configured to derive information about a surgical procedure being performed based on data received from various data sources and then control modular devices accordingly. In other words, the surgical hub can be configured to infer information about the surgical procedure from received data and then control the modular devices operably coupled to the surgical hub based upon the inferred context of the surgical procedure. Modular devices can include any surgical device that is controllable by a situational awareness system, such as visualization system devices (e.g., a camera, a display screen, etc.), smart surgical instruments (e.g., an ultrasonic surgical instrument, an electrosurgical instrument, a surgical stapler, smoke evacuators, scopes, etc.). A modular device can include sensor(s)s configured to detect parameters associated with a patient with which the device is being used and/or associated with the modular device itself.

The contextual information derived or inferred from the received data can include, for example, a type of surgical procedure being performed, a particular step of the surgical procedure that the surgeon (or other medical practitioner) is performing, a type of tissue being operated on, or a body cavity that is the subject of the surgical procedure. The situational awareness system of the surgical hub can be configured to derive the contextual information from the data received from the data sources in a variety of different ways. In an exemplary embodiment, the contextual information received by the situational awareness system of the surgical hub is associated with a particular control adjustment or set of control adjustments for one or more modular devices. The control adjustments each correspond to a variable parameter. In one example, the situational awareness system includes a pattern recognition system, or machine learning system (e.g., an artificial neural network), that has been trained on training data to correlate various inputs (e.g., data from databases, patient monitoring devices, and/or modular devices) to corresponding contextual information regarding a surgical procedure. In other words, a machine learning system can be trained to accurately derive contextual information regarding a surgical procedure from the provided inputs. In another example, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling at least one modular device. In another example, the situational awareness system includes a further machine learning system, lookup table, or other such system, which generates or retrieves one or more control adjustments for one or more modular devices when provided the contextual information as input.

A surgical hub including a situational awareness system may provide any number of benefits for a surgical system. One benefit includes improving the interpretation of sensed and collected data, which would in turn improve the processing accuracy and/or the usage of the data during the course of a surgical procedure. Another benefit is that the situational awareness system for the surgical hub may improve surgical procedure outcomes by allowing for adjustment of surgical instruments (and other modular devices) for the particular context of each surgical procedure (such as adjusting to different tissue types) and validating actions during a surgical procedure. Yet another benefit is that the situational awareness system may improve surgeon's and/or other medical practitioners' efficiency in performing surgical procedures by automatically suggesting next steps, providing data, and adjusting displays and other modular devices in the surgical theater according to the specific context of the procedure. Another benefit includes proactively and automatically controlling modular devices according to the particular step of the surgical procedure that is being performed to reduce the number of times that medical practitioners are required to interact with or control the surgical system during the course of a surgical procedure, such as by a situationally aware surgical hub proactively activating a generator to which an RF electrosurgical instrument is connected if it determines that a subsequent step of the procedure requires the use of the instrument. Proactively activating the energy source allows the instrument to be ready for use a soon as the preceding step of the procedure is completed.

For example, a situationally aware surgical hub can be configured to determine what type of tissue is being operated on. Therefore, when an unexpectedly high force to close a surgical instrument's end effector is detected, the situationally aware surgical hub can be configured to correctly ramp up or ramp down a motor of the surgical instrument for the type of tissue, e.g., by changing or causing change of at least one variable parameter of an algorithm for the surgical instrument regarding motor speed or torque.

For another example, a type of tissue being operated can affect adjustments that are made to compression rate and load thresholds of a surgical stapler for a particular tissue gap measurement. A situationally aware surgical hub can be configured to infer whether a surgical procedure being performed is a thoracic or an abdominal procedure, allowing the surgical hub to determine whether the tissue clamped by an end effector of the surgical stapler is lung tissue (for a thoracic procedure) or stomach tissue (for an abdominal procedure). The surgical hub can then be configured to cause adjustment of the compression rate and load thresholds of the surgical stapler appropriately for the type of tissue, e.g., by changing or causing change of at least one variable parameter of an algorithm for the surgical stapler regarding compression rate and load threshold.

As yet another example, a type of body cavity being operated in during an insufflation procedure can affect the function of a smoke evacuator. A situationally aware surgical hub can be configured to determine whether the surgical site is under pressure (by determining that the surgical procedure is utilizing insufflation) and determine the procedure type. As a procedure type is generally performed in a specific body cavity, the surgical hub can be configured to control a motor rate of the smoke evacuator appropriately for the body cavity being operated in, e.g., by changing or causing change of at least one variable parameter of an algorithm for the smoke evacuator regarding motor rate. Thus, a situationally aware surgical hub may provide a consistent amount of smoke evacuation for both thoracic and abdominal procedures.

As yet another example, a type of procedure being performed can affect the optimal energy level for an ultrasonic surgical instrument or radio frequency (RF) electrosurgical instrument to operate at. Arthroscopic procedures, for example, require higher energy levels because an end effector of the ultrasonic surgical instrument or RF electrosurgical instrument is immersed in fluid. A situationally aware surgical hub can be configured to determine whether the surgical procedure is an arthroscopic procedure. The surgical hub can be configured to adjust an RF power level or an ultrasonic amplitude of the generator (e.g., adjust energy level) to compensate for the fluid filled environment, e.g., by changing or causing change of at least one variable parameter of an algorithm for the instrument and/or a generator regarding energy level. Relatedly, a type of tissue being operated on can affect the optimal energy level for an ultrasonic surgical instrument or RF electrosurgical instrument to operate at. A situationally aware surgical hub can be configured to determine what type of surgical procedure is being performed and then customize the energy level for the ultrasonic surgical instrument or RF electrosurgical instrument, respectively, according to the expected tissue profile for the surgical procedure, e.g., by changing or causing change of at least one variable parameter of an algorithm for the instrument and/or a generator regarding energy level. Furthermore, a situationally aware surgical hub can be configured to adjust the energy level for the ultrasonic surgical instrument or RF electrosurgical instrument throughout the course of a surgical procedure, rather than just on a procedure-by-procedure basis. A situationally aware surgical hub can be configured to determine what step of the surgical procedure is being performed or will subsequently be performed and then update the control algorithm(s) for the generator and/or ultrasonic surgical instrument or RF electrosurgical instrument to set the energy level at a value appropriate for the expected tissue type according to the surgical procedure step.

As another example, a situationally aware surgical hub can be configured to determine whether the current or subsequent step of a surgical procedure requires a different view or degree of magnification on a display according to feature(s) at the surgical site that the surgeon and/or other medical practitioner is expected to need to view. The surgical hub can be configured to proactively change the displayed view (supplied by, e.g., an imaging device for a visualization system) accordingly so that the display automatically adjusts throughout the surgical procedure.

As yet another example, a situationally aware surgical hub can be configured to determine which step of a surgical procedure is being performed or will subsequently be performed and whether particular data or comparisons between data will be required for that step of the surgical procedure. The surgical hub can be configured to automatically call up data screens based upon the step of the surgical procedure being performed, without waiting for the surgeon or other medical practitioner to ask for the particular information.

As another example, a situationally aware surgical hub can be configured to determine whether a surgeon and/or other medical practitioner is making an error or otherwise deviating from an expected course of action during the course of a surgical procedure, e.g., as provided in a preoperative surgical plan. For example, the surgical hub can be configured to determine a type of surgical procedure being performed, retrieve a corresponding list of steps or order of equipment usage (e.g., from a memory), and then compare the steps being performed or the equipment being used during the course of the surgical procedure to the expected steps or equipment for the type of surgical procedure that the surgical hub determined is being performed. The surgical hub can be configured to provide an alert (visual, audible, and/or tactile) indicating that an unexpected action is being performed or an unexpected device is being utilized at the particular step in the surgical procedure.

In certain instances, operation of a robotic surgical system, such as any of the various robotic surgical systems described herein, can be controlled by the surgical hub based on its situational awareness and/or feedback from the components thereof and/or based on information from a cloud (e.g., the cloud 713 of FIG. 18).

Embodiments of situational awareness systems and using situational awareness systems during performance of a surgical procedure are described further in previously mentioned U.S. patent application Ser. No. 16/729,772 entitled "Analyzing Surgical Trends By A Surgical System" filed Dec. 30, 2019, U.S. patent application Ser. No. 16/729,747 entitled "Dynamic Surgical Visualization Systems" filed Dec. 30, 2019, U.S. patent application Ser. No. 16/729,744 entitled "Visualization Systems Using Structured Light" filed Dec. 30, 2019, U.S. patent application Ser. No. 16/729,778 entitled "System And Method For Determining, Adjusting, And Managing Resection Margin About A Subject Tissue" filed Dec. 30, 2019, U.S. patent application Ser. No. 16/729,729 entitled "Surgical Systems For Proposing And Corroborating Organ Portion Removals" filed Dec. 30, 2019, U.S. patent application Ser. No. 16/729,778 entitled "Surgical System For Overlaying Surgical Instrument Data Onto A Virtual Three Dimensional Construct Of An Organ" filed Dec. 30, 2019, U.S. patent application Ser. No. 16/729,751 entitled "Surgical Systems For Generating Three Dimensional Constructs Of Anatomical Organs And Coupling Identified Anatomical Structures Thereto" filed Dec.

30, 2019, U.S. patent application Ser. No. 16/729,740 entitled "Surgical Systems Correlating Visualization Data And Powered Surgical Instrument Data" filed Dec. 30, 2019, U.S. patent application Ser. No. 16/729,737 entitled "Adaptive Surgical System Control According To Surgical Smoke Cloud Characteristics" filed Dec. 30, 2019, U.S. patent application Ser. No. 16/729,796 entitled "Adaptive Surgical System Control According To Surgical Smoke Particulate Characteristics" filed Dec. 30, 2019, U.S. patent application Ser. No. 16/729,803 entitled "Adaptive Visualization By A Surgical System" filed Dec. 30, 2019, and U.S. patent application Ser. No. 16/729,807 entitled "Method Of Using Imaging Devices In Surgery" filed Dec. 30, 2019.

Surgical Sealing Devices for a Natural Body Orifice

In certain embodiments, surgical sealing devices are provided that are configured to allow surgical access into a body cavity through a natural body orifice (e.g., a trachea, a rectum, and the like). In general, the present surgical sealing devices include a seal housing that is configured to be at least partially disposed within a natural body orifice and at least one retention element configured to affix the seal housing to the natural body orifice. Unlike conventional surgical sealing devices that are typically inserted into an incision, the present surgical sealing devices are designed to be inserted into a natural body orifice. As a result, the present surgical sealing devices provide a less traumatic and more direct access point to a natural body lumen or organ (e.g., for introduction and extraction of surgical instruments, fluid exchange, breathing apparatuses, smoke evacuation apparatuses, etc.) that would not otherwise be available through the use of conventional surgical sealing devices.

In use, as discussed in more detail below, the surgical sealing devices disclosed herein can be used to provide access to a natural body lumen, such as a colon, through a natural body orifice associated therewith. That is, the seal housing can be at least partially positioned within a natural body orifice. Given the contractive nature of a natural body orifice, however, it can be difficult maintain the seal housing within the natural body office. As a result, the surgical sealing devices include at least one retention element (e.g., arranged on an exterior surface of the seal housing) that enables and maintains fixation of the seal housing to the natural body orifice during device use. The at least one retention element can be configured to be deployed inside or outside of the patient's body.

The seal housing can be positioned and affixed to the natural body orifice in such a way in which a distal portion of the seal housing extends into the natural body orifice, and a proximal portion extends out of the natural body orifice and into the ambient environment (e.g., positioned adjacent to and in contact with an exterior surface of the patient's body, such as the patient's skin. Alternatively, the seal housing can be designed to be entirely positioned within the natural body orifice.

Further, the seal housing generally includes one or more ports arranged within the seal housing to allow instruments to pass into the natural body lumen from the ambient environment through the natural body orifice. The one or more ports arranged through the seal housing can form pathway(s) into and through the natural body orifice. This can enable controlled fluid exchange through the natural body orifice, and consequently, into and/or out of the natural body lumen associated therewith, introduction and extraction of surgical instruments through the natural body orifice, and the like. As a result, the natural body lumen can be accessed without the need for an incision through the patient's skin.

Figure 22:
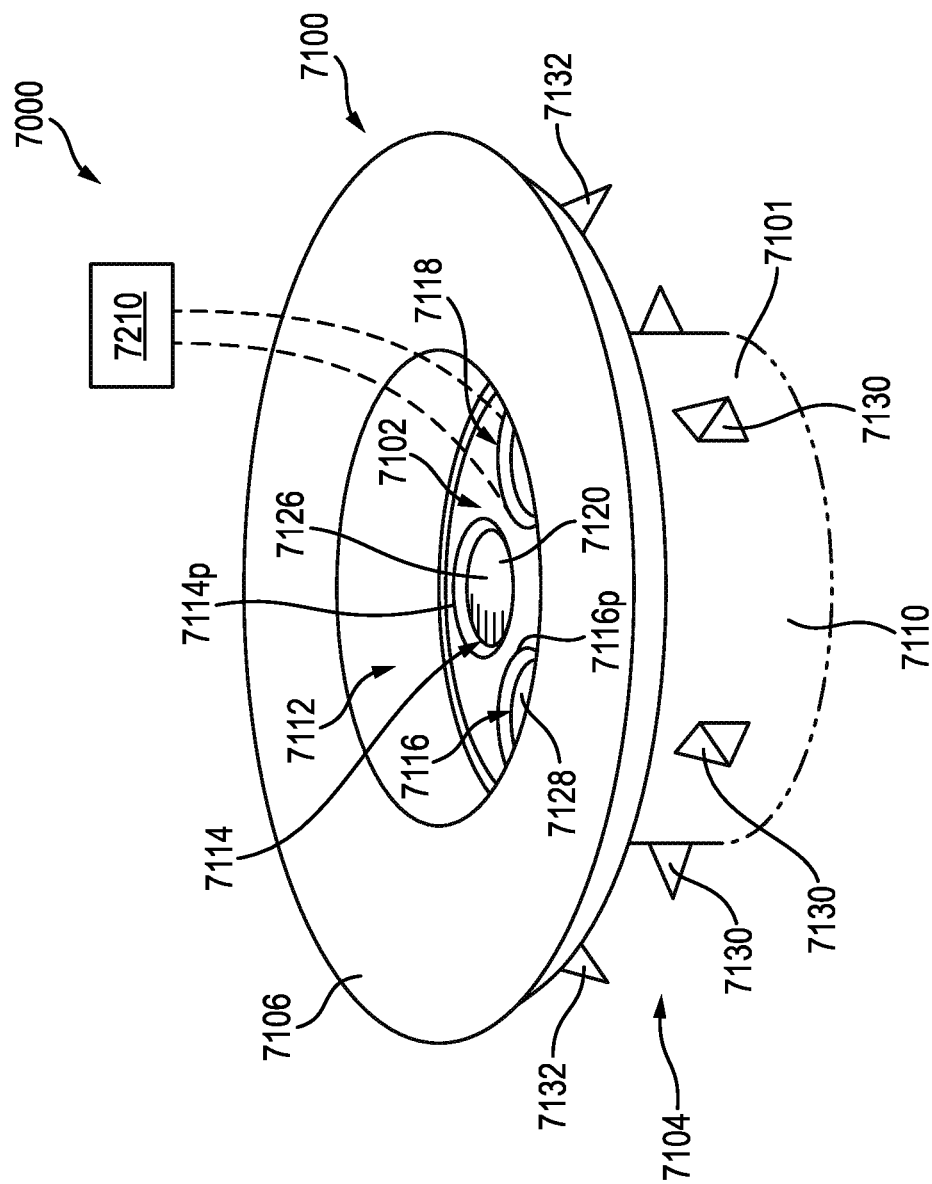
FIG. 22 is a schematic view of an exemplary embodiment of a surgical sealing device.
Figure 23:
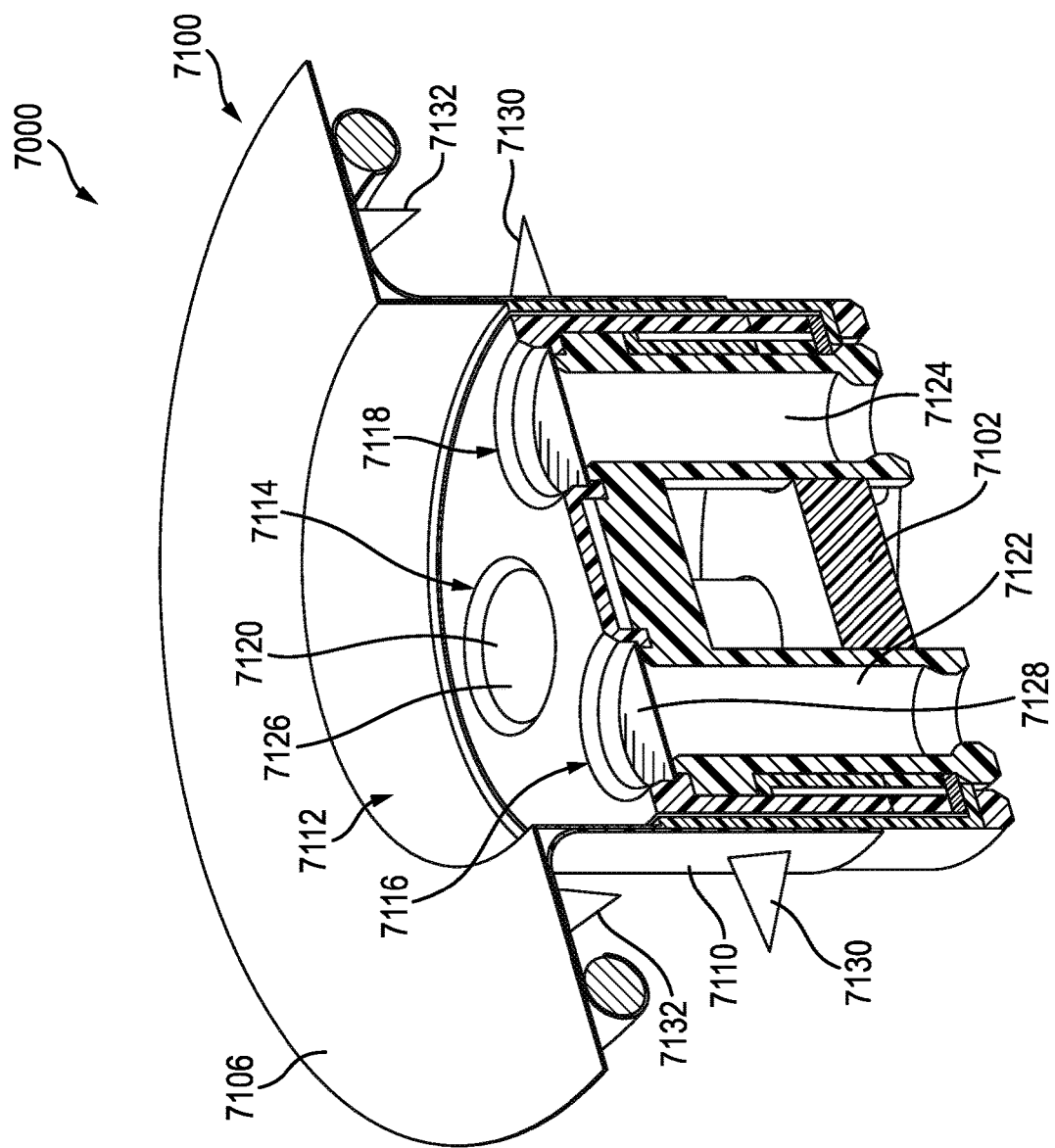
FIG. 23 is a cross-sectional view of the surgical sealing device of FIG. 22.

FIG. 22 and FIG. 23 illustrate one embodiment of a surgical sealing device 7000 that is configured to provide access into a natural body lumen or organ (e.g., a lung, a stomach, a colon, or small intestines) through a natural body orifice (e.g., esophagus, rectum, and the like). Therefore, at least a portion of the surgical sealing device 7000 is configured to be inserted into and stabilized within a natural body orifice.

The sealing device 7000 includes a seal housing 7100 with ports extending therethrough and at least one retention element on the exterior surface 7101 of the seal housing 7100. While the at least one retention element can have a variety of configurations, in this illustrated embodiment, the at least one retention element includes first retention elements 7130 and second retention elements 7132. The first and second retention elements 7130, 7132 are configured to secure the seal housing 7100 within a natural body orifice.

In use, the surgical sealing device 7000 can be positioned within a natural body orifice, such as by deforming the seal housing 7100, or a portion thereof (e.g., the outer body member 7104) and inserting the seal housing 7100 in the natural body orifice. The insertion of the seal housing can be performed by hand or by using an insertion tool. The at least one retention element is releasably positioned to thereby affix the seal housing to the natural body orifice. In some embodiments, the at least one retention element can be deployed inside the natural body lumen, whereas in other embodiments, the at least one retention element can be deployed outside of the natural body lumen. The at least one retention member can be releasably positioned concurrently with or subsequently after the sealing housing is positioned at least partially within the natural body lumen. To withdraw the surgical sealing device 7000 from the natural body orifice, a portion of the seal housing 7100 (e.g., the outer body member 7104) can be gripped with one or both hands (such as at opposite sides of the outer body member 7104) or by a removal instrument, or both, and the seal housing 7100 may be pulled proximally to withdraw the seal housing 7100 from natural body orifice. Prior to gripping the seal housing, the at least one retention element can be moved or otherwise disengaged from tissue defining the natural body orifice or tissue positioned proximate to the natural body orifice.

As shown in FIG. 22 and FIG. 23, the first and second retention elements 7130, 7132 are arranged on and extend from the exterior surface 7101 of the seal housing 7100. The first and second retention elements 7130, 7132 can have a variety of configurations. In some embodiments, the first and second retention elements can have the same or similar configurations. In other embodiments, the first and second retention elements can have different structural configurations relative to each other. It is also contemplated herein that in certain embodiments, the first retention elements or the second retention elements can be omitted.

In this illustrated embodiment, the first and second retention elements 7130, 7132 are each in the form of barbs that are configured to penetrate into the tissue to affix the seal housing 7100 to the natural body orifice. Further, the retention elements 7130, 7132 can allow for twisting and deformation of the natural body orifice, which can occur naturally, while also keeping the seal housing 7100 securely lodged within the natural body orifice.

In other embodiments, the at least one retention element can have a structural configuration that is configured to contact and engage the tissue surrounding or adjacent to the natural body orifice without penetration. That is, the at least one retention element can have a structural configuration that is configured to frictionally engage with the tissue so to prevent the seal housing from further movement within the natural body orifice during use. By way of example, in some embodiments, the at least one retention element can be in the form of an expandable element (e.g., inflatable balloons), as illustrated in Figure X. In use, once the seal housing is inserted (e.g., partially or fully) within the natural body orifice, the expandable element(s) can be inflated, and when the seal housing is to be removed from the natural body orifice, the expandable element(s) can be deflated.

In some embodiments, when one or more retention elements are expandable elements, these retention elements can configured to be expanded within the natural body orifice (e.g., after at least a portion of the seal housing is inserted into the natural body orifice). In other embodiments one or more retention elements can be configured to be deployed outside of the natural body lumen (e.g., after at least a portion of the seal housing is inserted into the natural body orifice). Alternatively, in certain embodiments, at least one retention element can be configured to be deployed within the natural body orifice, and at least another one retention element can be configured to be deployed outside the natural body orifice. A person skilled in the art will appreciate that the deployable position of the retention elements depends at least upon the position of the retention elements relative to the seal housing 7100 and the position of the seal housing 7100 relative to the natural body orifice when the seal housing 7100 is inserted therein.

Figure 24:
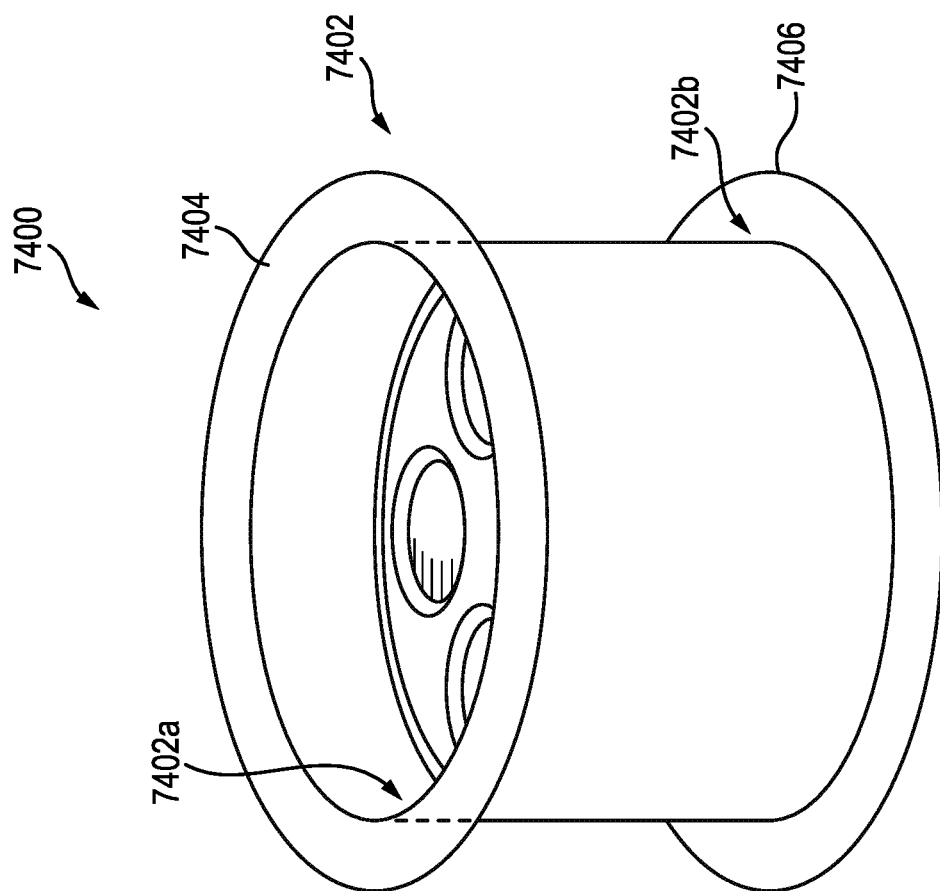
FIG. 24 is a cross-sectional view of another exemplary embodiment of a surgical sealing device.

FIG. 24 illustrates an exemplary embodiment of a surgical sealing device 7400 that includes a sealing housing 7402 and two retention elements 7404, 7406 that are in the form of inflatable balloons. The two retention elements 7404, 7406 are each configured to move from an unexpanded to an expanded state (FIG. 24). Aside from the differences described in detail below, sealing device 7400 can be similar to sealing device 7000 (FIG. 22 and FIG. 23) and therefore common features are not described in detail herein. As shown, the first retention element 7404 is positioned at a first end 7202a of the seal housing 7402 and the second retention element 7406 is positioned at a second end 7202b of the seal housing 7402. Further, when both the first and second retention elements 7404, 7406 are in their expanded state, as illustrated in FIG. 24, they are configured to contact and frictionally engage an internal surface of the natural body orifice. In embodiments where only a portion of the surgical sealing device 7400 is positioned within the natural body orifice, the second end 7402b of the seal housing 7402 can be positioned outside the natural body orifice (e.g., outside of the body of the patient). In such embodiments, the second retention element 7406 can be configured to contact and frictionally engage the outer tissue surface surrounding or adjacent to the natural body orifice (e.g., an external surface of the natural body orifice).

Referring back to FIG. 22 and FIG. 23, the seal housing 7100 of surgical sealing device 7000 can have a variety of configurations. For example, in this illustrated embodiment, the seal housing 7100 has an inner body member 7102 and an outer body member 7104 that is positioned about the inner body member 7102. In other embodiments, the outer body member can designed so as to extend distally from one end of the inner body member. In certain embodiments, the outer body member can be omitted.

The inner body member 7102 and the outer body member 7104 can each have a variety of configurations. In this illustrated embodiment, the inner body member 7102 has a generally cylindrical configuration. The outer body member 7104 includes an annular flange 7106 with an elongated cylindrical base 7110 extending therefrom. Further, the base 7110 defines a lumen 7112 extending therethrough. The lumen 7112, as shown in FIG. 22 and FIG. 23, at least partially houses the inner body member 7102. A person skilled in the art will appreciate that the inner body member and/or the outer body member, and/or portions thereof, can have other suitable shapes and sizes (e.g., oval, elliptical, ovoid, and any combination thereof) and therefore their configurations are not limited to what is shown in the figures.

The inner body member 7102 and the outer body member 7104 can formed as a unitary structure, permanently coupled to each other, or releasably coupled to each other. For example, in some embodiments, the inner body member 7102 can be configured to be inserted into and/or removed from the lumen 7112 (e.g., while the outer body member 7104 is at least partially positioned within a natural body orifice). In certain embodiments, the outer body member 7104 can be configured to provide assistance in preventing the inner body member 7102 from be pushed through the sealing housing 7100 (e.g., and into the body of the patient), and to assist in removing the inner body member 7102 from the seal housing 7100. For example, during surgery, removal of the inner body member 7102 may be needed for removing damaged or diseased tissue through the lumen 7112 of the outer body member 7104. Further, in addition, or alternatively, the outer body member 7104 can be configured to help prevent the inner body member 7102 from being torn or otherwise damaged by surgical instrument(s) that is/are inserted therethrough (e.g., during surgery).

As further shown in FIG. 22 and FIG. 23, the inner body member 7102 includes ports that extend therethrough, and thus, through the seal housing 7100. While the inner body 7102 can include two or more ports, in this illustrated embodiment the inner body member 7102 includes three ports: a first port 7114, a second port 7116, a third port 7118. Each port 7114, 7116, 7118 defines a respective passageway 7120, 7122, 7124 through the seal housing 7100. The ports 7114, 7116, 7118 can be designed as a variety of different ports that serve different functions (e.g., fluid exchange into and/or out of the natural body lumen, sealing instruments inserted therethrough, preventing fluid from escaping out of the natural body orifice and into the ambient environment, and/or the like).

In some embodiments, at least one port can be configured to form a seal (e.g., around an instrument inserted therethrough) and at least another one port can be configured to control the ingress and/or egress of fluid (e.g., liquid, gas, or a combination thereof) between an interior volume of the natural body orifice and an ambient environment. In certain embodiments, at least one port can be configured to seal and control ingress and/or egress of fluid. For purposes of this discussion, the first and second ports 7114, 7116 are each configured to form a respective seal around an instrument inserted therethrough and the third port 7118 is configured to control the fluid ingress and egress. A person skilled in the art that any of these ports can configured to control fluid ingress and/or egress (e.g., air into and/or out of the natural body orifice, e.g., for breathing or insufflation) and/or to form a seal (e.g., around an instrument inserted therethrough and/or when an instrument is absent, for preventing loss of fluid therethrough).

In some embodiments, sealing element(s) can be positioned within the first port and/or second port to form a seal therein. In some embodiments, the sealing element(s) can be in the form of a thin membrane formed of a flexible material which can be punctured or otherwise pierced by a surgical instrument. In addition, or alternatively, zero closure sealing elements such as a duck bill seal or other suitable seals for sealing in the absence of instrument can be used in association with the ports. The sealing elements can be positioned at any suitable location within the port.

As shown in FIG. 22 and FIG. 23, a first sealing element 7126 is positioned within the passageway 7120 of the first port 7114 and a second sealing element 7128 is positioned within the passageway of the second port 7116. In some embodiments, the first and second sealing elements 7126, 7128 can the same, whereas in other embodiments, the first and second sealing elements 7126, 7128 can be different. The first and second sealing elements 7126, 7128 can be positioned in a variety of different locations within the respective passageways. In this illustrated embodiment, the first sealing element 7126 is positioned proximate to the proximal end 7114p (e.g., the end closest to the ambient environment during use) of the first port and the second sealing element 7128 is positioned proximate to the proximal end 7116p (e.g., the end closest to the ambient environment during use) of the second sealing port 7116. In other embodiments, the first sealing element, the second sealing element, or both, can be positioned at a distal end of the second port and the third port, respectively.

In some embodiments, the first sealing element 7126, the second sealing element 7128, or both can be further configured to limit the direction of airflow while also providing sealed access for the surgical instruments through the seal housing 7100. This can prevent contamination from aerosolized viruses or contagions during treatment due to the advancement and extraction of surgical instruments through the first port 7114 and/or the second port 7116. Additionally, the first sealing element, the second sealing element, or both can be a one-way valve to allow exhaust to be vented to a fluid trap and particulate filter to control the expiration of contagions. In another exemplary embodiment, the surgical sealing device 7000 can have a small higher pressure inlet and a larger exhaust port for controlling exhaust gases being expelled from the natural body lumen.

In addition to the insertion and extraction of one or more surgical instruments through the first and second ports 7114, 7116, fluid exchange can occur through the third port 7118 of the surgical sealing device 7000. That is, in this illustrated embodiment, the third port 7118 is designed to allow the ingress and egress of fluid between an interior volume of the natural body orifice and an ambient environment.

In certain embodiments, as shown in FIG. 22, the third port 7118 can be operatively connected to a valve 7210. The valve 7210 can be configured to monitor a parameter that can be used to control a fluid transfer rate through the third port 7118. The monitored parameter can be a fluid transfer pressure, a fluid transfer volume, and/or a direction of the fluid transfer therethrough. For example, the valve can include a sensor that is configured to sense the pressure, volume, or flow direction of the fluid as it passes through the valve, and transmit the sensed data to a controller (not shown). If at any time during use, the controller determines that the sensed data is outside of a predetermined range(s), the controller can alter the valve position (e.g., partially close or open the valve relative to its current position) to change the pressure, volume, or flow direction of the fluid therethrough, and consequently, through the third port 7118. Non-limiting examples of suitable sensors include pressure, temperature, and flow sensors. In other embodiments, a controller can be omitted, and the valve can be structurally configured to control the fluid flow therethrough by itself, and therefore alter the pressure, volume, or flow direction, if needed.

During an electrosurgical procedure, energy devices can delivery mechanical and/or electrical energy to target tissue in order to treat the tissue (e.g., to cut the tissue, cauterize blood vessels and/or coagulate the tissue within and/or near the targeted tissue). The cutting, cauterization, and/or coagulation of tissue can result in fluids and/or particulates being released into the air. Such fluids and/or particulates emitted during a surgical procedure can constitute smoke, for example, which can comprise carbon particles and/or other particles suspended in air. As a result, electrosurgical systems typically employ a surgical evacuation system that captures the resultant smoke from a surgical procedure, and directs the captured smoke through a filter and a smoke exhaust port away from the clinician(s) and/or from the patient(s).

For example, surgical procedures on a lung can require inhalation and expulsion of breathable air and exhaustion of smoke that is generated during the procedure. In such instances, cooperative control of the smoke evaluation and breathing apparatus can be helpful. As such, the surgical sealing devices disclosed herein can be configured to enable simultaneous trans-seal system use. That is, the present surgical sealing devices can be configured to provide smoke evacuation control of a fluid exchange system that allows cooperative flow of fluid such that, during surgery, the body can continue to receive the intended flow of fluid (e.g., breathable air) while also allowing extraction of a portion of the fluid through a different path to direct the smoke extraction from the patient.

In some embodiments, the smoke exhaust port can be its own separate port within the seal housing or it can be combined with another port of the seal housing (e.g., a port that is connected to a breathing apparatus that inflates and deflates the lung with breathable air and/or configured for insertion and extraction of surgical instruments), or the smoke evacuator passage can be a working passage of a flexible endoscope inserted through a port of the seal housing for controlling the ingress and egress of lung gasses as needed for breathing and smoke evacuation. If the smoke evacuation is activated when the body is breathing, an additional airflow inlet can be configured as a port of the seal housing to offset the smoke evacuation air flow, resulting in enough air for lung inflation while cooperatively extracting smoke and air form the lung. In some embodiments, the smoke evacuation system can be configured to pass the smoke to an externally connected smoke evacuator pump and filters, while in other embodiments, the smoke evacuation system can be arranged to use the same filters as a primary breathing exhaust system coupled to the breathing passage port of the seal housing. Exemplary smoke evacuator systems suitable for use with the present disclosure are described, for example, in U.S. Pat. No. 11,051,876 entitled "Surgical Evacuation Flow Paths" issued Jul. 6, 2021, U.S. Patent Publication No. 2019/0201088 entitled "Surgical Evacuation System With A Communication Circuit For Communication Between A Filter And A Smoke Evacuation Device" published Jul. 4, 2019, and U.S. Patent Publication No. 2019/0204201 entitled "Adjustments Based On Airborne Particle Properties" published Jul. 4, 2019, the disclosures of which are incorporated herein by reference in their entireties.

Figure 25:
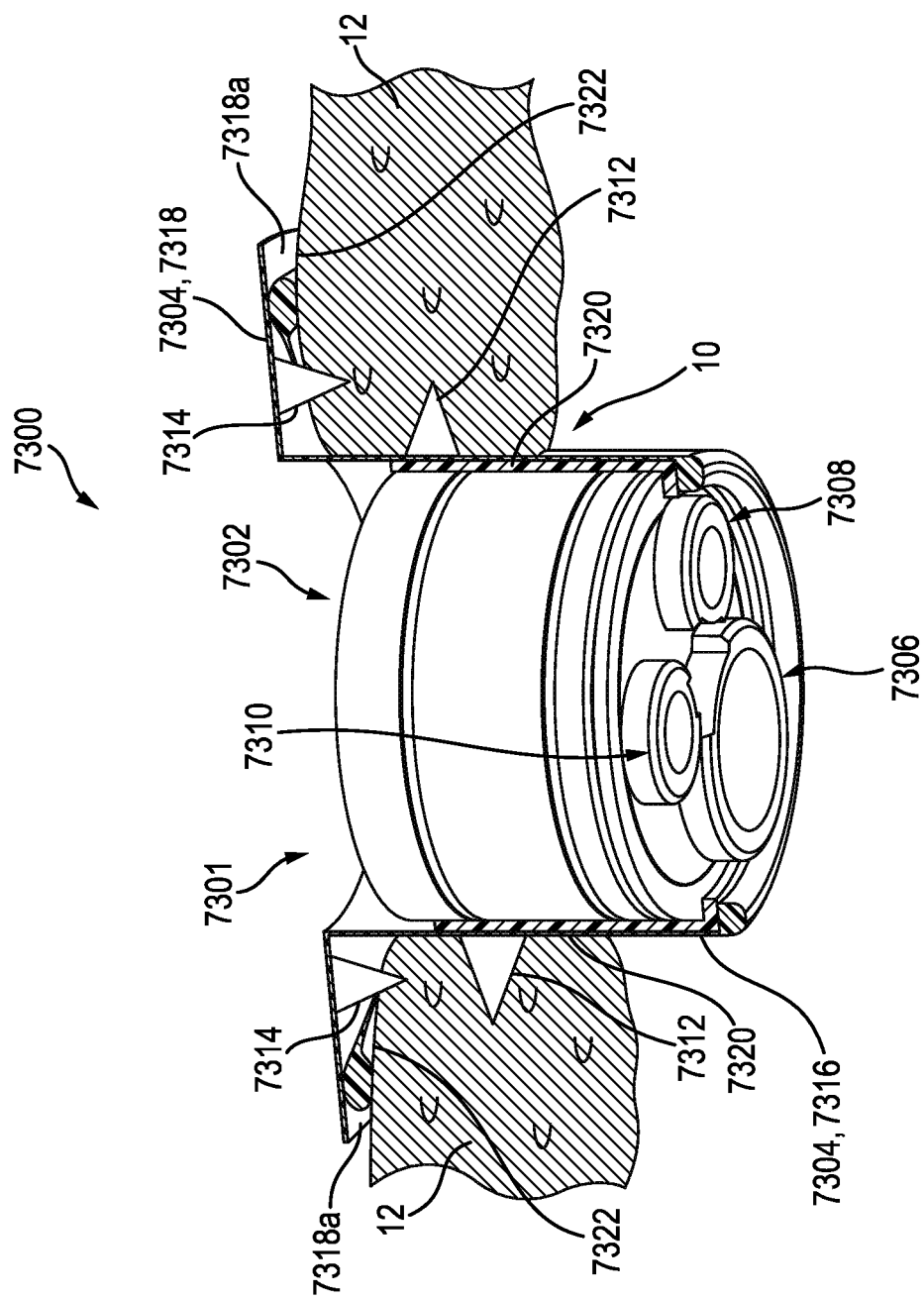
FIG. 25 is a cross-sectional view of another exemplary embodiment of a surgical sealing device, showing the device inserted into a natural body orifice.

FIG. 25 illustrates another embodiment of a surgical sealing device 7300. Aside from the differences described in detail below, the surgical sealing device 7300 can be similar to surgical sealing device 7000 (FIG. 22 and FIG. 23) and therefore common features are not described in detail herein. The surgical sealing device 7300 is shown at least partially inserted within a natural body orifice 10 formed by tissue 12. The surgical sealing device 7300 includes a seal housing 7301 having an inner body member 7302 and an outer body member 7304 that is positioned about the inner body member 7302. The inner body member 7302 has three ports 7306, 7308, 7310 extending therethrough. While different numbers and sizes of ports can be used, the illustrated three ports 7306, 7308, 7310 include one relatively larger port 7306 (e.g., to receive an endoscope or other relatively larger diameter device), and two relatively smaller ports 7308, 7310 (e.g., to receive relatively smaller devices, such as graspers, clip appliers, or the like).

Further, the seal housing 7301 includes first retention elements 7312 and second retention elements 7314. As shown, the first retention elements 7312 extend outward from the elongated cylindrical base 7316 of the outer body member 7304 and the second retention elements 7314 extend from a bottom surface 7318a of the annular flange 7318 of the outer body member 7304. The first retention elements 7312 engage with an internal surface 7320 of the natural body orifice 10 and penetrate portions of the tissue 12 that define such internal surface 7320. Since the surgical sealing device 7300 is only partially inserted into the natural body orifice 10, the annular flange 7318 of the seal housing 7300 is positioned outside of the natural body orifice 10. As a result, the second retention elements 7314 engage an outer tissue surface 7322 surrounding the natural body orifice 10 and penetrate portions of the tissue 12 that define such outer surface 7322 (e.g., external surface of the natural body lumen). This penetration by both the first and second retention elements 7312, 7314 into the tissue 12 affix the seal housing 7301 to the natural body orifice 10 so as to allow one or more surgical instruments to be inserted and extracted through the natural body orifice 10 and/or fluid transfer to occur through the natural body orifice 10.

In some embodiments, the surgical sealing device can include wound protectors for use with natural body orifices that enable introduction and extraction of instruments while limiting instrument to tissue interaction. This limiting of interaction between the tissue and instruments can provide reduced friction between the body wall and the insertion forces of the instruments. The arrangement can minimize damage to the surrounding tissue during manipulation or advancing or retracting of the instruments through the sealing device.

In some embodiments, the seal housing of the surgical sealing device can be configured as a mechanical fixation point for a flexible scope and/or instruments passing through the seal housing. The seal housing can be arranged such that a fixation point is formed by the seal housing being secured within the natural body orifice, which provides the flexible scope and/or instruments passing through the seal housing a resistive fixation point from which to resist internally generated forces, motions and actions from the instruments manipulating tissue within the body. The fixation point for the instruments would prevent inappropriate loads on the patient during movement of the instruments within the sealing device. The fixation point could be outside of the body and prevent excessive torque from being applied to the body by the instruments through the sealing device.

While the seal housings 7100, 7402, 7301 in FIG. 22 and FIG. 23, FIG. 24, and FIG. 25 are illustrated as a separate device which to be inserted into a natural body orifice and allows instruments to be inserted therethrough and into a natural body lumen, in other embodiments a seal housing can be arranged on an instrument, such as a gastroscopic bougie, as the instrument is inserted into a natural body orifice. A gastroscopic bougie is commonly understood to be a thin cylinder of rubber, plastic, metal or another material that a medical practitioner inserts into or through a body passageway, such as the esophagus, to diagnose or treat a condition. A bougie may be used to widen a passageway, guide another instrument into a passageway, or dislodge an object. The gastroscopic bougie can include a seal housing having retention elements which are configured to be deployed in the esophagus prior to the stomach. This arrangement would allow laparoscopic access to the stomach while the abdominal cavity is insufflated for procedures such as a tumor resection within the stomach. By arranging the seal housing in the esophagus, the laparoscopic insufflation is prevented from escaping endoluminally, while also allowing bougie to manipulate the stomach and tumor through four-wire control.

Surgical Systems with Port Devices for Instrument Control

In certain embodiments, surgical systems that enable control of surgical instrument interactions between separate port devices are provided. In general, these systems have two or more port devices (e.g., multi-port devices) that include respective housings that are each configured to allow instruments from respective sets of instruments to be inserted therethrough. The two or more port devices are each designed to provide individualized resistive forces to respective inserted instruments and to allow the inserted instruments to work cooperatively together (e.g., for at least one surgical step of a surgical procedure or at one or more surgical sites, etc.). The two or more port devices are interconnected to each other (e.g., electrically or mechanically) to create an interrelationship between the inserted instruments. This interrelationship enables these instruments to work in combination (e.g., move concurrently or sequentially in the same or different direction relative to each other or in groups) to provide the force(s), retraction, access angle(s), and the like to carry out at least one surgical step (e.g., to provide the intended medial therapy). As a result, these cooperative movements between at least a portion of the inserted instruments can provide a more collaborative surgical environment within the same port or among different ports that can increase precision and help prevent collisions (e.g., of surgical instruments and/or robotic arms).

A person skilled in the art will understand that the phrase "work cooperatively together" as used herein refers to coordinated movement between two or more inserted instruments in the same port, in separate ports, or a combination thereof based on a location, an orientation, or a motion of at least one inserted instrument of the two or more inserted instruments. Similarly, a person skilled in the art will understand that the coordinated movement between the two or more inserted instruments can occur in the same direction at the same time, in the same direction at different times, opposing directions at the same time, opposing directions at different times, in the same plane at the same time, in the same plane at different times, in two separate planes at the same time, in two different planes at different times, or any combination thereof.

Each port device is configured to be at least partially disposed with a body. For example, a first port device can be partially inserted into a body (e.g., through a natural orifice or an opening made by an incision) and a second port device can be partially inserted into the (e.g., through a natural orifice or an opening made by an incision). The first and second port devices can be partially inserted within the same physiological space or different physiological spaces. In some embodiments, the first port device can bridge the ambient environment with a first physiological space inside the body (e.g., thoracic cavity or abdomen cavity and the second port device can bridge the ambient environment and a second physiological space that is not directly connected to the first physiological space (e.g., through a natural orifice to inside the colon, esophagus or other physiologic tract). In other embodiments, the first and second physiological spaces are directly connected to each other. For example, in one embodiment, the first port device can be partially inserted into a first abdominal quadrant and the second port device can be partially inserted into a second abdominal quadrant that is different than the first abdominal quadrant.

The housing of each port device can be positioned and affixed to body in such a way in which a distal portion of the housing extends into the body (e.g., a physiological space), and a proximal portion extends out of the body and into the ambient environment (e.g., positioned adjacent to and in contact with an exterior surface of the patient's body, such as the patient's skin). Alternatively, the housing can be designed to be entirely positioned within the body.

Further, the housing of each port device generally includes ports arranged within the housing that allow instruments to be inserted therethrough into the body (e.g., a physiological space, such as a one or more cavities within the body) from the ambient environment through a natural body orifice or an opening made by an incision. The ports arranged through the housing can form pathway(s) into and through the body.

In some embodiments, at least one port of at least one port device can be configured to form a seal around an inserted instrument. In one embodiment, at least one port of the first port device can be configured to form a seal around a respective inserted instrument of a first set of instruments. Alternatively, or in addition, at least one port of the second port device can be configured to form a seal around a respective inserted instrument of a second set of instruments.

In certain embodiments, sealing element(s) can be positioned within the at least one port to form a seal therein. The sealing element(s) can have a variety of configurations. In some embodiments, the sealing element(s) can be in the form of a thin membrane formed of a flexible material which can be punctured or otherwise pierced by a surgical instrument. Alternatively, or in addition, zero closure sealing elements such as a duck bill seal or other suitable seals for sealing in the absence of instrument can be used in association with the at least one port. The sealing elements can be positioned at any suitable location within the at least one port.

In some embodiments, when first and second instruments are inserted into respective ports of the first port device, the first port device can be configured to allow the first instrument to move within a first range of motion relative to the first port device and to allow the second instrument to move within a second range of motion relative to the first port device that is at least partially overlaps with the first range of motion. Alternatively, or in addition, when first and second instruments are inserted into respective ports of the second port device, the second port device can be configured to allow the first instrument to move within a first range of motion relative to the second port device and to allow the second instrument to move within a second range of motion relative to the second port device that at least partially overlaps with the first range of motion.

In use, as discussed in more detail below, the respective port device provides resistive inter-device forces to respective inserted instruments (e.g., to prevent unintended contact between inserted instruments). That is, during movement of an inserted instrument, the port device can restrain movement of the inserted instrument relative to other inserted instruments in the same port device, in at least one other port device, or a combination thereof. The port device(s) of the surgical system are configured to interact at least one inserted instrument in such a way that limits one or more instrument motions. This limitation can be based on, for example, at least one of a location, orientation, and a motion of at least one other instrument of the same set of inserted instruments, at least one other instrument of a different set of inserted instruments, or both.

The location, orientation, motion, or any combination thereof, of an inserted instrument can be determined, for example, by using one or more tracking device(s) or a tracking system. In some embodiments, the system can include a tracking device that can be associated with one of the first port device or the second port device. The tracking device can be configured in a variety of ways. In certain embodiments, the tracking device can be configured to transmit a signal indicative of a location of the first port device relative to the second port device. Alternatively, or in addition, the tracking device can be configured to transmit a signal indicative of at least one of a location, an orientation, and a motion of at least one inserted instrument in the first port device relative to the second port device. Alternatively, or in addition, the tracking device can be configured to transmit a signal indicative of at least one of a location, an orientation, and a motion of at least one inserted instrument in the second port device relative to the first port device.

The transmitted signal(s) from the tracking device can be received by a controller. In general, depending on the data of the received signal, the controller can determine at least one or more of the following: a relative location of the first port device and the second port device, at least one of the location, the orientation, and the motion of at least one inserted instrument in the first port device relative to the second port device, or at least one of the location, the orientation, and the motion of the at least one inserted instrument of in the second port device relative to the first port device based on the respective transmitted signal. This information is used as guidance for movement of the inserted instruments individually, as a single group, or as multiple groups. This guidance in combination with the resistive forces applied by the respective port devices can control instrument interaction between the inserted instruments such that the inserted instruments can work cooperatively together at one or more surgical sites and/or to perform at least one surgical step of a surgical procedure.

An exemplary surgical system can include a variety of features as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the surgical systems are shown and described in connection with a colon, a person skilled in the art will appreciate that these surgical systems can be used in connection with any other suitable natural body lumens or organs.

Figure 26:
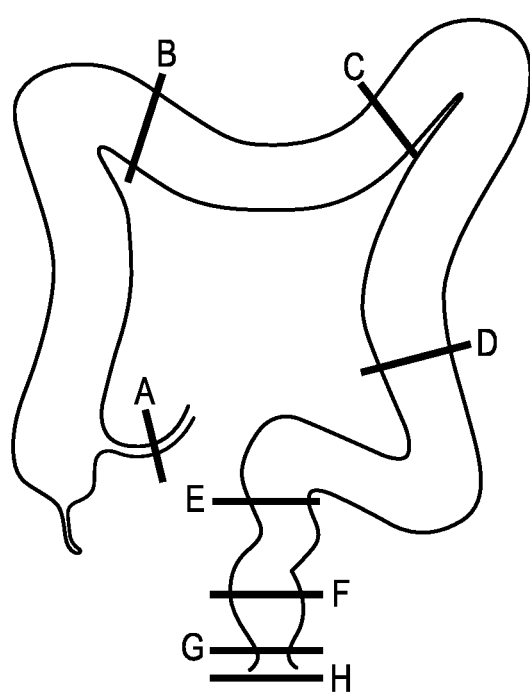
FIG. 26 is an exemplary image of a colon.

Surgery is often the primary treatment for early-stage colon cancers. The type of surgery used depends on the stage (extent) of the cancer, its location in the colon, and the goal of the surgery. Some early colon cancers (stage 0 and some early stage I tumors) and most polyps can be removed during a colonoscopy. However, if the cancer has progressed, a local excision or colectomy, a surgical procedure that removes all or part of the colon, may be required. In certain instances, nearby lymph nodes are also removed. A hemicolectomy, or partial colectomy, can be performed if only part of the colon is removed. In a segmental resection of the colon the surgeon removes the diseased part of the colon along with a small segment of non-diseased colon on either side. Usually, about one-fourth to one-third of the colon is removed, depending on the size and location of the cancer. Major resections of the colon are illustrated in FIG. 26, in which (i) A-B is a right hemicolectomy, A-C is an extended right hemicolectomy, B-C is a transverse colectomy, C-E is a left hemicolectomy, D-E is a sigmoid colectomy, D-F is an anterior resection, D-G is a (ultra) low anterior resection, D-H is an abdomino-perineal resection, A-D is a subtotal colectomy, A-E is a total colectomy, and A-H is a total procto-colectomy. Once the resection is complete, the remaining intact sections of colon are then reattached.

During a laparoscopic-assisted colectomy procedure, it is often difficult to obtain an adequate operative field. Often times, dissections are made deep in the pelvis which makes it difficult to obtain adequate visualization of the area. As a result, the lower rectum must be lifted and rotated to gain access to the veins and arteries around both sides of the rectum during mobilization. During manipulation of the lower rectum, bunching of tissue and/or overstretching of tissue can occur. Additionally, a tumor within the rectum can cause adhesions in the surrounding pelvis, and as a result, this can require freeing the rectal stump and mobilizing the mesentery and blood supply before transection and removal of the tumor.

After a colectomy, the remaining healthy portions of the colon must be reattached to one another to create a path for waste to leave the body. However, when using laparoscopic instruments to perform the colectomy, one single entry port device may not have a large enough range of motion to move the one end of the colon to connecting portion. As such, a second entry port device is therefore needed to laparoscopically insert instruments to help mobilize the colon and/or purchase the one end of the colon from a laparoscopic instrument of the first entry port device and move the one end to the connecting portion. The multiple port devices having multiple instrument inserted therethrough to carry out at least one surgical step or site can increase the chance of surgical errors and collisions between surgical instruments or robotic arms.

The present surgical systems include multiple port devices (e.g., multi-port devices) that interconnect multiple groups of surgical instruments that can move together while also providing individualized resistive inter-device forces and motions to the surgical instruments. For example, a first port device can be configured to receive a first set of instruments (e.g., two or more instruments) and a second port device can be configured to receive a second set of instruments (e.g., two or more instruments), and when at least one instrument from the first set and from the second set are inserted into the first and second port devices, respectively, these instruments can move together as a single group. Alternatively, or in addition, at least one inserted instrument of the first set can move with at least one instrument of the second set, or vice versa.

Figure 27:
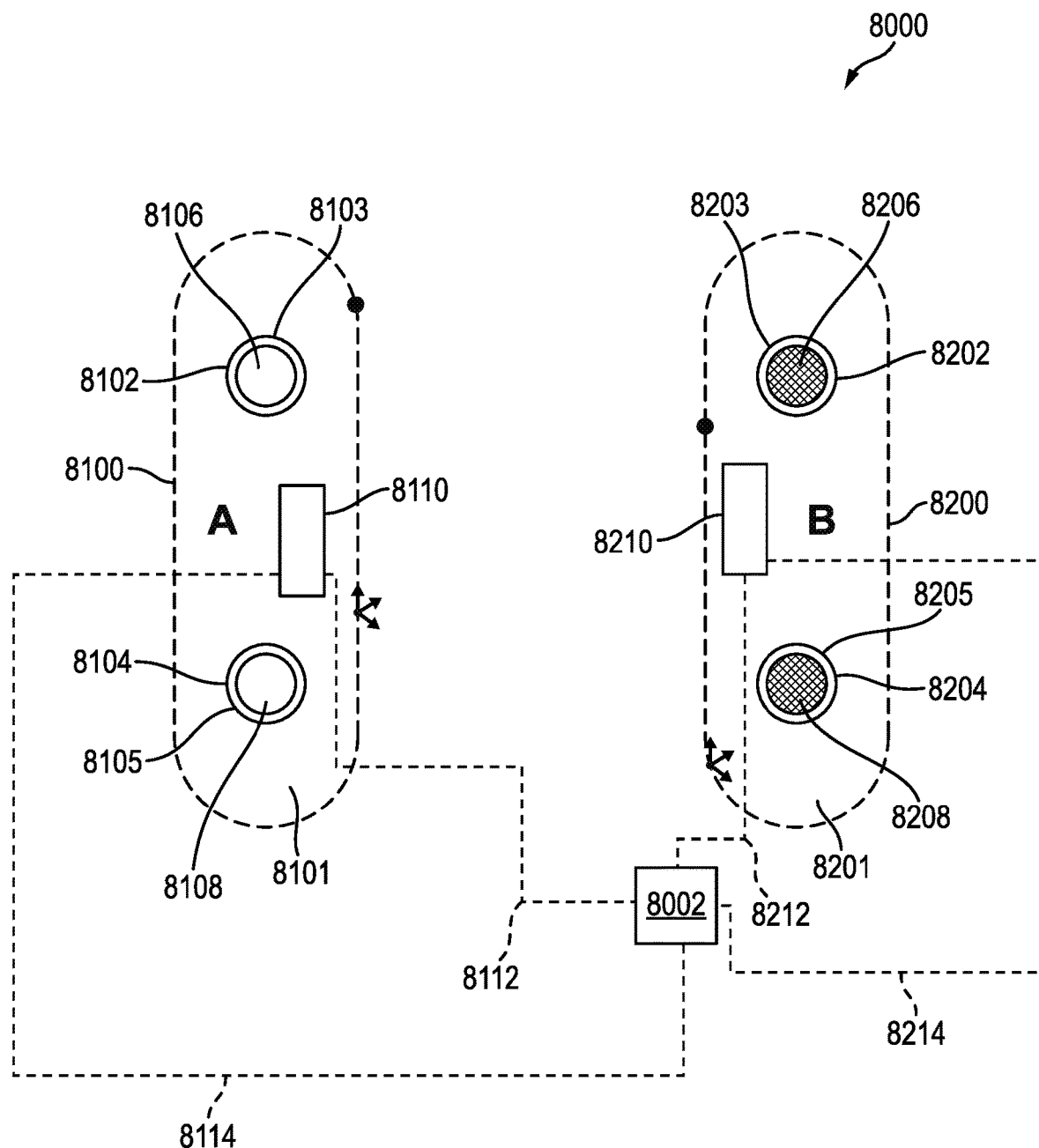
FIG. 27 is a schematic view of an exemplary embodiment of a surgical system having first and second multi-port devices.
Figure 28:
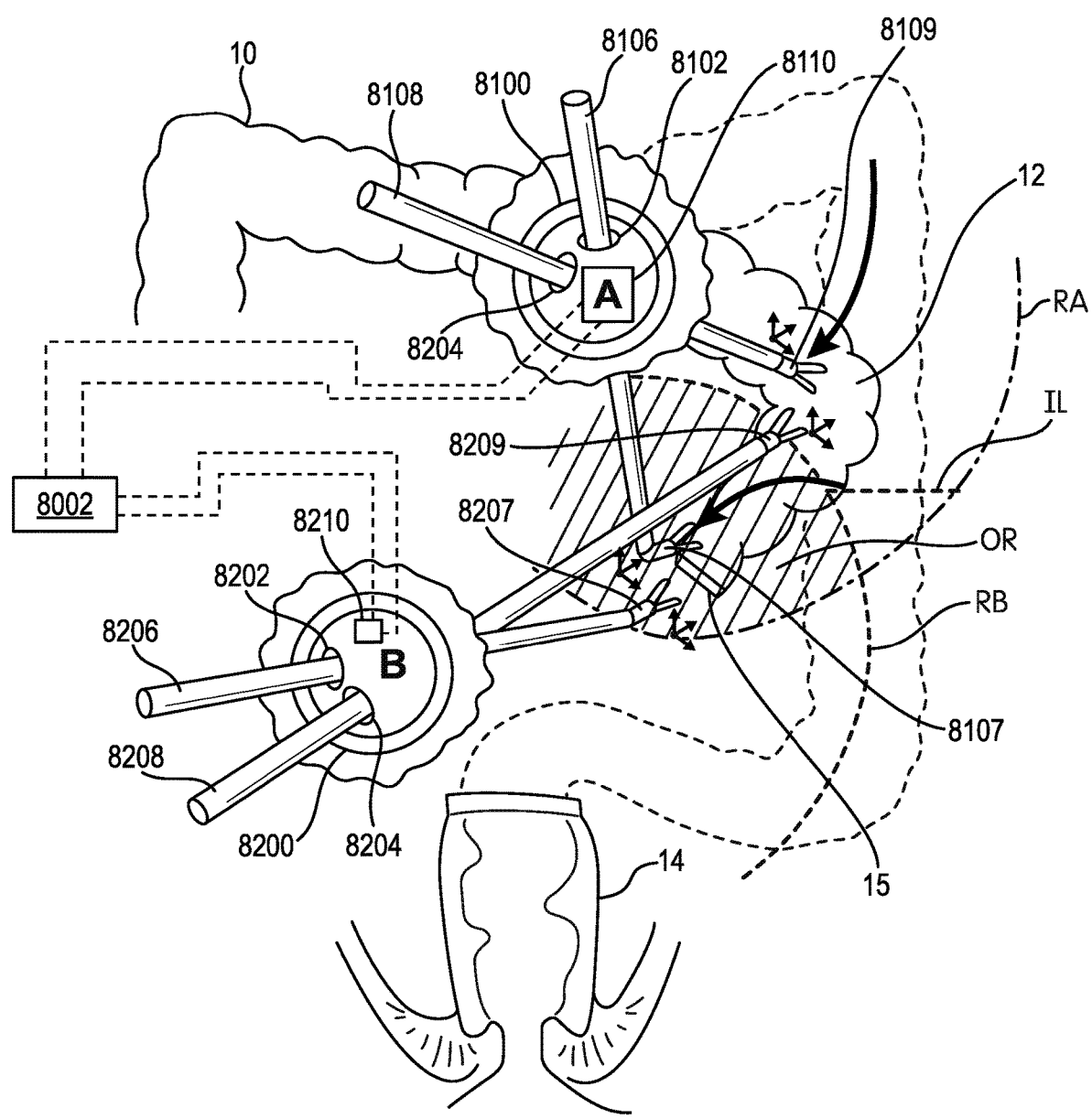
FIG. 28 is a schematic view of the surgical system of FIG. 27, showing the first and second multi-port devices partially inserted within an abdominal cavity.

FIG. 27 illustrates an exemplary embodiment a surgical system 8000 that is configured to for laparoscopic and/or endoscopic access into a body through two or more interconnected multi-port devices. FIG. 28 schematically illustrates the surgical system 8000 being used in a surgical resection procedure on a colon 10. For purposes of simplicity, certain components of the surgical system 8000 are not illustrated.

As shown, the surgical system 8000 includes a first multi-port device 8100 and a second multi-port device 8200, in which each multi-port device 8100, 8200 is configured to be at least partially disposed within the body. In other embodiments, the surgical system can include more than two multi-port devices. It is also contemplated herein that in addition to the multi-port devices, the surgical system can include one or more single port devices.

The first multi-port device 8100 can have a variety of configurations. For example, in some embodiments, as shown in FIG. 27 and FIG. 28, the first multi-port device 8100 includes a first housing 8101 with a first port 8102 and a second port 8104 defined therein. The first and second ports 8102, 8104 are each configured to allow a respective surgical instrument to be inserted therethrough. For example, a first instrument 8106 (shown in more detail in FIG. 28) can be inserted into the first port 8102 and a second instrument 8108 (show in more detail in FIG. 28) can be inserted into the second port 8104. The first and second instruments 8106, 8108 are collectively referred to herein as "a first set of instruments."

In use, the first multi-port device 8100 interacts with the first instrument 8106, the second instrument 8108, or both. The first multi-port device 8100 can be configured to interact with the first instrument 8106 and the second instrument 8108 concurrently, separately, or both. By way of example, the first multi-port device 8100 interacts with the first instrument 8106, and during the interaction, the first multi-port device 8100 applies resistive forces to the first instrument 8106. These resistive forces limit one or more motions of the first instrument 8106 based on at least one of a location, orientation, and a motion of the second instrument 8108. A person skilled in the art will understand that the first multi-port device 8100 is configured to have a similar interaction with the second instrument 8108.

The first housing 8101 can be formed of one or more suitable material(s). In some embodiments, a first portion of the first housing can be formed of at least one first material and a second portion of the first housing can be formed of at least one second material. In such embodiments, the first portion can be more flexible than the second portion or vice versa. In other embodiments, the first housing is uniformly formed of one or more suitable material(s). A person skilled in the art will understand that the amount and type of resistive forces the first multi-port device applies to any inserted instrument will depend at least upon the material(s) and structural configuration of the first housing and the amount of force and the direction of force applied to the respective port by the inserted instrument.

The first and second ports 8102, 8104 can be configured to form a seal around an instrument inserted therethrough. For example, a first sealing element 8103 and a second sealing element 8105 can be positioned within the first port 8102 and the second port 8104, respectively. The sealing elements 8103, 8105 can be formed of any suitable material(s). A person skilled in the art will understand that the amount and type of resistive forces the first multi-port device applies to any inserted instrument will depend at least upon the material(s) and structural configuration of any sealing element(s) disposed within the first and second ports of the first housing.

In use, the first and second sealing elements 8103, 8105 form a seal around first and second instruments 8106, 8108, respectively. This can allow the physiological space inside the body to remain insufflated as the first and second instruments 8106, 8108 and/or other suitable instrument(s) are inserted and removed from the first multi-port device 8100. In certain embodiments, one or more of the inserted instruments of the first multi-port device 8100 can pivotally move relative to the first housing 8101.

The second multi-port device 8200 can have a variety of configurations. For example, in some embodiments, as shown in FIG. 27, the second multi-port device 8200 includes a second housing 8201 with a third port 8202 and a fourth port 8204 defined therein. The third and fourth ports 8202, 8204 are each configured to allow a respective instrument to be inserted therethrough. For example, a third instrument 8206 (shown in more detail in FIG. 28) can be inserted into the third port 8202 and a fourth instrument 8208 (shown in more detail in FIG. 28) can be inserted into the fourth port 8204. The third and fourth instruments 8206, 8208 are collectively referred to herein as "a second set of instruments."

In use, the second multi-port device 8200 interacts with the third instrument 8206, the fourth instrument 8208, or both. The second multi-port device 8200 can be configured to interact with the third instrument 8206 and the fourth instrument 8208 concurrently, separately, or both. By way of example, the second multi-port device 8200 can interact with the third instrument 8206, and during this interaction, the second multi-port device 8200 applies resistive forces to the third instrument 8206. These resistive forces limit one or more motions of the third instrument 8206 based on at least one of a location, orientation, and a motion of the fourth instrument 8208. A person skilled in the art will understand that the second multi-port device 8200 is configured to have a similar interaction with the fourth instrument 8208.

The second housing 8201 can be formed of one or more suitable material(s). In some embodiments, a first portion of the second housing can be formed of at least one first material and a second portion of the second housing can be formed of at least one second material. In such embodiments, the first portion can be more flexible than the second portion or vice versa. In other embodiments, the second housing is uniformly formed of one or more suitable material(s). A person skilled in the art will understand that the amount and type of resistive forces the second multi-port device applies to any inserted instrument will depend at least upon the material(s) and structural configuration of the second housing and the amount of force and the direction of force applied to the respective port by the inserted instrument.

The third and fourth ports 8202, 8204 can be configured to form a seal around an instrument inserted therethrough. For example, a third sealing element 8203 and a fourth sealing element 8205 can be positioned within the third port 8202 and the fourth port 8204, respectively. The third and fourth sealing elements 8203, 8205 can be formed of any suitable material(s). A person skilled in the art will understand that the amount and type of resistive forces the second multi-port device applies to any inserted instrument will depend at least upon the material(s) and structural configuration of any sealing element(s) disposed within the third and fourth ports of the second housing.

In use, the third and fourth sealing elements 8203, 8205 form a seal around third and fourth instruments 8206, 8208, respectively. This can allow the physiological space inside the body to remain insufflated as the third and fourth instruments 8206, 8208 and/or other suitable instrument(s) are inserted and removed from the second multi-port device 8200. In certain embodiments, one or more of the inserted instruments of the second multi-port device 8200 can pivotally move relative to the second housing 8201.

Further, the first multi-port device 8100 and/or the second multi-port device 8200 can incorporate various tracking mechanisms, such as electromagnetic (EM) tracked tips, fiber bragg grating, various sensors, etc., to assist in tracking orientation, location, and movement of the instruments. For example, the first multi-port device 8100 and the second multi-port device can include a first tracking device 8110 and a second tracking device 8210, respectively. Each of the first and second tracking devices 8110, 8210 can be configured to transmit a variety of signals that can be used to determine the relative location of the first and second multi-port devices 8100, 8200, at least one of a location, an orientation, and a motion of at least one instrument inserted into one of the first or second multi-port devices 8100, 8200 relative to the other one of the first or second multi-port devices 8100, 8200 or relative to at least one instrument inserted into the other one of the first or second multi-port devices 8100, 8200, or a combination thereof.

In use, with respect to the first tracking device 8110, as the third and fourth instruments 8206, 8208 are inserted into the second multi-port device and moved within the body, the first tracking device 8110 is configured to transmit a first signal 8112 to a controller 8002 that includes sensed data associated with the third instrument 8206, the fourth instrument 8208, or the second set of instruments. That is, the first tracking device 8110 is configured to sense, or otherwise track, the third instrument 8206, the fourth instrument 8208, or both (e.g., the second set of instruments), as such instrument(s) is/are inserted into and moved in the body with or relative to the second multi-port device 8200. Alternatively, or in addition, the first signal 8112 or an additional signal can include sensed data associated with the second multi-port device 8200. The first tracking device 8110 is also configured to transmit a second signal 8114 to the controller 8002 that includes sensed data associated with the first set of instruments and/or the first multi-port device 8100 itself.

Once the first and second transmitted signals 8112, 8114 are transmitted to and received by the controller 8002, the controller 8002, based on these signals, can calculate location, position, or motion of the third instrument 8206, the fourth instrument 8208, or both, relative to the first set of instruments and/or the first multi-port device 8100 itself. This creates one or more interrelationships between the first and second sets of instruments, and as a result, at least a portion of the first and second sets of instruments can work cooperatively together at one or more surgical sites and/or to carry out at least one surgical step of a surgical procedure. As shown in FIG. 28, and as described in more detail below, the first instrument 8106 and the third instrument 8206 are working cooperatively together to handoff the free end 15 of the colon 10, and the second instrument 8108 and the fourth instrument 8208 are shown working cooperatively together to purchase the same area of the colon 10.

Similarly, with respect to the second tracking device 8210, in use, as the first and second instruments 8106, 8108 are arranged within the body, the second tracking device 8210 is configured to transmit a third signal 8212 to the controller 8002 that includes sensed data associated with the first instrument 8106, the second instrument 8108, or the first set of instruments. That is, the second tracking device 8210 is configured to sense, or otherwise track, the first instrument 8106, the second instrument 8108, or both (e.g., the first set of instruments), as such instrument(s) is/are inserted into and moved within the body with or relative to the first multi-port device 8100. Alternatively, or in addition, the third signal 8212 or an additional signal can include sensed data associated with the first multi-port device 8100. The second tracking device 8210 is also configured to transmit a fourth signal 8214 to the controller 8002 that includes sensed data associated with the second set of instruments and/or the second multi-port device 8200 itself.

Once the third and fourth transmitted signals 8212, 8214 are transmitted to and received by the controller 8002, the controller 8002, based on these signals, can calculate location, position, or motion of the first instrument 8106, the second instrument 8108, or both, relative to the second set of instruments and/or the second multi-port device 8200 itself. This also creates one or more additional interrelationships between the first and second sets of instruments, and as a result, at least a portion of the first and second sets of instruments can work cooperatively together at one or more surgical sites and/or to carry out at least one surgical step of a surgical procedure.

The tracking mechanism of the first and second tracking devices 8110, 8210 can be any suitable mechanism. For example, the first tracking device 8110 can be configured to use magnetic sensing to detect a location, an orientation, or a motion of the third instrument 8206, the fourth instrument 8208, or both relative to the first multi-port device 8100 and/or to determine a location of the second multi-port device 8200 relative to the first multi-port device 8100. In such instances, the third instrument 8206, the fourth instrument 8208, or both and/or the second multi-port device 8200 includes a respective magnetic fiducial marker (not shown) that is configured to emit a respective magnetic field that can be detected by the first tracking device 8110. Alternatively, or in addition, the second tracking device 8210 can be configured to use a similar magnetic sensing mechanism to detect a location, an orientation, or a motion of at least one of the first and second instruments 8106, 8108 relative to the second multi-port device 8200 and/or to determine a location of the first multi-port device 8100 relative to the second multi-port device 8200. In some embodiment, a magnetic tracking system is configured to output a defined directional field relative to the magnet, its orientation, and near-by metallic systems. When the magnet is a permanent magnet, the field is of a predefined intensity, size, and orientation. Since the field is vector directional, a magnetic sensor within the directional field is configured to sense from the intensity, direction of the magnet vectors, and change of those measures over time where the sensor is within the directional field and orientation of the sensor with respect to the magnet. When the magnet is an electro-magnet, the intensity and field direction can be alternated and changed as directed, which mitigates metal impacts on the field and interferences as well as increase accuracy. "DESIGN OF A MAGNETIC FIELD-BASED MULTI DEGREE-OF-FREEDOM ORIENTATION SENSOR USING THE DISTRIBUTED-MULTIPLE-POLE MODEL" from Proceedings of IMECE2007 2007 ASME International Mechanical Engineering Congress and Exposition Nov. 11-15, 2007, Seattle, Washington, USA illustrates and describes multi-degree freedom magnetic field tracking.

For another example, the first tracking device 8110 can be configured to use common anatomic landmarks to detect a location, an orientation, or a motion of the third instrument 8206, the fourth instrument 8208, or both relative to the first multi-port device 8100 and/or a location of the second multi-port device 8200 relative to the first multi-port device 8100. Alternatively, or in addition, the second tracking device 8210 can be configured to use common anatomic landmarks to detect a location, an orientation, or a motion of at least one of the first and second instruments 8106, 8108 relative to the second multi-port device and/or a location of the first multi-port device 8100 relative to the second multi-port device 8200. In some embodiments, the use of physiologic landmarks, and the distances and focal aspects of these landmarks with respect to an imaging system enable the imaging system to use the same imaging and distance measurements to determine the location and orientation of the instruments with respect to the anatomic location. These "reference" points would enable the system to using imaging & pre-operative imaging to scale the measures allowing them to more accurately correct for focus or depth measures of the system. In certain embodiments, 3D imaging systems and/or Lidar imaging systems can both be used to enhance or replace the optical measurements with respect to the surgical sites.

For yet another example, a structured light scan can be used to create a 3D map. Electromagnetic tracking of the first multi-port device 8100, the second multi-port device 8200 and the instruments 8106, 8108, 8206, 8208 (e.g., using one or more fiducial markers) provides 3D registration of the map. A perimeter can then be created around a critical structure using manual line or guides by confocal laser endomicroscopy to provide real time histology guidance. A line as registered in space can be communicated to the first multi-port device 8100 and the first and second instruments 8106, 8108 located in a different quadrant of an abdominal cavity than the second multi-port device 8200 and third and fourth instruments 8206, 8208, for mobilizing the colon 10 between the quadrants. Alternatively, or in addition, a line as registered in space can be communicated to the second multi-port device 8200 and the third and fourth instruments 8206, 8208 for mobilizing the colon 10 between the quadrants.

Alternatively, for yet another example, the physical mechanical linkage angles between robotic arms holding the surgical instruments and their predefined lengths can be used to enhance a visual system's calculation of depth and focal distance between surgical instruments and a surgical site. By using the linkage angles and predefined length, the system can achieve triangulation of the instruments within a patient in order to "calibrate" or compensate for optical losses by the imaging system.

For still another example, the first tracking device 8110 can be an optical sensor that can be configured to detect a fiducial marker on the third instrument, the fourth instrument, and/or the second multi-port device. Alternatively, or in addition, the second tracking device can be an optical sensor that is configured to detect a fiducial marker on the first instrument, the second instrument, and/or the first multi-port device. Any number of multi-ports and/or surgical instruments can be tracked in this way during performance of a surgical procedure.

In some embodiments, controlling cooperative surgical instrument interactions includes using smart device location cooperatively with scope tracking. In general, a non-magnetic sensing system can be used for 3D tracking to provide X, Y, Z coordinates using a single receiver and at least one emitter. A time-of-flight distance sensor system, discussed above, may thus be used.

For example, the non-magnetic sensing system can include ultrasonic sensor technology and radiofrequency (RF) sensor technology. A time of flight system can include an emitter and a receiver. To facilitate controlling cooperative surgical imaging interactions, the emitter includes an ultrasonic sensor (ultrasonic beacon) configured to transmit ultrasonic pulses, and the receiver includes an RF receiver configured to transmit an RF signal that commands the emitter to begin transmitting the ultrasonic pulses. The ultrasonic pulses are reflected back by object(s) within their range. The RF receiver is configured to record the ultrasonic pulses and to, based on the recorded ultrasonic pulses, calculate 3D coordinates (X, Y, Z) of the emitter. The sound propagation time of the ultrasonic pulses allows the RF receiver to calculate the 3D coordinates and to calculate distance to objects.

FIG. 28 illustrates a schematic view of the surgical system 8000 being used during a colon resection procedure. As explained above, the first tracking device 8110 of the first multi-port device 8100 can track the third instrument 8206, the fourth instrument 8208, or both, and the second tracking device 8210 of the second multi-port device 8200 can track the location of first instrument 8106, the second instrument 8108, or both, while the instruments are inserted into their respective port devices and arranged within the body. Further, the first and second instruments 8106, 8108 can include first and second graspers 8107, 8109, respectively, and third and fourth instruments 8206, 8208 can include third and fourth graspers 8207, 8209, respectively, to grasp the colon 10 and the mobilized section 12 thereof and help reattach the mobilized section 12 to the rectum 14.

As shown in FIG. 28, the first and second instruments 8106, 8108 passing through the first multi-port device 8100 are arranged in the upper left quadrant of the abdominal cavity to mobilize the transverse and descending colon 10. The third and fourth instruments 8206, 8208 passing through the second multi-port device 8200 are arranged in the lower left quadrant of the abdominal cavity to mobilize and create an incision along line IL to remove a tumor in the descending colon or sigmoid. Each set of instruments is accessing the abdominal cavity together through respective multi-port devices 8100, 8200, which allow for interrelating the instrument motions for each multi-port within its own quadrant. As illustrated, the first and second instruments 8106, 8108 have a first range of motion shown as dashed line RA, and the third and fourth instruments 8206, 8208 have a second range of motion shown as dashed line RB.

Due to the location of the first and second multi-port devices 8100, 8200 relative to each other and the resistive forces that are applied to the respective first and second sets of instruments during use, there is an overlapping range of motion shown as OR in which both sets of instruments can move within. As a result, based on the overlapping range of motion relative to the position of the colon, the instruments 8106, 8108, 8206, 8208 can interact during the handoff of the mobilization and retraction of the mobilized section 12 of the colon 10 transiting from the upper left quadrant to the lower right quadrant. Prior to and/or during the handoff, the first tracking device 8110 transmits the first and second signals 8112, 8114 to the controller 8002 and/or the second tracking device 8210 transmits the third and fourth signals 8212, 8214 to the controller 8002. The resulting interrelationship between the first and second multi-port devices 8100, 8200 (e.g., by way of the first and/or second tracking devices) enables triangulation and opposed motion of the instruments 8106, 8108, 8206, 8208 within their respective quadrant, as well as coordinated movement amongst at least a portion of the first and second set of instruments. As a result, the first and second sets of instruments work cooperatively together to interface with each other to control and/or stabilize the colon, or a portion thereof and/or to move the free end 15 toward the rectum for attachment. More specifically, as shown in FIG. 28, the second instrument 8108 and the fourth instrument 8208 are purchasing the same area of the colon 10, and the third instrument 8206 is ready to grasp the free end 15 of the colon 10 from the first instrument 8106 to move the free end 15 towards the rectum 14.

Any one or more of the exemplary surgical systems, port devices and related methods described herein, and variations thereof, can be implemented in conventional surgical procedures conducted by a medical professional as well as in robotic-assisted surgical procedures. Various teachings herein may be readily incorporated into a robotic surgical system such as one or more of the DAVINCI™ systems by Intuitive Surgical, Inc., of Sunnyvale, Calif., including their SP™ surgical system. Exemplary robotic surgical systems and related features, which may be combined with any one or more of the exemplary surgical access devices and methods disclosed herein, are disclosed in the following: U.S. Pat. No. 8,068,649, entitled "Method and Apparatus for Transforming Coordinate Systems in a Telemanipulation System," issued Nov. 29, 2011; U.S. Pat. No. 8,517,933, entitled "Retraction of Tissue for Single Port Entry, Robotically Assisted Medical Procedures," issued Aug. 27, 2013; U.S. Pat. No. 8,545,515, entitled "Curved Cannula Surgical System," issued Oct. 1, 2013; U.S. Pat. No. 8,551,115, entitled "Curved Cannula Instrument," issued Oct. 8, 2013; U.S. Pat. No. 8,623,028, entitled "Surgical Port Feature," issued Jan. 7, 2014, the disclosure of which is incorporated by reference herein; U.S. Pat. No. 8,771,180, entitled "Retraction of Tissue for Single Port Entry, Robotically Assisted Medical Procedures," issued Jul. 8, 2014, the disclosure of which is incorporated by reference herein; U.S. Pat. No. 8,888,789, entitled "Curved Cannula Surgical System Control," issued Nov. 18, 2014; U.S. Pat. No. 9,254,178, entitled "Curved Cannula Surgical System," issued Feb. 9, 2016; U.S. Pat. No. 9,283,050, entitled "Curved Cannula Surgical System," issued Mar. 15, 2016; U.S. Pat. No. 9,320,416, entitled "Surgical Instrument Control and Actuation," issued Apr. 26, 2016, the disclosure of which is incorporated by reference herein; U.S. Pat. No. 9,339,341, entitled "Direct Pull Surgical Gripper," issued May 17, 2016; U.S. Pat. No. 9,358,074, entitled "Multi-Port Surgical Robotic System Architecture," issued Jun. 7, 2016; U.S. Pat. No. 9,572,481, entitled "Medical System with Multiple Operating Modes for Steering a Medical Instrument Through Linked Body Passages," issued Feb. 21, 2017; U.S. Pat. No. 9,636,186, entitled "Multi-User Medical Robotic System for Collaboration or Training in Minimally Invasive Surgical Procedures," issued May 2, 2017; U.S. Pat. Pub. No. 2014/0066717, entitled "Surgical Port Feature," published Mar. 6, 2014, issued as U.S. Pat. No. 10,245,069 on Apr. 2, 2019, the disclosure of which is incorporated by reference herein; U.S. Pat. Pub. No. 2017/0128041, entitled "Laparoscopic Ultrasound Robotic Surgical System," published May 11, 2017; and U.S. Pat. Pub. No. 2017/0128144, entitled "Laparoscopic Ultrasound Robotic Surgical System," published May 11, 2017, the disclosure of which is incorporated by reference herein; and U.S. Pat. Pub. No. 2017/0128145, entitled "Laparoscopic Ultrasound Robotic Surgical System," published May 11, 2017. The disclosure of each of these references is incorporated by reference herein.

Surgical Sealing Systems for Instrument Stabilization

In various surgical procedures, a surgeon may need to direct two or more surgical instruments into a body cavity simultaneously in order to gain access to and provide effective treatment to tissue. It is generally desirable, however, to minimize the number of surgical openings that need to be formed in the patient (e.g., in a patient's abdominal wall) to thereby mitigate tissue trauma, cosmetic damage, and post-operation recovery time for the patient. Accordingly, surgical sealing systems are provided that generally include a sealing device having a seal housing with ports for receiving surgical instruments.

In general, the ports of the seal housing are designed to control or limit the motions of at least one instrument inserted through a respective port such that the instrument can stabilize another instrument inserted through a respective other port. Each of the ports can have a nominal size and shape and each can be configured to assume a selected size and/or shape that is different from the nominal size and/or shape. A person skilled in the art will understand that a nominal size and a nominal shape refer to a size and shape of a port without a force applied thereto. Similarly, a person skilled in the art will understand that a selected size and a selected shape of a port refers to a size and shape of a port when a force is applied to the port, such as by an instrument being inserted therethrough. It will be further understood by a person skilled in the art that the selected size and the selected shape will depend on the amount of force and the direction of force applied to the port, such as by the instrument.

The selected size and/or shape of each port can be constrained by the size and shape of each of the other plurality of ports. As a result, forces applied to one port can affect the size and shape of the other ports. The force can be applied by an instrument that is disposed within one port of the plurality of ports. The force applied thereto is therefore effective to change the size and/or shape of the ports based on the movement, direction, and force of the instrument. Since the ability to alter to the nominal shape of any one port is therefore constrained or limited by the size and/or shape of the other ports, a force applied to one instrument positioned within one of the plurality of ports is configured to stabilize at least one other instrument positioned within others of the plurality of ports.

Figure 29:
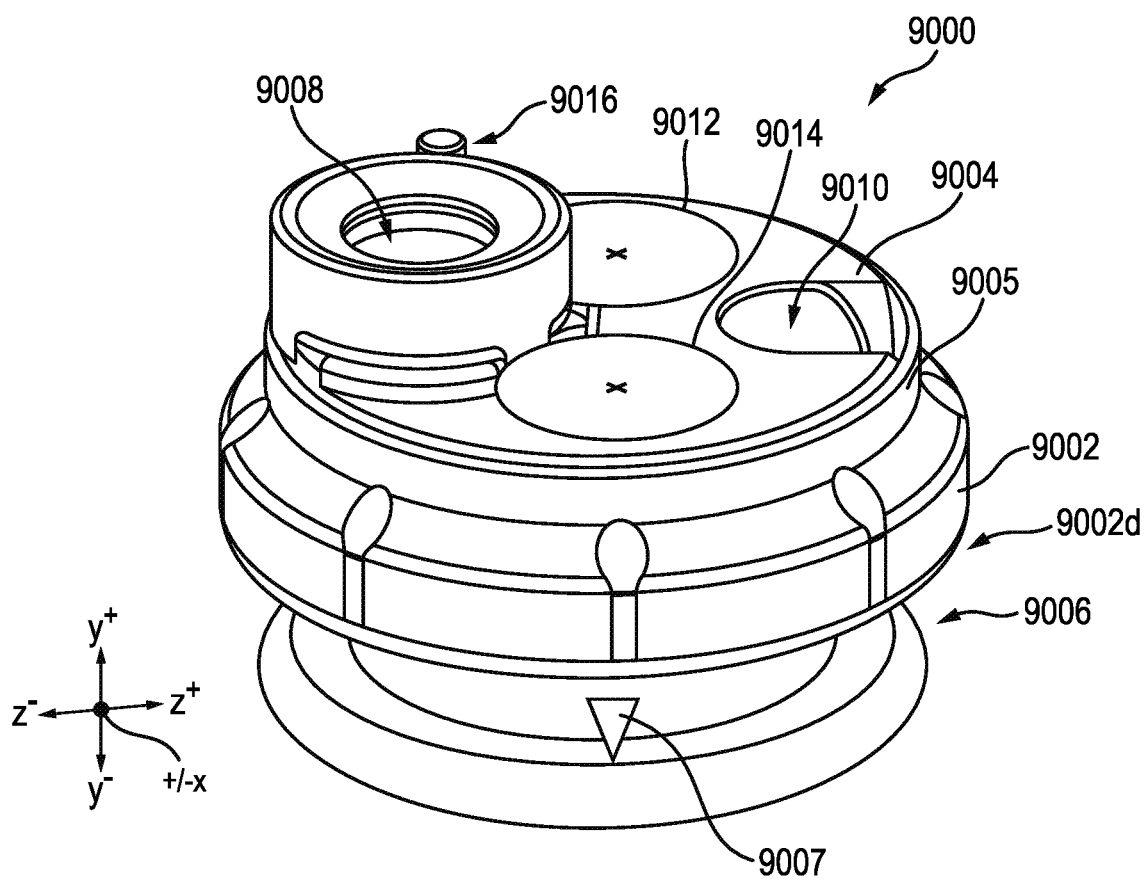
FIG. 29 is a schematic view of an exemplary embodiment of a surgical sealing system having a sealing device with ports extending therethrough.
Figure 30:
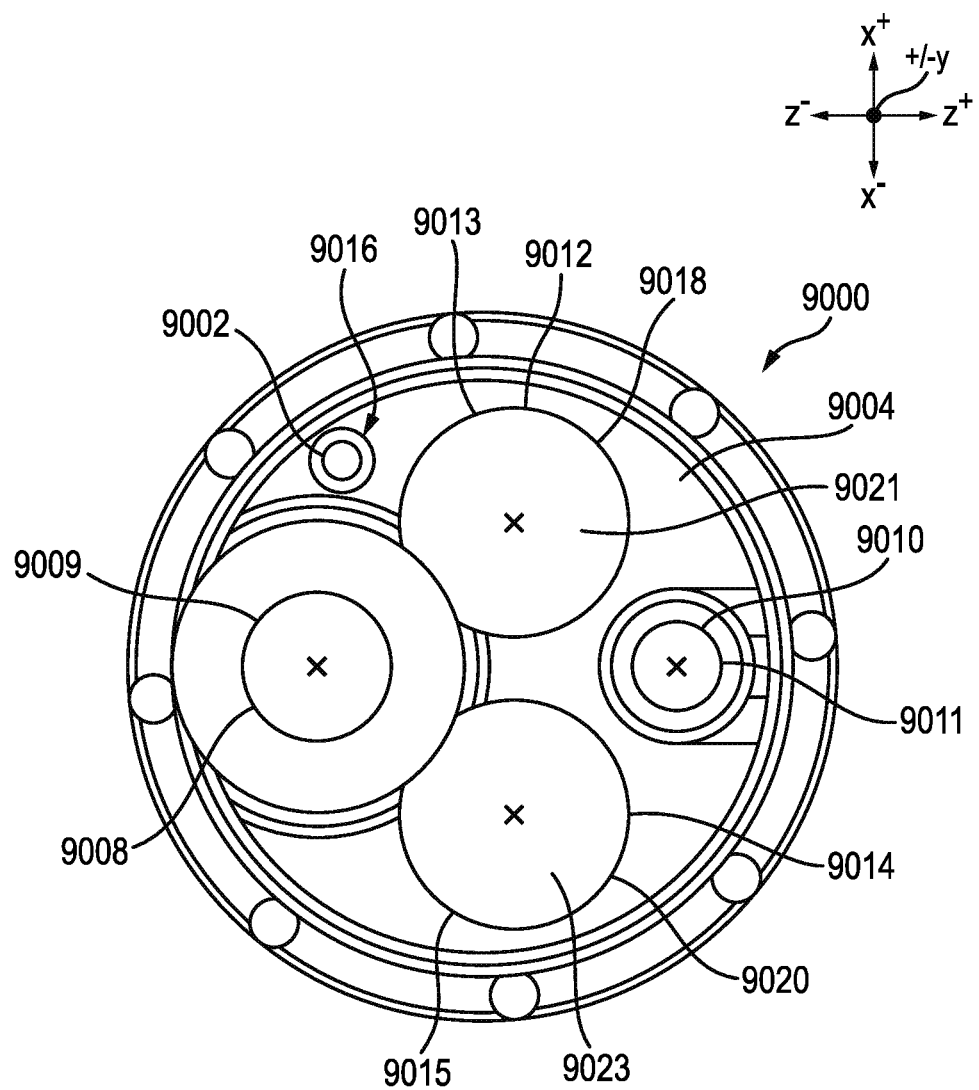
FIG. 30 is a top view of the sealing device of FIG. 29.

FIG. 29 and FIG. 30 illustrate a surgical sealing device 9000 that includes a seal housing 9002 with a predetermined size and shape and ports 9008, 9010, 9012, 9014 extending therethrough before any external force is applied to the ports. As shown in FIG. 29 and FIG. 30, the seal housing 9002 is illustrated in its predetermined size and shape. The seal housing 9002 can have a variety of configurations. For example, in this illustrated embodiment, the seal housing 9002 has an inner body member 9004 and an outer body member 9005 that is positioned about the inner body member 9004. In certain embodiments, the inner body member 9004 can be flexible relative to the outer body member 9005 or vice versa. Stated differently, the outer body member 9005 can be rigid relative to the inner body member 9004 or vice versa. In one embodiment, the inner body member and the outer body member are formed of the same material.

While any number of ports can be formed in the seal housing 9002, in this illustrated embodiment, four ports 9008, 9010, 9012, 9014 extend through sealing housing 9002. The ports can be formed in any suitable portion(s) of the seal housing 9002. For example, as shown in FIG. 29 and FIG. 30, all the ports 9008, 9010, 9012, 9014 extend through the inner body member 9004 of the seal housing 9002. Further, the ports 9008, 9010, 9012, 9014 can be movable with respect to the seal housing 9002 and each other, as discussed in more detail below. Such a configuration can help prevent interference between surgical instruments inserted through the various ports 9008, 9010, 9012, 9014 and can facilitate instrument positioning in a body cavity to which the surgical sealing device 9000 provides access thereto.

In some embodiments, as shown in FIG. 29 and FIG. 30, the sealing device 9000 can include a retractor 9006 that couples to and extends from a distal end 9002*d* of the seal housing 9002. The retractor 9006 can be configured to be placed in any opening within a patient's body, whether a natural body orifice or an opening made by an incision. As such, the retractor 9006 can function as a support structure for the seal housing 9002 and form a pathway through the opening in a patient's body so that surgical instruments can be inserted through the ports 9008, 9010, 9012, 9014 and into the interior body cavity or natural body lumen of the patient. Further, the retractor can additionally function as a retention element that is configured to affix the seal housing to tissue. In certain embodiments, in order to secure the seal housing within an incision or natural body orifice, a separate retention element 9007 can be used arranged on the exterior surface of retractor 9006, as shown in FIG. 29, and/or the exterior surface of the seal housing 9100.

The ports 9008, 9010, 9012, 9014 can be configured to form a seal around a surgical instrument inserted therethrough. For example, in some embodiments, at least one or more of the ports can include a sealing element, which can be positioned within the channel of the respective port. A sealing element can include at least one instrument seal and/or at least one channel seal, and can generally be configured to contact an instrument inserted through the sealing element's associated sealing port. For example, the port 9012 can include a sealing element 9021 arranged within the channel 9013 of the port 9012, and the port 9014 can include a sealing element 9023 arranged within the channel 9015 of the port 9014. While not illustrated, a person skilled in the art will appreciate that one or more of the other ports can include a sealing element (e.g., sealing element(s) structurally similarly to sealing elements 9021, 9023).

In some embodiments, the sealing element(s) can be in the form of a thin membrane formed of a flexible material which can be punctured or otherwise pierced by a surgical instrument. In addition, or alternatively, zero closure sealing elements such as a duck bill seal or other suitable seals for sealing in the absence of instrument can be used in association with the ports. The sealing elements can be positioned at any suitable location within the port.

The surgical sealing device 9000 can also include an insufflation port 9016 supported by the seal housing 9002, although a person skilled in the art will appreciate that the insufflation port 9016 can be located in other locations. A person skilled in the art will also appreciate that the insufflation port 9016 can have a variety of configurations. Generally, the insufflation port 9016 can be configured to pass an insufflation fluid into and/or out of a body cavity to which the surgical sealing device 9000 provides access to.

Figure 31:
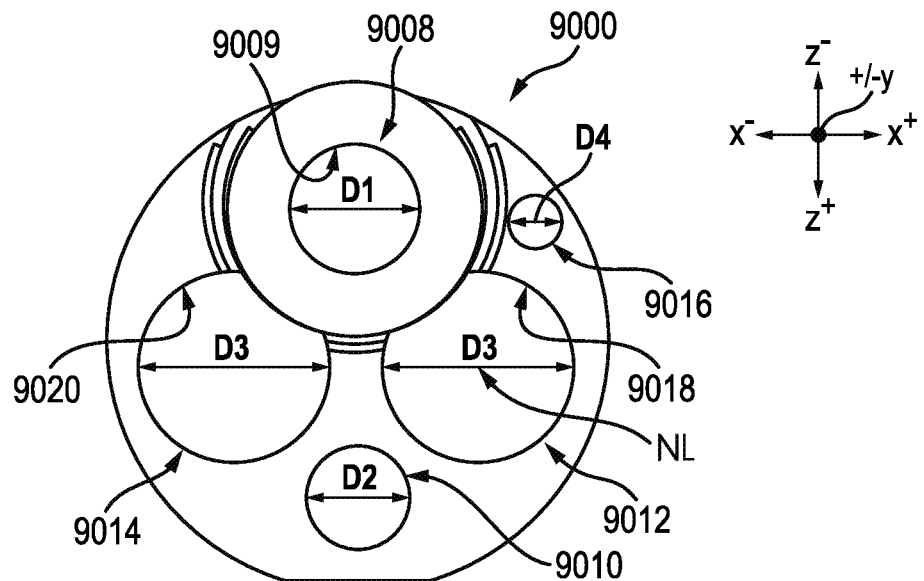
FIG. 31 is a schematic view of the ports of the surgical sealing port of FIG. 29.
Figure 32:
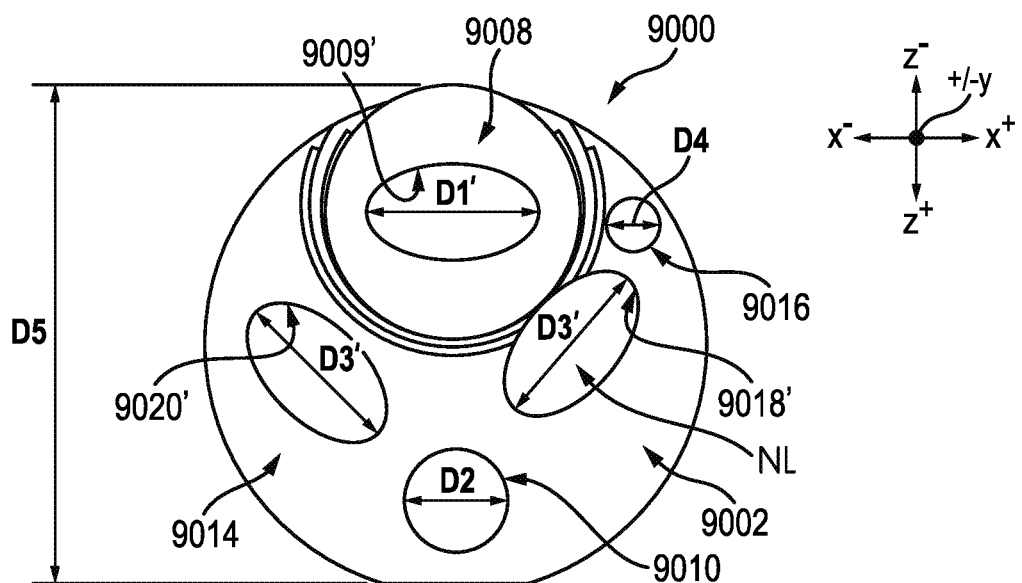
FIG. 32 is a schematic view of the altered ports of the surgical sealing port of FIG. 31.

FIG. 31 and FIG. 32 are schematic bottom views of the surgical sealing device 9000 with the retractor 9006 and the sealing elements 9021, 9023 removed. As stated above, the ports 9008, 9010, 9012, 9014 can have any combination of sizes and shapes. The port 9008 can have a diameter D1, port 9010 can have a diameter D2, and ports 9012, 9014 can have a diameter D3. The insufflation port opening 9016 can have any diameter D4. The diameter D3 of the ports 9012, 9014 can define a diameter of an orbital path of instruments arranged within the ports 9012, 9014.

When an instrument is inserted into one of the ports 9008, 9010, 9012, 9014, and a force is applied to the instrument, the port can adjust from a nominal size and shape to a selected size and shape based on the movement, direction, and force of the instrument. As shown in FIG. 31, the ports 9012, 9014 can include a nominal shape 9018, 9020, respectively. The nominal shape 9018, 9020 of the ports 9012, 9014 is the size and shape of the ports when no instrument is arranged therein and applying a force to the ports. Additionally, the port 9008 has a nominal size and shape 9009 when no instrument is arranged therein. In certain embodiments, the seal housing 9100 can have a diameter D5, which can be fixed or adjustable.

Each of the plurality of ports 9012, 9014 has a nominal size and shape 9018, 9020 and diameter D3, and each is configured to assume a selected size and/or shape 9018', 9020' that is different from the nominal size and shape 9018, 9020, wherein the selected size and/or shape 9018', 9020' of each port is constrained by the size and shape of each of the other plurality of ports. Additionally, the altered diameter D3' of the ports 9012, 9014 can further limit the planes in which an instrument can move. For example, as shown in FIG. 32, the ports 9012, 9014 have become narrower and oval shape, limiting an instrument within the ports to only be moveable in plane parallel to the diameter D3' of each port 9012, 9014. Since the limiting planes for ports 9012, 9014 are non-parallel, the instruments within the ports 9012, 9014 can be used to stabilize a third instrument within the port 9010.

An example of how the ports 9008, 9012, 9014 are altered from their nominal size and shapes 9009, 9018, 9020 to their selected size and shapes 9009', 9018', 9020' is as follows. An instrument (not shown) is inserted into each respective port 9008, 9010, 9012, 9014 parallel to the Y-axis. As the instrument arranged within the port 9008 is pivoted along the X-axis, the port 9008 changes from a nominal size and shape 9009 to a selected size and shape 9009' as a result of the instrument applying a force to the port 9008, causing the port 9008 react and change to an elongated shape along the X-axis. As the port 9008 is in the selected size and shape 9009', the instrument in the port 9012 can be moved along the Z-axis. However, due to the port 9008 already being elongated along the X-axis, the port 9012 will change from the nominal size and shape 9018 to the selected size and shape 9018'. As illustrated in FIG. 32, the port 9012 becomes elongated at an approximately 45° angle from the Z-axis, which was the intended axis of travel for the instrument. If the port 9008 was not in the selected size and shape 9009', then the selected size and shape of the port 9012 can be parallel to the Z-axis since the port 9008 would not be blocking the movement of the port 9012.

Additionally, the port 9014 operates similarly to the port 9012 where the intended direction of an instrument within the port 9014 is parallel to the Z-axis. However, similar to the port 9012, the selected size and shape 9020' of the port 9014 is limited by the selected size and shape 9009' of the port 9008. This forces the port 9014 to elongate at approximately a 135° angle relative to the Z-axis when moving from the nominal size and shape 9020 to the selected size and shape 9020'.

In certain embodiments, if the selected size and shape 9018' of the port 9012 was instead parallel to the X-axis, and the selected size and shape 9009' of the port 9008 remained parallel to the X-axis, then the selected size and shape of the port 9014 would be limited to moving only in the +Z axis and the +X-axis since the −Z axis would be blocked by the port 9008 and the −X-axis would be blocked by the port 9012.

In some embodiments, the sealing device can include restraining elements that can further control some but not all the movements and forces of the instruments inserted into the sealing device. For example, as shown in FIG. 30, port 9010 can includes a rigid structure 9011 encapsulated by the inner body member 9004. In other embodiments, one or more ports can include rigid restraining elements while one or more other ports can include flexible restraining elements that allows some movement in predefined directions of the ports with respect to each other while preventing other movements. In certain embodiments, the seal housing includes restraining features positioned in at least some directions tangential to the ports to substantially prevent stretching or movement of one port relative to another. This can be done in multiple planes for the same port or in selective directions to allow the port to float in other directions to improve maintenance of the seal around the instrument being inserted through the sealing device.

Figure 33:
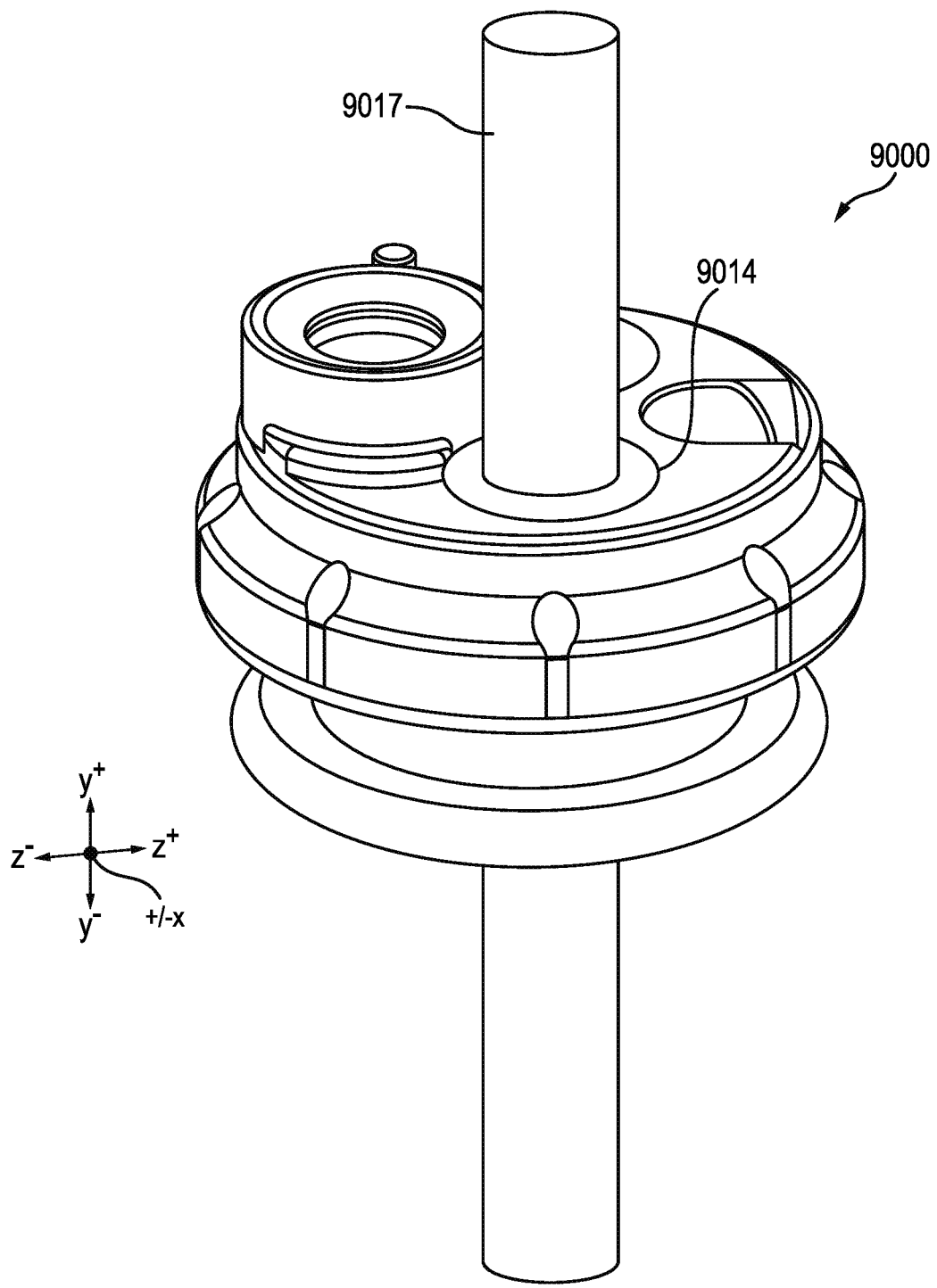
FIG. 33 is the sealing device of FIG. 29, showing an instrument inserted into one port of the sealing device.

In certain embodiments, one of the inserted instruments within one of the ports of the seal housing can function as a central anchoring tool. The central anchoring tool can be a designated instrument within one of the ports of the seal housing which supports the remaining instruments passing through other ports within the seal housing. In some embodiments, the central anchoring tool can be an instrument that does not interact with tissue directly, such as a camera or scope device passing through a port. Alternatively, the central anchoring tool can be an instrument (e.g., graspers, electrosurgical tool, etc.) that interacts with the tissue so that the additional instruments can be manipulated and supported without altering the anchor point of the seal housing. FIG. 33 illustrates an exemplary central anchor tool 9017 inserted into port 9014 of sealing device 9000.

Figure 34:
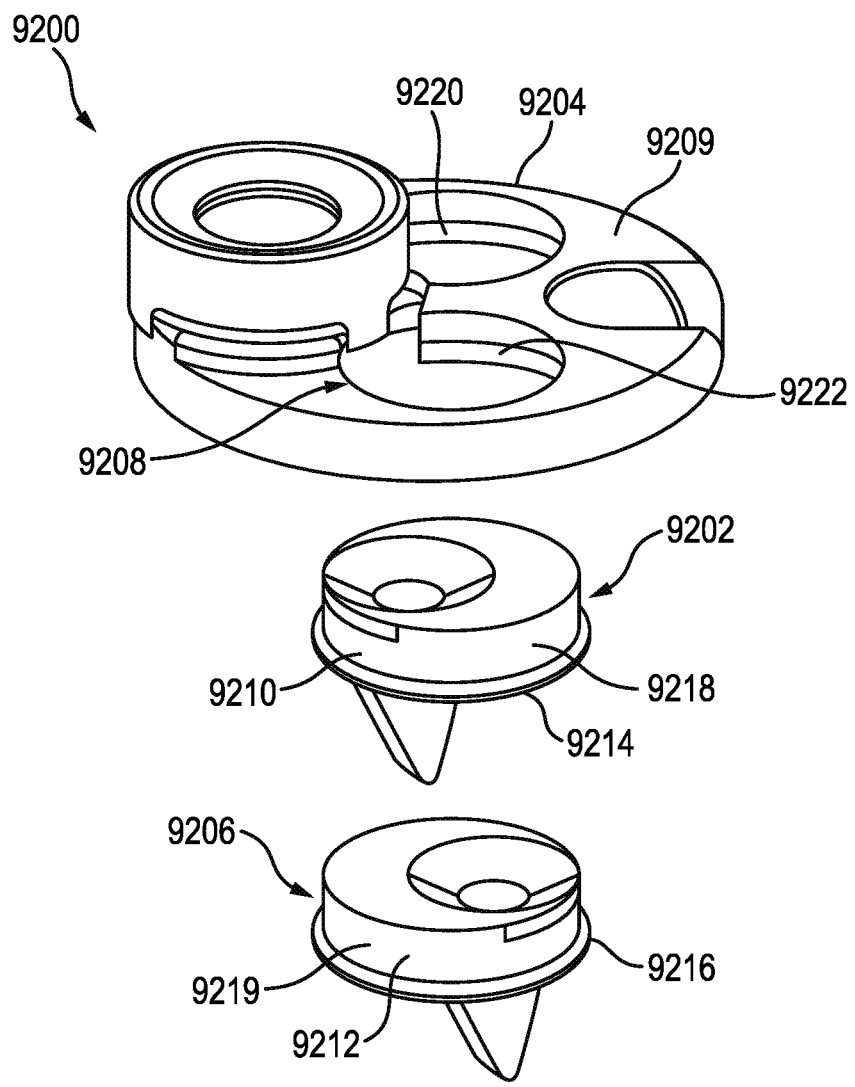
FIG. 34 is a schematic view of an exemplary embodiment of a surgical sealing system having threaded restraints.

In certain embodiments, at least one of the ports can include a threaded restraint arranged within a respective port, for example, as illustrated in FIG. 34. Aside from the differences described in detail below, sealing device 9200 can be similar to sealing device 9000 (FIG. 29) and therefore common features are not described in detail herein. As shown a first threaded restraint 9202 is configured to be arranged in a first port 9204 and a second threaded restraint 9206 is configured to be arranged in second port 9208. Each threaded restraint 9202, 9206 is configured to fixate an instrument arranged within each respective port 9204, 9208 to the seal housing 9209 and each of the threaded restraints 9202, 9206 is configured to contact the outer surface of the instrument. While the threaded restraints 9202, 9206 can have a variety of configurations, in this illustrated embodiment, each of the first and second threaded restraints 9202, 9206 includes a generally cylindrical body 9210, 9212 with threads 9214, 9216 on its outer surface 9218, 9219. The threads 9214, 9216 are configured to threadably engage corresponding threads 9220, 9222 on each respective first and second ports 9204, 9208.

During use, as an instrument is inserted into and rotated within the first port 9204 or the second port 9208, the respective first or second threaded restraint 9202, 9206 also rotates, thereby tightening the respective first or second threaded restraint 9202, 9206 relative to the seal housing 9209. As the threaded restraint 9202, 9206 tightens, the range of motion available to the inserted instrument decreases. Once the threaded restraint 9202, 9206 is fully tightened, the instrument is fixated to the seal housing 9209.

While fixated, the instrument can serve as an anchor for the other instruments within the other ports 9204, 9208 of the seal housing 9209.

In other embodiments, the sealing systems can include integrated mechanism or electronic activated restriction systems to provide selective support or floating (e.g., moving) operation. For example, a fluidic coupling cylinder with a selectively sizeable valve can be employed on or in the seal housing to inhibit motion. In certain embodiments, a solenoid valve can be used to inhibit circular fluid motion.

In some embodiments, the ports can be configured to change shape and size in response to an external energy being applied to the ports. For example, each of the plurality of ports 9012, 9014 can be formed of a ferromagnetic material that is configured to be structurally altered in response to exposure to an electromagnet. During use, the electromagnet can apply a magnetic flux to the ports 9012, 9014 to cause the ports 9012, 9014 to alter their at least their shape compared to their shape when the electromagnet is switched off.

Any one or more of the exemplary surgical sealing systems, devices and related methods described herein, and variations thereof, can be implemented in conventional surgical procedures conducted by a medical professional as well as in robotic-assisted surgical procedures. Various teachings herein may be readily incorporated into a robotic surgical system such as one or more of the DAVINCI™ systems by Intuitive Surgical, Inc., of Sunnyvale, Calif., including their SP™ surgical system. Exemplary robotic surgical systems and related features, which may be combined with any one or more of the exemplary surgical access devices and methods disclosed herein, are disclosed in the following: U.S. Pat. No. 8,068,649, entitled "Method and Apparatus for Transforming Coordinate Systems in a Telemanipulation System," issued Nov. 29, 2011; U.S. Pat. No. 8,517,933, entitled "Retraction of Tissue for Single Port Entry, Robotically Assisted Medical Procedures," issued Aug. 27, 2013; U.S. Pat. No. 8,545,515, entitled "Curved Cannula Surgical System," issued Oct. 1, 2013; U.S. Pat. No. 8,551,115, entitled "Curved Cannula Instrument," issued Oct. 8, 2013; U.S. Pat. No. 8,623,028, entitled "Surgical Port Feature," issued Jan. 7, 2014, the disclosure of which is incorporated by reference herein; U.S. Pat. No. 8,771,180, entitled "Retraction of Tissue for Single Port Entry, Robotically Assisted Medical Procedures," issued Jul. 8, 2014, the disclosure of which is incorporated by reference herein; U.S. Pat. No. 8,888,789, entitled "Curved Cannula Surgical System Control," issued Nov. 18, 2014; U.S. Pat. No. 9,254,178, entitled "Curved Cannula Surgical System," issued Feb. 9, 2016; U.S. Pat. No. 9,283,050, entitled "Curved Cannula Surgical System," issued Mar. 15, 2016; U.S. Pat. No. 9,320,416, entitled "Surgical Instrument Control and Actuation," issued Apr. 26, 2016, the disclosure of which is incorporated by reference herein; U.S. Pat. No. 9,339,341, entitled "Direct Pull Surgical Gripper," issued May 17, 2016; U.S. Pat. No. 9,358,074, entitled "Multi-Port Surgical Robotic System Architecture," issued Jun. 7, 2016; U.S. Pat. No. 9,572,481, entitled "Medical System with Multiple Operating Modes for Steering a Medical Instrument Through Linked Body Passages," issued Feb. 21, 2017; U.S. Pat. No. 9,636,186, entitled "Multi-User Medical Robotic System for Collaboration or Training in Minimally Invasive Surgical Procedures," issued May 2, 2017; U.S. Pat. Pub. No. 2014/0066717, entitled "Surgical Port Feature," published Mar. 6, 2014, issued as U.S. Pat. No. 10,245,069 on Apr. 2, 2019, the disclosure of which is incorporated by reference herein; U.S. Pat. Pub. No. 2017/0128041, entitled "Laparoscopic Ultrasound Robotic Surgical System," published May 11, 2017; and U.S. Pat. Pub. No. 2017/0128144, entitled "Laparoscopic Ultrasound Robotic Surgical System," published May 11, 2017, the disclosure of which is incorporated by reference herein; and U.S. Pat. Pub. No. 2017/0128145, entitled "Laparoscopic Ultrasound Robotic Surgical System," published May 11, 2017. The disclosure of each of these references is incorporated by reference herein.

Figure 35:
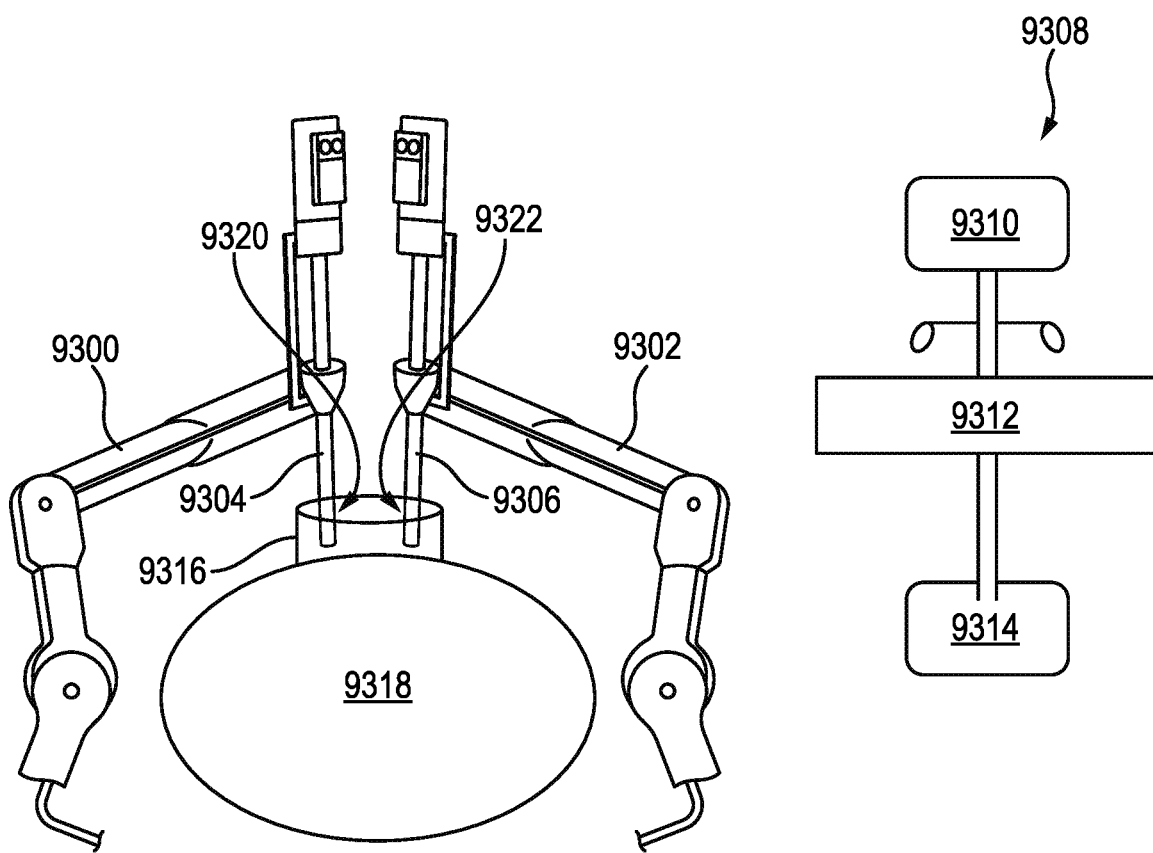
FIG. 35 is a schematic of an exemplary embodiment of a surgical robotic system that includes electromechanical arms each having a surgical instrument mounted thereto, and being wirelessly coupled to a control system.

FIG. 35 illustrates an exemplary embodiment of two robotic arms 9300, 9302, each having a surgical instrument 9304, 9306 attached thereto. The robotic arms 9300, 9302 can be wirelessly coupled to a control system 9308 having a console, with a display 9310, a controller 9312, and a user input device 9314. As shown, seal housing 9316 is partially inserted into a patient's body 9318, and each surgical instrument 9304, 9306 is inserted into a respective port 9320, 9322 of the seal housing 9316. In certain embodiment, the robotic arm(s) 9300, 9302 can be configured to create a compression loading around the ports to the prevent motion of the surgical instruments 9304, 9306.

In some embodiments, the controller 9312 is configured to receive a force reading from at least one of the plurality of ports 9008, 9010, 9012, 9014 (see FIG. 32) based on the movement, direction, and force of an instrument. For example, a force sensor (not shown) can be arranged on each robotic arm 9300, 9302 such that the force applied by each arm can be measured and sent to the controller 9312. Based on the measured force readings, the controller 9312 can determine a selected size and shape 9018', 9020' of ports 9012, 9014 (see FIG. 32) based on the amount of force the inserted instruments 9304, 9306 is applying to such ports 9012, 9014. Based on the determined selected size and shape 9018', 9020', the robotic arm(s) 9300, 9302 can be moved by the user in such a way that can alter the size and shape of the ports 9012, 9014 to stabilize at least one other instrument (not shown) positioned within at least one of the other ports 9008, 9010.

In certain embodiments, a tool driver restraint of a trocar access port can be used in combination with the surgical sealing device 9000. The trocar access port can be used to limit the force applied to an instrument shaft, allowing for a robotic arm to control the forces. The robotic arm restraint of the trocar access port can be used to allow the tool driver restraint to provide a stabilizing force to the surgical sealing device 9000, and not instruments inserted through the ports. In this embodiment, the diameter of the trocar access port is the key rigidity factor, rather than the diameter D5 of the surgical sealing device 9000. In certain embodiments, a cannula from which multiple instruments are deployed from does not have a static end lumen. Instead, the cannula is segmented into two or more curved members. The curved members can be driven to different depths within tissue to provide for a local force reaction to the instrument that is against that respective cannula segment.

Figure 36:
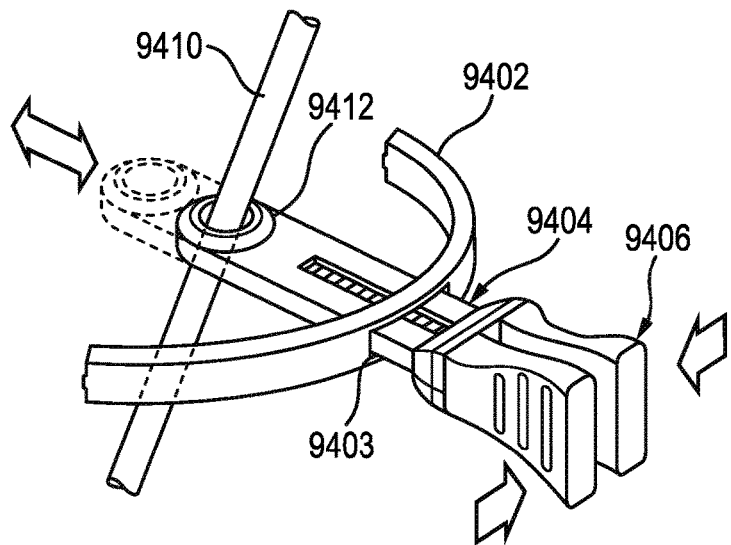
FIG. 36 is schematic view of an embodiment of a locking arm.

In certain embodiments, one of the ports can further include a locking arm configured to lock a position of the at least one port relative to the seal housing. FIG. 36 illustrates an exemplary embodiment of a seal housing 9402 having a slot 9403 arranged therein such that a locking arm 9404 can pass through the slot 9403 and into the seal housing 9402. As shown, the locking arm 9404 include locking tabs 9406, which are configured to be selectively depressed to allow the locking arm 9405 to move relative to the seal housing 9402. Arranged at a distal end of the locking arm 9404 is a port 9412, with an instrument 9410 arranged within the port 9412. Due to the arrangement of the locking arm 9404, the port 9412 can be moved relative to the seal housing 9402. Other suitable configurations of a locking arm are also contemplated herein. For example, another configuration of the locking arm can include a base member having a plurality of rotatable rings. A top rotatable ring can contain a flexible sealing member, and one or more other rotatable rings each can have sealing arms extending therefrom and can be stacked one on top of the other beneath the sealing member. Each ring can be individually rotatable relative to the other rings and relative to the sealing member. Each of the sealing arms can include a sealing element positioned at one end thereof and configured to form a seal around an instrument inserted therethrough.

Figure 37:
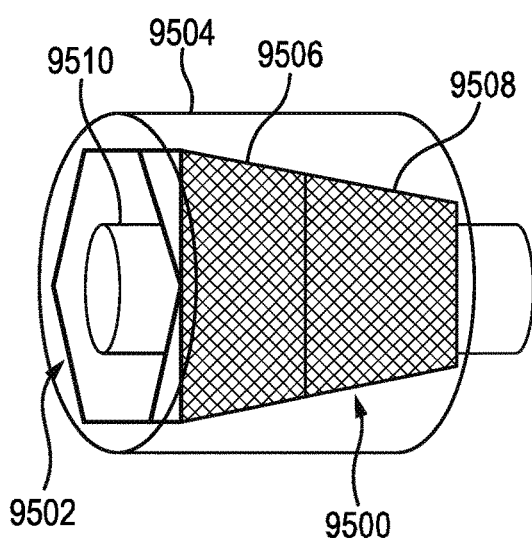
FIG. 37 is a schematic view of one embodiment of a locking structure prior to exposure to external energy.
Figure 38:
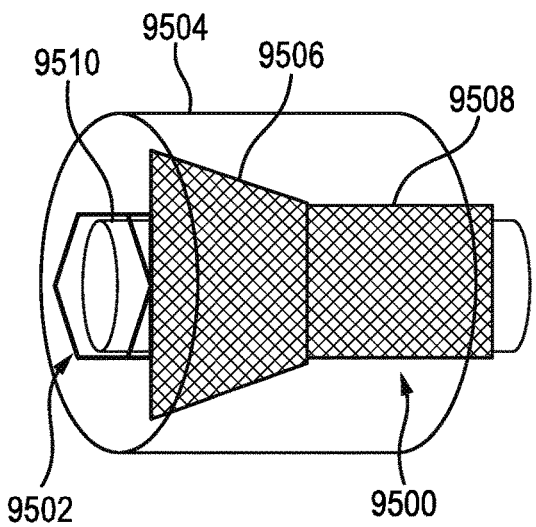
FIG. 38 is the locking structure of FIG. 37 after exposure to external energy.

FIG. 37 and FIG. 38 illustrate an exemplary embodiment of a locking seal 9500 arranged within at least one port 9502 of a seal housing 9504. The locking seal 9500 can be in the form of a honeycomb locking structure which interacts with an instrument 9510 passing therethrough. The shape of the locking seal 9500 can be adjusted through the application of external energy, such as heat, light, or electrical current. As illustrated in FIG. 38, after exposure to external energy, the locking seal 9500 can deform into a first portion 9506 and a second portion 9508. When deformed, the second portion 9508 can contact the instrument 9510 so that the instrument 9510 is locked in position to the seal housing 9504.

In certain embodiments, a surgical sealing device can further include changeable ports as restraining means to control some, but not all movements and forces of instruments inserted therethrough the ports of the surgical sealing device. The ports of the surgical sealing device can include sections that are formed from 4D printed material and then over molded into an elastomer section of a seal with a port. 4D printing is an additive manufacturing process through which a 3D printed object includes transformable components (e.g., hydrogel, shape memory polymer) such that the 3D printed object transforms itself into another structure over the influence of external energy input as temperature, light or other environmental stimuli. 4D printing is similar to 3D printing in the sense that an object is also built layer by layer, but the object can then change over time after its initial manufacture. The object will change because it is printed with materials that have the ability to change when exposed to certain factors: such as heat, magnetic, water, light or another source of energy.

In some embodiments, the ports including a 4D printed material initially can be in a flexible condition to allow for introduction and manipulation of instruments through the ports. At defined conditions, the surgical sealing device can have an external energy applied thereto to alter the structure of the 4D printed material thus changing the geometry of the seal interface with respect to the instrument and/or lock to the seal itself. Additionally, the 4D printed material can interlock all the ports of a surgical sealing device and instruments inserted therein to create rigid restraints allowing some movement of the instruments in predefined directions with respect to each other while preventing some movements of the instruments in other directions. The prevention of movement in some directions allows for an instrument interacting with the 4D printed material to stabilize the other instruments within the surgical sealing device.

An example of how a 4D printed material would interact with an instrument within a port is as follows. A honeycomb structure can be formed of 4D printed material and integrated with the pivotal seals within each of the ports of the surgical sealing device. The honeycomb structure can be in a triangular or hexagonal pattern that allows an instrument shaft to freely pass through the seal. When needed or activated by heat, pressure, light or an energy source, the honeycomb structure alters its form for to make contact with the instrument shaft. Contact is made by the triangular or hexagonal honeycomb bending inward towards the instrument shaft, compressing the honeycomb structure and/or seal material against the shaft.

In certain embodiments, the surgical sealing device can include a 3D printed housing support structure having an elastomer structural member. The elastomer structural member can be pneumatically actuated between a fix and no fixed state in order to fixate instrument inserted through the ports of the surgical sealing system.

The surgical devices disclosed herein can be designed to be disposed of after a single use, or they can be designed to be used multiple times. In either case, however, the surgical devices can be reconditioned for reuse after at least one use. Reconditioning can include any combination of the steps of disassembly of the surgical devices, followed by cleaning or replacement of particular pieces and subsequent reassembly. In particular, the surgical devices can be disassembled, and any number of the particular pieces or parts of the surgical devices can be selectively replaced or removed in any combination. Upon cleaning and/or replacement of particular parts, the surgical devices can be reassembled for subsequent use either at a reconditioning facility, or by a surgical team immediately prior to a surgical procedure. Those skilled in the art will appreciate that reconditioning of a surgical device can utilize a variety of techniques for disassembly, cleaning/replacement, and reassembly. Use of such techniques, and the resulting reconditioned instrument, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. It will be appreciated that the terms "proximal" and "distal" are used herein, respectively, with reference to the top end (e.g., the end that is farthest away from the surgical site during use) and the bottom end (e.g., the end that is closest to the surgical site during use) of a surgical instrument, respectively, that is configured to be mounted to a robot. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A surgical sealing system, comprising:
a sealing device having a seal housing with a predetermined size and shape, the seal housing being configured to be at least partially disposed within a body cavity and having a plurality of ports;
wherein each of the plurality of ports has a nominal orientation, size and shape and each is configured to assume a selected orientation, size and shape that is different from the nominal orientation, size and shape, the selected orientation, size and shape of each port being determined responsive to the orientation, size and shape of each of the other plurality of ports;
wherein each of the plurality of ports is configured to form a seal around an instrument inserted therethrough; and
wherein an orientation, size and/or shape of a first port of the plurality of ports, with a first instrument inserted therethrough, and a first force applied thereto is effective to change an orientation, size and/or shape of at least one second port of the plurality of ports, to limit the movement of at least one second instrument positioned within the at least one second port based on the orientation, size and/or shape of the first port.

2. The surgical sealing system of claim 1, further comprising at least one electromechanical arm, and wherein at least one instrument that is inserted into a respective port of the plurality of ports is connected to the at least one electromechanical arm.

3. The surgical sealing system of claim 1, wherein the first port of the plurality of ports is configured to apply the first force to the first instrument that is inserted therethrough to thereby limit movement thereof within a first plane, and the at least one second port is configured to apply at least one second force to the at least one second instrument that is inserted therethrough to thereby limit movement thereof within at least one second plane, the at least one second plane being non-parallel to the first plane.

4. The surgical sealing system of claim 1, wherein at least one port of the plurality of ports includes a threaded restraint configured to fixate an instrument inserted therethrough.

5. The surgical sealing system of claim 1, wherein the first instrument and the at least one second instrument that are inserted into the first port and the at least one second port, respectively, are stabilized simultaneously by a central anchoring tool that is configured to be inserted through a third port of the plurality of ports.

6. The surgical system of claim 1, wherein one or more ports of the plurality of ports are rigid relative to one or more other ports of the plurality of ports.

7. The surgical sealing system of claim 1, wherein at least one port of the plurality of ports is configured to change shape and size in response to external energy being applied thereto.

8. The surgical sealing system of claim 1, wherein at least one port of the plurality of ports is formed of a ferromagnetic material that is configured to be structurally altered in response to exposure to an electromagnet.

9. The surgical sealing system of claim 1, wherein at least one port of the plurality of ports includes a locking arm arranged within a slot of the seal housing, the locking arm being configured to lock a position of the at least one port relative to the seal housing.

10. The surgical sealing system of claim 1, wherein the sealing housing further comprises a flexible inner body member and a rigid outer body member, wherein each port of the plurality of ports is arranged within the inner body member.

11. The surgical sealing system of claim 10, wherein at least one port of the plurality of ports includes a rigid ring encapsulated by the flexible inner body member.

12. The surgical sealing system of claim 1, wherein at least one port of the plurality of ports includes a locking structure that is configured to interact and collapse around an instrument passing therethrough to fixate the inserted instrument within the at least one port.

13. The surgical sealing system of claim 12, wherein the locking structure has a honeycomb configuration.

14. The surgical sealing system of claim 1, wherein the sealing device comprises a retractor that is coupled to the seal housing and configured to be positioned in a natural body orifice or an opening formed in tissue.

15. The surgical sealing system of claim 1, wherein the sealing device comprises at least one retention element that is configured to affix the seal housing to tissue.

* * * * *